(12) United States Patent
Kassab et al.

(10) Patent No.: US 11,000,205 B2
(45) Date of Patent: May 11, 2021

(54) DEVICES AND SYSTEMS FOR NAVIGATION AND POSITIONING A CENTRAL VENOUS CATHETER WITHIN A PATIENT

(71) Applicant: Bard Access Systems, Inc., Salt Lake City, UT (US)

(72) Inventors: Ghassan S. Kassab, La Jolla, CA (US); William Combs, Galena, OH (US); Mark Svendsen, Bloomington, IN (US); H. Toby Markowitz, Roseville, MN (US)

(73) Assignee: Bard Access Systems, Inc., Salt Lake City, UT (US)

( * ) Notice: Subject to any disclaimer, the term of this patent is extended or adjusted under 35 U.S.C. 154(b) by 210 days.

(21) Appl. No.: 14/394,204

(22) PCT Filed: Apr. 5, 2013

(86) PCT No.: PCT/US2013/035527
§ 371 (c)(1),
(2) Date: Oct. 13, 2014

(87) PCT Pub. No.: WO2013/152335
PCT Pub. Date: Oct. 10, 2013

(65) Prior Publication Data
US 2015/0080762 A1 Mar. 19, 2015

Related U.S. Application Data

(60) Provisional application No. 61/776,655, filed on Mar. 11, 2013, provisional application No. 61/620,872, filed on Apr. 5, 2012.

(51) Int. Cl.
*A61B 5/06* (2006.01)
*A61B 5/00* (2006.01)
(Continued)

(52) U.S. Cl.
CPC .............. *A61B 5/062* (2013.01); *A61B 5/063* (2013.01); *A61B 5/068* (2013.01); *A61B 5/6847* (2013.01);
(Continued)

(58) Field of Classification Search
CPC ... A61B 5/02007; A61B 5/053; A61B 5/0538; A61B 5/061; A61B 5/062; A61B 5/063;
(Continued)

(56) References Cited

U.S. PATENT DOCUMENTS 3,896,373 A 7/1975 Zelby
3,986,373 A 10/1976 Goodlaxson
(Continued)

FOREIGN PATENT DOCUMENTS

CN 102118994 A 7/2011
EP 0486979 A1 5/1992
(Continued)

OTHER PUBLICATIONS

Konings, M. K. et al. "Correct positioning of central venous catheters using a new electric method," J Vasc Access Mar. 9, 2015; 16 (4): 327-332.
(Continued)

*Primary Examiner* — Devin B Henson
(74) *Attorney, Agent, or Firm* — Rutan & Tucker LLP

(57) ABSTRACT

Devices and systems for navigation and positioning a central venous catheter within a patient. In an exemplary embodiment of a system of the present disclosure, the system comprises a first pole and a second pole, the first pole and the second pole configured to generate an electric field within a mammalian body sufficient to obtain a plurality of field measurements therein, and an elongated body configured for at least partial insertion into a blood vessel of the mammalian body and advancement through a vasculature,
(Continued)

said advancement dependent upon the plurality of field measurements indicative of one or more locations of a portion of the elongated body within the vasculature. In at least one embodiment, the elongated body is configured as a stylet.

21 Claims, 24 Drawing Sheets

(51) Int. Cl.
  *A61B 5/107* (2006.01)
  *A61M 25/00* (2006.01)
  *A61M 25/01* (2006.01)
  *A61M 25/09* (2006.01)
(52) U.S. Cl.
  CPC ....... *A61B 5/6852* (2013.01); *A61M 25/0017* (2013.01); *A61M 25/0105* (2013.01); *A61M 25/09* (2013.01); *A61B 5/1076* (2013.01); *A61M 2025/0008* (2013.01); *A61M 2025/0166* (2013.01)
(58) Field of Classification Search
  CPC ....... A61B 5/065; A61B 5/068; A61B 5/6851; A61B 5/6852; A61B 2017/00026; A61B 5/02014; A61M 2025/0008; A61M 2025/0166
  See application file for complete search history.

(56) References Cited

U.S. PATENT DOCUMENTS

| | | |
|---|---|---|
| 4,327,723 A | 5/1982 | Frankhouser |
| 4,365,639 A | 12/1982 | Goldreyer |
| 4,380,237 A | 4/1983 | Newbower |
| 4,417,886 A | 11/1983 | Frankhouser et al. |
| 4,562,843 A | 1/1986 | Djordjevich et al. |
| 4,587,975 A | 5/1986 | Salo et al. |
| 4,644,960 A | 2/1987 | Johans |
| 4,660,571 A | 4/1987 | Hess et al. |
| 4,840,182 A | 6/1989 | Carlson |
| 4,841,977 A | 6/1989 | Griffith et al. |
| 4,873,987 A | 10/1989 | Djordjevich et al. |
| 4,899,759 A | 2/1990 | Pederson et al. |
| 4,911,174 A | 3/1990 | Pederson et al. |
| 4,957,110 A | 9/1990 | Vogel et al. |
| 5,004,456 A | 4/1991 | Botterbusch et al. |
| 5,058,583 A | 10/1991 | Geddes et al. |
| 5,078,678 A | 1/1992 | Katims |
| 5,121,750 A | 6/1992 | Katims |
| 5,125,410 A | 6/1992 | Misono et al. |
| 5,174,299 A | 12/1992 | Nelson |
| 5,205,830 A | 4/1993 | Dassa et al. |
| 5,233,994 A | 8/1993 | Shmulewitz |
| 5,243,995 A | 9/1993 | Maier |
| 5,246,426 A | 9/1993 | Lewis et al. |
| 5,275,162 A | 1/1994 | Edwards et al. |
| 5,366,443 A | 11/1994 | Eggers et al. |
| 5,417,208 A | 5/1995 | Winkler |
| 5,453,576 A | 9/1995 | Krivitski |
| 5,522,880 A | 6/1996 | Barone et al. |
| 5,536,248 A | 7/1996 | Weaver et al. |
| 5,555,618 A | 9/1996 | Winkler |
| 5,599,299 A | 2/1997 | Weaver et al. |
| 5,603,333 A | 2/1997 | Konings |
| 5,634,465 A | 6/1997 | Schmiesing et al. |
| 5,665,103 A | 9/1997 | Lafontaine et al. |
| 5,702,433 A | 12/1997 | Taylor et al. |
| 5,769,786 A | 6/1998 | Wiegel |
| RE35,924 E | 10/1998 | Winkler |
| 5,827,192 A | 10/1998 | Gopakumaran et al. |
| 5,836,875 A * | 11/1998 | Webster, Jr. ......... A61B 5/0422 600/374 |
| 5,842,998 A | 12/1998 | Gopakumaran et al. |
| 5,971,933 A | 10/1999 | Gopakumaran et al. |
| 6,011,988 A | 1/2000 | Lynch et al. |
| 6,080,149 A | 6/2000 | Huang et al. |
| 6,081,737 A | 6/2000 | Shah |
| 6,112,115 A | 8/2000 | Feldman et al. |
| 6,165,977 A | 12/2000 | Mochly-Rosen |
| 6,187,744 B1 | 2/2001 | Rooney |
| 6,190,370 B1 | 2/2001 | Tsui |
| 6,191,136 B1 | 2/2001 | Marban |
| 6,231,518 B1 | 5/2001 | Grabek et al. |
| 6,233,994 B1 | 5/2001 | Roy et al. |
| 6,258,035 B1 | 7/2001 | Hoeksel et al. |
| 6,270,493 B1 | 8/2001 | Lalonde et al. |
| 6,273,855 B1 | 8/2001 | Schmid et al. |
| 6,287,260 B1 | 9/2001 | Hascoet et al. |
| 6,324,416 B1 | 11/2001 | Seibert |
| 6,325,762 B1 | 12/2001 | Tjin |
| 6,354,999 B1 | 3/2002 | Dgany et al. |
| 6,360,123 B1 | 3/2002 | Kimchi et al. |
| 6,398,738 B1 | 6/2002 | Millar |
| 6,406,422 B1 | 6/2002 | Landesberg |
| 6,456,874 B1 | 9/2002 | Hafer et al. |
| 6,471,656 B1 | 10/2002 | Shalman et al. |
| 6,471,658 B1 | 10/2002 | Daniels et al. |
| 6,477,402 B1 | 11/2002 | Lynch et al. |
| 6,494,832 B1 | 12/2002 | Feldman et al. |
| 6,503,202 B1 | 1/2003 | Hossack et al. |
| 6,506,159 B2 | 1/2003 | Hascoet et al. |
| 6,511,413 B1 | 1/2003 | Landesberg |
| 6,514,226 B1 | 2/2003 | Levin et al. |
| 6,545,678 B1 | 4/2003 | Ohazama |
| 6,569,103 B2 | 5/2003 | Hoeksel et al. |
| 6,569,862 B1 | 5/2003 | Marban |
| 6,652,505 B1 | 11/2003 | Tsugita |
| 6,663,661 B2 | 12/2003 | Boneau |
| 6,666,828 B2 | 12/2003 | Greco et al. |
| 6,711,429 B1 | 3/2004 | Gilboa et al. |
| 6,799,064 B1 * | 9/2004 | Hassett ................ A61B 5/0422 600/374 |
| 6,887,206 B2 | 5/2005 | Hoeksel et al. |
| 6,905,469 B2 | 6/2005 | Hascoet et al. |
| 6,922,579 B2 * | 7/2005 | Taimisto ............ A61B 18/1492 600/374 |
| 6,926,674 B2 | 8/2005 | Tenerz et al. |
| 6,939,313 B2 | 9/2005 | Saadat et al. |
| 6,986,744 B1 | 1/2006 | Krivitski |
| 7,065,403 B1 | 6/2006 | Mouchawar et al. |
| 7,069,072 B2 | 6/2006 | Jansen et al. |
| 7,128,734 B1 | 10/2006 | Wilson et al. |
| 7,141,019 B2 | 11/2006 | Pearlman |
| 7,169,107 B2 | 1/2007 | Jersey-Willuhn et al. |
| 7,169,109 B2 | 1/2007 | Jansen et al. |
| 7,189,205 B2 | 3/2007 | McMorrow et al. |
| 7,189,208 B1 | 3/2007 | Beatty et al. |
| 7,236,820 B2 | 6/2007 | Mabary et al. |
| 7,270,662 B2 | 9/2007 | Visram et al. |
| 7,300,430 B2 | 11/2007 | Wilson et al. |
| 7,311,702 B2 | 12/2007 | Tallarida et al. |
| 7,326,241 B2 | 2/2008 | Jang |
| 7,381,204 B2 | 6/2008 | Wilson et al. |
| 7,454,244 B2 | 11/2008 | Kassab et al. |
| 7,519,424 B2 | 4/2009 | Dennis et al. |
| 7,599,730 B2 | 10/2009 | Hunter et al. |
| 7,601,138 B2 | 10/2009 | Goebel et al. |
| 7,616,992 B2 | 11/2009 | Dennis et al. |
| 7,627,376 B2 | 12/2009 | Dennis et al. |
| 7,697,972 B2 | 4/2010 | Verard et al. |
| 7,715,925 B2 | 5/2010 | Hafer et al. |
| 7,763,196 B2 | 7/2010 | Goebel et al. |
| 7,774,055 B1 | 8/2010 | Min |
| 7,775,986 B2 | 8/2010 | Roeher et al. |
| 7,833,214 B2 | 11/2010 | Wilson et al. |
| 7,846,157 B2 | 12/2010 | Kozel |
| 7,854,740 B2 | 12/2010 | Carney |
| 7,917,193 B2 | 3/2011 | Crane |
| 7,967,782 B2 | 6/2011 | Laufer et al. |
| 8,046,052 B2 | 10/2011 | Verard et al. |
| 8,060,185 B2 | 11/2011 | Hunter et al. |

(56) References Cited

U.S. PATENT DOCUMENTS

| | | | |
|---|---|---|---|
| 8,078,274 B2 | 12/2011 | Kassab | |
| 8,078,279 B2 | 12/2011 | Dennis et al. | |
| 8,082,032 B2 | 12/2011 | Kassab et al. | |
| 8,099,161 B2 | 1/2012 | Kassab | |
| 8,114,143 B2 | 2/2012 | Kassab et al. | |
| 8,133,698 B2 | 3/2012 | Silver | |
| 8,185,205 B2 | 5/2012 | Ben-David et al. | |
| 8,204,582 B2 | 6/2012 | Zantos et al. | |
| 8,221,402 B2 | 7/2012 | Francischelli et al. | |
| 8,241,274 B2 | 8/2012 | Keogh et al. | |
| 8,244,339 B2 | 8/2012 | Shen et al. | |
| 8,280,477 B2 * | 10/2012 | Lau | A61B 5/042 600/374 |
| 8,303,505 B2 | 11/2012 | Webler et al. | |
| 8,326,419 B2 | 12/2012 | Rosenberg et al. | |
| 8,374,689 B2 | 2/2013 | Gopinathan et al. | |
| 8,388,541 B2 | 3/2013 | Messerly et al. | |
| 8,388,546 B2 | 3/2013 | Rothenberg | |
| 8,401,616 B2 | 3/2013 | Verard et al. | |
| 8,409,103 B2 | 4/2013 | Grunwald et al. | |
| 8,494,794 B2 | 7/2013 | Dutta et al. | |
| 8,521,249 B2 | 8/2013 | O'Dea | |
| 8,597,193 B2 | 12/2013 | Grunwald et al. | |
| 8,632,469 B2 | 1/2014 | Kassab | |
| 8,798,712 B2 | 8/2014 | Gopinathan et al. | |
| 8,825,151 B2 | 9/2014 | Gopinathan et al. | |
| 9,006,708 B2 | 4/2015 | Bennett et al. | |
| 9,066,708 B2 | 6/2015 | Kassab | |
| 10,172,538 B2 | 1/2019 | Kassab | |
| 2001/0012934 A1 | 8/2001 | Chandrasekaran et al. | |
| 2002/0049488 A1 | 4/2002 | Boneau | |
| 2002/0087089 A1 | 7/2002 | Ben-Haim | |
| 2002/0129952 A1 | 9/2002 | Matsudate et al. | |
| 2002/0165537 A1 | 11/2002 | Kelley et al. | |
| 2002/0177783 A1 | 11/2002 | Khalil | |
| 2003/0013986 A1 | 1/2003 | Saadat | |
| 2003/0130711 A1 | 7/2003 | Pearson et al. | |
| 2003/0149368 A1 | 8/2003 | Hennemann et al. | |
| 2003/0163128 A1 | 8/2003 | Patil et al. | |
| 2003/0171894 A1 | 9/2003 | Giovanni Battista Mancini et al. | |
| 2003/0195433 A1 | 10/2003 | Turovskiy et al. | |
| 2004/0019447 A1 | 1/2004 | Shachar | |
| 2004/0024329 A1 | 2/2004 | Jansen et al. | |
| 2004/0116816 A1 | 6/2004 | Tenerz et al. | |
| 2004/0122421 A1 | 6/2004 | Wood | |
| 2004/0220562 A1 | 11/2004 | Garabedian et al. | |
| 2004/0230131 A1 | 11/2004 | Kassab et al. | |
| 2004/0243116 A1 | 12/2004 | Joye et al. | |
| 2004/0254495 A1 | 12/2004 | Mabary et al. | |
| 2005/0010110 A1 | 1/2005 | Black et al. | |
| 2005/0096647 A1 | 5/2005 | Steinke et al. | |
| 2005/0119647 A1 | 6/2005 | He et al. | |
| 2005/0240147 A1 | 10/2005 | Makower et al. | |
| 2005/0256521 A1 | 11/2005 | Kozel | |
| 2006/0009759 A1 | 1/2006 | Christian et al. | |
| 2006/0116633 A1 | 6/2006 | Shachar | |
| 2006/0149166 A1 | 7/2006 | Zvuloni | |
| 2006/0173251 A1 | 8/2006 | Govari et al. | |
| 2006/0206106 A1 | 9/2006 | Scholl et al. | |
| 2007/0016007 A1 | 1/2007 | Govari et al. | |
| 2007/0016069 A1 | 1/2007 | Grunwald et al. | |
| 2007/0016070 A1 | 1/2007 | Grunwald et al. | |
| 2007/0016072 A1 | 1/2007 | Grunwald et al. | |
| 2007/0062547 A1 | 3/2007 | Pappone | |
| 2007/0083194 A1 | 4/2007 | Kunis et al. | |
| 2007/0161914 A1 | 7/2007 | Zdeblick et al. | |
| 2007/0232896 A1 | 10/2007 | Gilboa et al. | |
| 2007/0255270 A1 | 11/2007 | Carney | |
| 2008/0004652 A1 | 1/2008 | Abboud et al. | |
| 2008/0033316 A1 | 2/2008 | Kassab et al. | |
| 2008/0033350 A1 | 2/2008 | Wilson et al. | |
| 2008/0176271 A1 | 7/2008 | Silver et al. | |
| 2008/0188830 A1 | 8/2008 | Rosenblatt et al. | |
| 2008/0190438 A1 | 8/2008 | Harlev et al. | |
| 2008/0194996 A1 | 8/2008 | Kassab | |
| 2008/0255475 A1 * | 10/2008 | Kondrosky | A61M 25/09 600/585 |
| 2008/0269581 A1 | 10/2008 | Wood et al. | |
| 2008/0269611 A1 | 10/2008 | Pedrizzetti et al. | |
| 2008/0294041 A1 | 11/2008 | Kassab | |
| 2008/0319350 A1 | 12/2008 | Wallace et al. | |
| 2009/0005674 A1 | 1/2009 | Saadat et al. | |
| 2009/0005675 A1 | 1/2009 | Grunwald et al. | |
| 2009/0062664 A1 | 3/2009 | Chang et al. | |
| 2009/0062684 A1 | 3/2009 | Gregersen et al. | |
| 2009/0118612 A1 | 5/2009 | Grunwald et al. | |
| 2009/0118637 A1 | 5/2009 | Kassab et al. | |
| 2009/0143640 A1 | 6/2009 | Saadat et al. | |
| 2009/0177090 A1 | 7/2009 | Grunwald et al. | |
| 2009/0182287 A1 | 7/2009 | Kassab | |
| 2009/0209872 A1 | 8/2009 | Pop | |
| 2009/0209950 A1 | 8/2009 | Starksen | |
| 2009/0216133 A1 | 8/2009 | Kassab | |
| 2009/0259124 A1 * | 10/2009 | Rothenberg | A61B 5/0422 600/424 |
| 2009/0262982 A1 * | 10/2009 | Markowitz | A61B 5/0422 382/103 |
| 2009/0262992 A1 * | 10/2009 | Markowitz | A61B 5/0422 382/128 |
| 2009/0264778 A1 | 10/2009 | Markowitz et al. | |
| 2009/0270729 A1 | 10/2009 | Corbucci et al. | |
| 2009/0270746 A1 | 10/2009 | Min | |
| 2010/0010355 A1 | 1/2010 | Kassab | |
| 2010/0010612 A1 | 1/2010 | Gelbart et al. | |
| 2010/0036227 A1 | 2/2010 | Cox et al. | |
| 2010/0041984 A1 | 2/2010 | Shapland et al. | |
| 2010/0049062 A1 | 2/2010 | Ziv | |
| 2010/0076328 A1 | 3/2010 | Matsumura et al. | |
| 2010/0198346 A1 | 8/2010 | Keogh et al. | |
| 2010/0210938 A1 | 8/2010 | Verard et al. | |
| 2010/0222786 A1 | 9/2010 | Kassab | |
| 2010/0268059 A1 | 10/2010 | Ryu et al. | |
| 2010/0291521 A1 | 11/2010 | Simon | |
| 2011/0015533 A1 * | 1/2011 | Cox | A61B 5/042 600/509 |
| 2011/0034823 A1 | 2/2011 | Gelbart et al. | |
| 2011/0196255 A1 | 8/2011 | Kassab | |
| 2011/0245662 A1 | 10/2011 | Eggers et al. | |
| 2011/0270237 A1 | 11/2011 | Werneth et al. | |
| 2011/0306867 A1 | 12/2011 | Gopinathan et al. | |
| 2012/0053441 A1 | 3/2012 | Kassab | |
| 2012/0059249 A1 | 3/2012 | Verard et al. | |
| 2012/0071782 A1 | 3/2012 | Patil et al. | |
| 2012/0078342 A1 * | 3/2012 | Vollkron | A61B 5/0538 623/1.11 |
| 2012/0108950 A1 * | 5/2012 | He | A61B 5/068 600/411 |
| 2012/0136242 A1 | 5/2012 | Qi et al. | |
| 2012/0143029 A1 | 6/2012 | Silverstein et al. | |
| 2012/0143078 A1 | 6/2012 | Kassab et al. | |
| 2012/0169712 A1 | 7/2012 | Hill et al. | |
| 2012/0172746 A1 | 7/2012 | Kassab | |
| 2012/0226148 A1 | 9/2012 | Jaggi et al. | |
| 2012/0302869 A1 | 11/2012 | Koyrakh et al. | |
| 2013/0041269 A1 | 2/2013 | Stahmann et al. | |
| 2013/0267835 A1 | 10/2013 | Edwards | |
| 2013/0338468 A1 | 12/2013 | Kassab | |
| 2014/0066738 A1 | 3/2014 | Kassab | |
| 2015/0297113 A1 | 10/2015 | Kassab et al. | |
| 2017/0071501 A1 | 3/2017 | Kassab | |
| 2019/0110844 A1 | 4/2019 | Misener et al. | |
| 2019/0133489 A1 | 5/2019 | Kassab | |

FOREIGN PATENT DOCUMENTS

| | | |
|---|---|---|
| EP | 0596344 A1 | 5/1994 |
| EP | 0786266 A1 | 7/1997 |
| EP | 0988827 A1 | 3/2000 |
| EP | 1025805 A1 | 8/2000 |
| EP | 2061532 A1 | 5/2009 |
| EP | 2134403 A2 | 12/2009 |
| WO | 1998035611 A1 | 8/1998 |
| WO | 2002019905 A1 | 3/2002 |

(56) References Cited

FOREIGN PATENT DOCUMENTS

| | | | |
|---|---|---|---|
| WO | 2002085442 A1 | 10/2002 | |
| WO | 2003092495 A1 | 11/2003 | |
| WO | 2004004828 A2 | 1/2004 | |
| WO | 2004075928 A2 | 9/2004 | |
| WO | 2006005985 A1 | 1/2006 | |
| WO | 2007015239 A2 | 2/2007 | |
| WO | 2008000833 A1 | 1/2008 | |
| WO | 2008031821 A1 | 3/2008 | |
| WO | 2008126074 A2 | 10/2008 | |
| WO | 2009003138 A1 | 12/2008 | |
| WO | 2010124169 A1 | 10/2010 | |
| WO | 2010130723 A1 | 11/2010 | |
| WO | 2011023911 A1 | 3/2011 | |
| WO | 2011024961 A1 | 3/2011 | |
| WO | 2011026337 A1 | 3/2011 | |
| WO | 2012110955 A1 | 8/2012 | |
| WO | 2012173697 A1 | 12/2012 | |
| WO | 2013/152335 A1 | 10/2013 | |
| WO | 2016/040394 A1 | 3/2016 | |

OTHER PUBLICATIONS

Douglas A. Hettrick, et al. "Finite Element Model Determination of . . . " Annals of Biomedical Engineering. vol. 27, pp. 151-159, 1999.
Douglas A. Hettrick, et al. "In Vivo Measurement of Real-Time Aortic Segmental Volume . . . " Annals of Biomedical Engineering. vol. 26, pp. 431-440, 1998.
Hoekstein and Inbar, "Cardiac Stroke Volume Estimation . . . " Technion Department of Electrical Engineering Publication EE PUB No. 991, Feb. 1994.
International Searching Authority, International Preliminary Report on Patentability, PCT/US1 0/32178, dated Nov. 3, 2011.
International Searching Authority, PCT Search Report and Written Opinion, PCT/US04/04828, dated Jul. 6, 2005.
International Searching Authority, PCT Search Report and Written Opinion, PCT/US06/05985, dated Aug. 8, 2007.
International Searching Authority, PCT Search Report and Written Opinion, PCT/US11/23911, dated Apr. 4, 2011.
International Searching Authority, PCT Search Report and Written Opinion, PCT/US11/24961, dated Aug. 30, 2012.
International Searching Authority, PCT Search Report and Written Opinion, PCT/US11/26337, dated Sep. 7, 2012.
L. Kornet, et al. "Conductance Method for the Measurement of . . . " Annals of Biomedical Engineering, vol. 27. pp. 141-150, 1999.
PCT/US07/15239 filed Jun. 29, 2007 International Search Report dated Jun. 5, 2008.
PCT/US2008/000833 filed Jan. 23, 2008 International Search Report dated Nov. 6, 2008.
PCT/US2013/035527 filed Apr. 5, 2013 International Preliminary Report on Patentability dated Oct. 16, 2014.
Supplementary European Search Report for EP Application Serial No. 04 71 2383 to Electro-Cat, LLC, dated Aug. 6, 2007.
Svendsen, Mark C. et al., "Accurate nonfluoroscopic guidance and tip location of peripherally inserted central catheters using a conductance guidewire system," Journal of Vascular Surgery: Venous and Lymphatic Disorders, vol. 1, Issue 2, pp. 202-208.
U.S. Appl. No. 14/010,139, filed Aug. 26, 2013 Non-Final Office Action dated Mar. 26, 2015.
CN 201380018999.6 filed Oct. 8, 2014 First Office Action dated Feb. 14, 2016.
EP 13772981.0 filed Apr. 5, 2013 Extended European Search Report dated Oct. 14, 2015.
PCT/US2015/049043 filed Sep. 8, 2015 International Search Report and Written Opinion dated Feb. 1, 2016.
U.S. Appl. No. 14/010,139, filed Aug. 26, 2013 Advisory Action dated Oct. 29, 2015.
U.S. Appl. No. 14/010,139, filed Aug. 26, 2013 Final Office Action dated Aug. 20, 2015.
U.S. Appl. No. 14/010,139, filed Aug. 26, 2013 Non-Final Office Action dated Dec. 15, 2015.
U.S. Appl. No. 14/010,169, filed Aug. 26, 2013 Final Office Action dated Mar. 22, 2016.
U.S. Appl. No. 14/010,169, filed Aug. 26, 2013 Non-Final Office Action dated Dec. 7, 2015.
U.S. Appl. No. 14/010,202, filed Aug. 26, 2013 Non-Final Office Action dated Apr. 15, 2016.
U.S. Appl. No. 14/010,202, filed Aug. 26, 2013 Non-Final Office Action dated Jan. 13, 2016.
CN 201380018999.6 filed Oct. 8, 2014 Office Action dated Aug. 30, 2016.
U.S. Appl. No. 14/010,169, filed Aug. 26, 2013 Non-Final Office Action dated Aug. 18, 2016.
U.S. Appl. No. 14/010,202, filed Aug. 26, 2013 Advisory Action dated Oct. 12, 2016.
U.S. Appl. No. 14/010,202, filed Aug. 26, 2013 Final Office Action dated Jul. 26, 2016.
CO 14.244.362 filed Nov. 5, 2016 Office Action dated Nov. 7, 2016.
U.S. Appl. No. 14/010,139, filed Aug. 26, 2013 Notice of Allowance dated May 20, 2016.
U.S. Appl. No. 14/010,169, filed Aug. 26, 2013 Advisory Action dated Jun. 7, 2016.
AU 2013243252 filed Aug. 13, 2014 Examination Report dated Nov. 9, 2016.
AU 2013243252 filed Aug. 13, 2014 Notice of Acceptance dated Mar. 23, 2017.
CO 14.244.362 filed Nov. 5, 2016 Office Action dated Jan. 23, 2017.
MX/a/2014/011884 filed Oct. 1, 2014 Office Action dated Jan. 30, 2017.
U.S. Appl. No. 14/010,169, filed Aug. 26, 2013 Advisory Action dated Jan. 25, 2017.
U.S. Appl. No. 14/010,169, filed Aug. 26, 2013 Final Office Action dated Nov. 17, 2016.
U.S. Appl. No. 14/010,202, filed Aug. 26, 2013 Final Office Action dated Mar. 29, 2017.
U.S. Appl. No. 14/010,202, filed Aug. 26, 2013 Non-Final Office Action dated Dec. 15, 2016.
U.S. Appl. No. 14/752,697, filed Jun. 26, 2015 Non-Final Office Action dated Feb. 7, 2017.
CN 201380018999.6 filed Oct. 8, 2014 Office Action dated Mar. 30, 2017.
U.S. Appl. No. 14/010,169, filed Aug. 26, 2013 Non-Final Office Action dated Jul. 7, 2017.
U.S. Appl. No. 14/010,202, filed Aug. 26, 2013 Advisory Action dated Jun. 20, 2017.
U.S. Appl. No. 14/752,697, filed Jun. 26, 2015 Final Office Action dated Jul. 21, 2017.
CO 14244362 filed Nov. 5, 2016 Office Action dated Feb. 5, 2018.
MX/a/2014/011884 filed Oct. 1, 2014 Office Action dated Feb. 20, 2018.
MX/a/2014/011884 filed Oct. 1, 2014 Office Action dated Oct. 3, 2017.
U.S. Appl. No. 14/010,169, filed Aug. 26, 2013 Advisory Action dated Feb. 28, 2018.
U.S. Appl. No. 14/010,169, filed Aug. 26, 2013 Advisory Action dated Jan. 17, 2018.
U.S. Appl. No. 14/010,169, filed Aug. 26, 2013 Final Office Action dated Oct. 30, 2017.
U.S. Appl. No. 14/010,202, filed Aug. 26, 2013 Non-Final Office Action dated Dec. 29, 2017.
U.S. Appl. No. 14/752,697, filed Jun. 26, 2015 Advisory Action dated Oct. 6, 2017.
U.S. Appl. No. 14/752,697, filed Jun. 26, 2015 Non-Final Office Action dated Jan. 31, 2018.
U.S. Appl. No. 14/848,331, filed Sep. 8, 2015 Restriction Requirement dated Nov. 22, 2017.
U.S. Appl. No. 14/752,697, filed Jun. 26, 2015 Advisory Action dated Oct. 9, 2018.
U.S. Appl. No. 14/752,697, filed Jun. 26, 2015 Final Office Action dated Jul. 24, 2018.
U.S. Appl. No. 14/848,331, filed Sep. 8, 2015 Non-Final Office Action dated Feb. 6, 2018.
U.S. Appl. No. 14/848,331, filed Sep. 8, 2015 Notice of Allowance dated Aug. 1, 2018.

(56) References Cited

OTHER PUBLICATIONS

U.S. Appl. No. 14/010,202, filed Aug. 26, 2013 Notice of Allowance dated May 15, 2019.
U.S. Appl. No. 14/752,697, filed Jun. 26, 2015 Non-Final Office Action dated Mar. 12, 2019.
U.S. Appl. No. 15/269,767, filed Sep. 19, 2016 Non-Final Office Action dated Mar. 13, 2019.

* cited by examiner

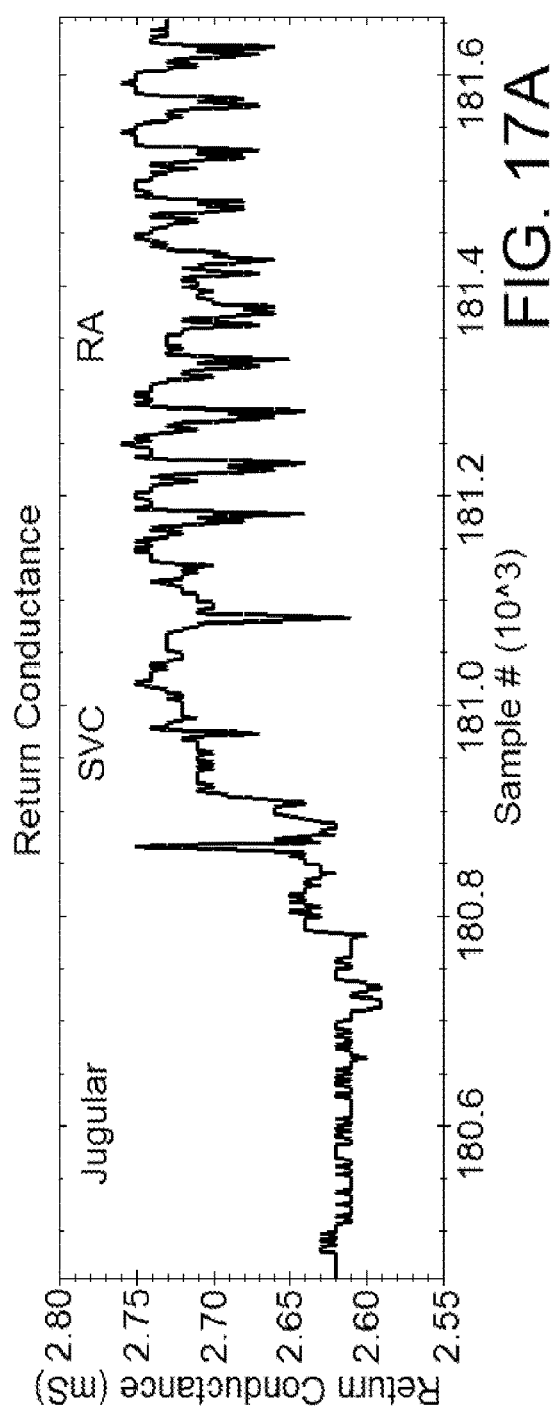
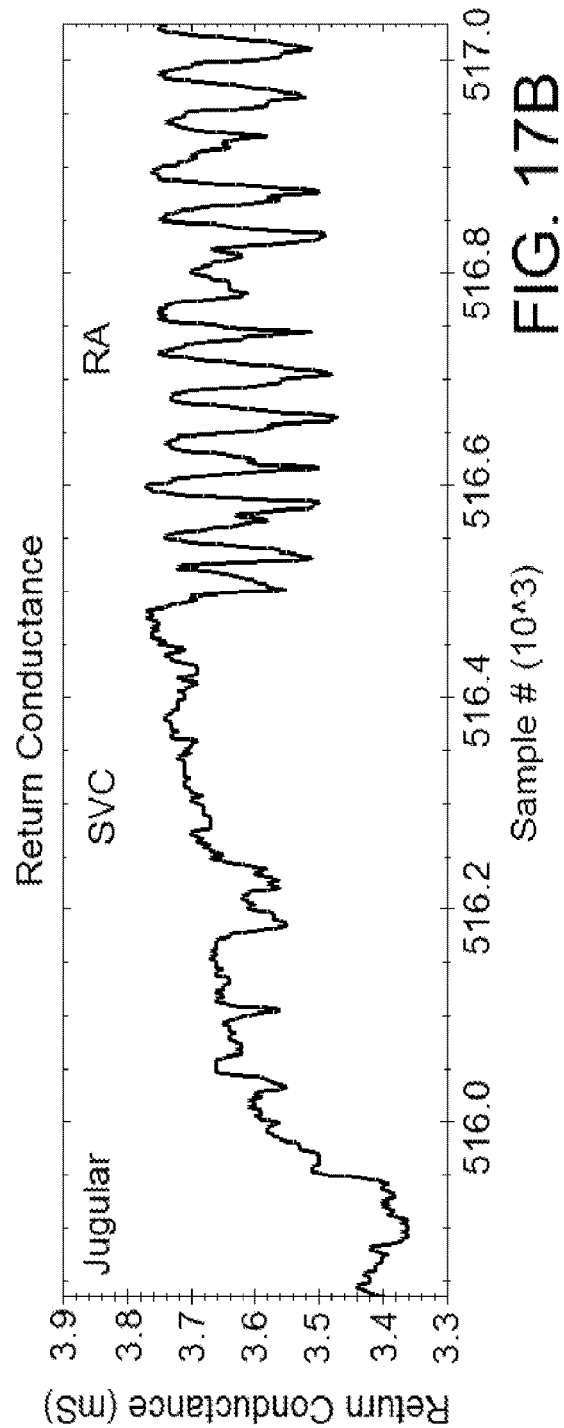
FIG. 17A
FIG. 17B

Post-Mortem Confirmation of Catheter Delivery to RA Using Impedance Guidance

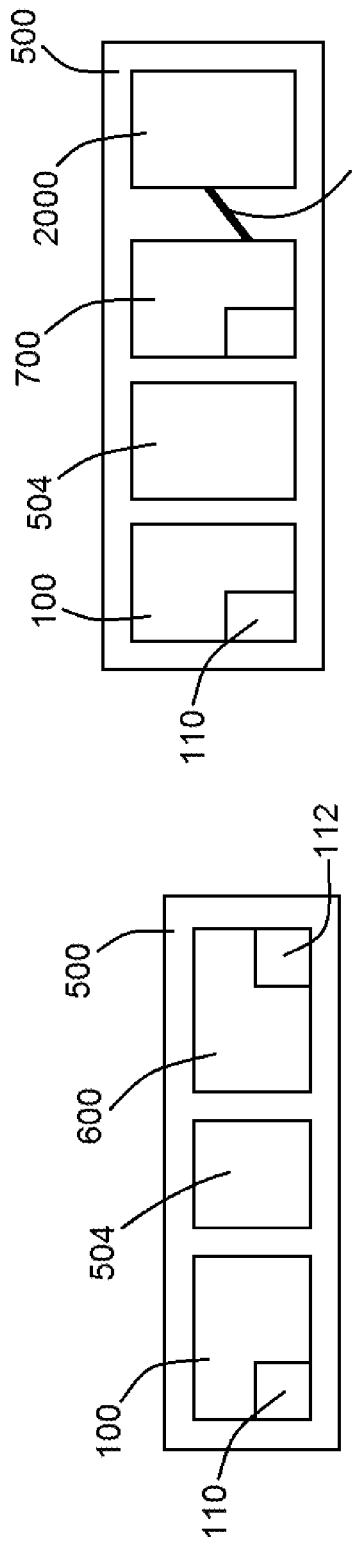
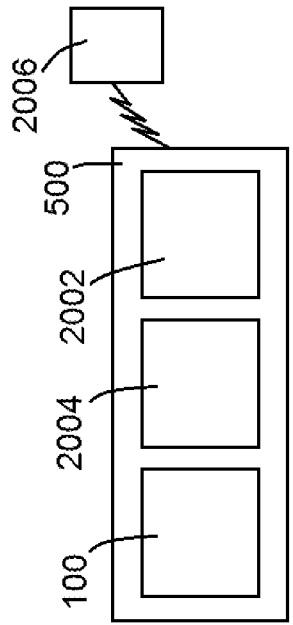
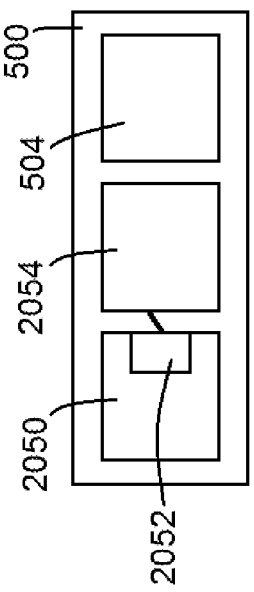
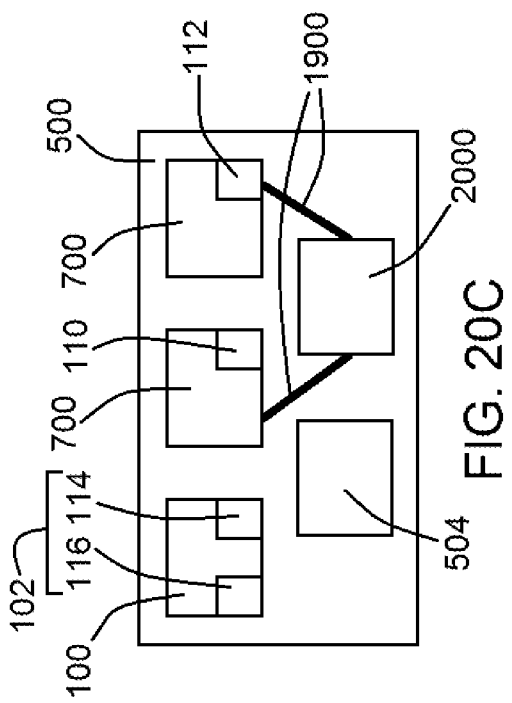

DEVICES AND SYSTEMS FOR NAVIGATION AND POSITIONING A CENTRAL VENOUS CATHETER WITHIN A PATIENT

PRIORITY

This application is a U.S. national stage application under 35 U.S.C. § 371 of International Application No. PCT/US2013/035527, filed Apr. 5, 2013, claiming priority to U.S. Provisional Application No. 61/620,872, filed Apr. 5, 2012, and U.S. Provisional Application No. 61/776,655, filed Mar. 11, 2013, each of which is incorporated by reference in their entirety into this application.

BACKGROUND

Central venous catheters (CVCs), such as peripherally inserted central catheter (PICC) lines, are long term implants (i.e., several weeks to months) used for central venous access. PICCs are widely used in many applications including: administration of pain medication, antibiotic drug delivery, blood sampling, blood transfusions, chemotherapy, hydration, total parenteral nutrition, hemodialysis, and other long term fluid administration applications. The accurate placement of PICC lines is not trivial and generally requires patient informed consent and placement by a specialized team member, whose sole focus is on PICC line delivery. Placement of the lines can occur in various locations including the operating room, during radiological procedures, at bedside in the clinic, or at home.

Proper placement of the CVC is crucial for the long term safety of the patient as well as efficacy of the catheter. Improper placement can result in arrhythmias, cardiac tamponade (i.e. catheter perforation), catheter dysfunction (e.g. obstruction or breakage), catheter-related sepsis, mechanical phlebitis, or thrombosis. These complications result in added clinical time and cost and, if left unattended, can ultimately lead to patient death. The ideal location for the PICC line tip in the vasculature that will minimize the risk of these complications has been a topic of debate. Several locations such as the right atrium (RA), the cavoatrial junction, and the superior vena cava (SVC) have been recommended; however, the general consensus is that tip placement should occur in the lower one third of the SVC for safe and effective usage.

CVCs, including PICC lines, are traditionally inserted using general medical personnel feel, one or more x-rays of the patient, and potentially also using ultrasound and/or fluoroscopy. Such procedures are not only time intensive, but also cost intensive in connection with the various scans and x-rays, and the longer the duration of the procedure, the more discomfort to the patient. In addition, and should the CVC not be properly placed, any therapy delivered therethrough may not be properly delivered, and the CVC itself could cause complications if improperly advanced into the heart.

Although x-ray confirmation is highly recommended for CVC placement, there are certain limitations that can make it unfeasible and/or unreliable. In many situations, such as home-care, seriously-ill, or emergency care situations, fluoroscopic guidance may not even be possible. When fluoroscopy or x-ray is possible, there are certain patients (like the morbidly obese or patients with spinal implants) in which visualization of the heart and vasculature can be difficult and make CVC placement challenging. In addition, x-ray guidance is inaccurate because it relies on interpretation of a two-dimensional projection of a three-dimensional object (the heart and vasculature and the soft nature of the tissue). Among Radiologists, discrepancies in the interpreted location of catheter tip position for AP chest x-ray images has been shown to occur in 40% of the cases. Thus, several studies have attempted to help clinicians locate the correct spot for the CVC tip by correlating x-ray landmarks (e.g., the carina to cavoatrial distance) with more precise computed tomography (CT) or magnetic resonance imaging (MRI) images. However, these approaches demonstrated patient variability in the landmarks (i.e., almost a 3 cm patient to patient range in landmarks), and hence, have not been widely utilized in clinical practice.

Based on the inherent limitations of fluoroscopy and the FDA's desire to develop new methods to reduce the amount of radiation exposure for both the patient and the clinician, efforts have been made to develop new PICC line guidance technologies. These new methods have included the use of monitoring changes in electrocardiographic waveforms and/or Doppler flow patterns as well as echocardiography and stylet-aided magnetic guidance. All of these existing technologies have inherent limitations because they attempt to find anatomical positions based on physiological measurements (ECG, flow measurements, etc.). There is a need for an anatomically-based, non-fluoroscopic method for accurate PICC line delivery that will require little training, be cost effective, portable, and reliable across various patient populations.

Devices and methods of positioning PICC lines and other CVCs accurately and with less time and cost would be well received by medical personnel, such as, for example, a novel conductance guidewire (CGW) system that provides real-time, simple feedback to the clinician for accurate PICC line placement without the assistance of x-ray guidance.

BRIEF SUMMARY

In at least one exemplary embodiment of a device of the present disclosure, the device comprises an elongated body having a detector positioned thereon or therein and/or otherwise coupled thereto, the detector comprising a pair of detection electrodes positioned in between a pair of excitation electrodes, the detector is configured to generate an electric field and also to obtain multiple conductance measurements within the electric field as the detector is advanced through a patient's vasculature, wherein each of the multiple conductance measurements is indicative of a location of the detector within the patient's vasculature when the detector is positioned therein.

In at least one exemplary embodiment of a device of the present disclosure, the device comprises an elongated body having a detector positioned thereon or therein and/or otherwise coupled thereto, the detector comprising a first excitation electrode and configured to generate an electric field with a second excitation electrode located external to the device, the device further configured to obtain multiple conductance measurements within the electric field as the detector is advanced through a patient's vasculature, wherein each of the multiple conductance measurements is indicative of a location of the detector within the patient's vasculature when the detector is positioned therein. In various embodiments where one detection electrode is on the device and the other is not on the device (such as located on the patient's body, as referenced in various methods herein), the "detector" is not entirely on the device itself. In such embodiments, part of the detector is on the device, while another part is on or in the patient's body, for example. In another embodiment, the second excitation electrode is positioned upon or within a sheath. In yet another embodiment, the sheath is configured for placement within a patient's blood vessel underneath the skin, and wherein the device is configured for insertion into a patient through the sheath. In an additional embodiment, the second excitation electrode comprises a portion of an electrode pad configured for placement upon a patient, such as upon the patient's skin. In yet an additional embodiment, the first excitation electrode is further configured to obtain the multiple conductance measurements.

In at least one exemplary embodiment of a device of the present disclosure, the device comprises an elongated body having a detector positioned thereon or therein and/or otherwise coupled thereto, the detector comprising a pair of detection electrodes and configured to detect an electric field generated by a first excitation electrode and a second excitation electrode each located external to the device, the device further configured to obtain multiple conductance measurements within the electric field as the detector is advanced through a patient's vasculature, wherein each of the multiple conductance measurements is indicative of a location of the detector within the patient's vasculature when the detector is positioned therein. In an additional embodiment, the first excitation electrode is positioned upon or within a sheath. In yet an additional embodiment, the sheath is configured for placement within a blood vessel underneath the patient's skin, and wherein the device is configured for insertion into a patient through the sheath. In another embodiment, the second excitation electrode comprises a portion of an electrode pad configured for placement upon a patient, such as upon the patient's skin. In yet another embodiment, the first excitation electrode and the second excitation electrode each comprise a portion of an electrode pad configured for placement upon a patient, such as upon the patient's skin. In an additional embodiment, the detector comprises a portion of an atraumatic tip coupled to the device, or wherein the detector is positioned near and proximal to the atraumatic tip.

In at least one exemplary embodiment of a device of the present disclosure, the device comprises an elongated body having a detector positioned thereon or therein and/or otherwise coupled thereto, the detector comprising a first excitation electrode and a second excitation electrode, the detector configured to generate an electric field and also to obtain multiple conductance measurements within the electric field as the detector is advanced through a patient's vasculature, wherein each of the multiple conductance measurements is indicative of a location of the detector within the patient's vasculature when the detector is positioned therein. In another embodiment, the first excitation electrode and the second excitation electrode are each further configured to obtain the multiple conductance measurements.

In at least one exemplary embodiment of a device of the present disclosure, the device comprises an elongated body having a detector positioned thereon at or near a distal end of the elongated body, wherein the detector is configured to obtain multiple conductance measurements as the distal end of the elongated body is advanced through a patient's vasculature. In an additional embodiment, the elongated body is configured as and selected from the group consisting of a wire, an impedance wire, a guidewire, a catheter, an impedance catheter, a guide catheter, a stylet, a central venous catheter, and a peripherally inserted central catheter. In yet an additional embodiment, the detector comprises a pair of detection electrodes positioned in between a pair of excitation electrodes so that one excitation electrode is distal to the pair of detection electrodes and so that another excitation electrode is proximal to the pair of the detection electrodes. In another embodiment, the elongated body comprises a material selected from the group consisting of silicone, a non-silicone polycarbon, a metal, and stainless steel. In yet another embodiment, the elongated body has at least one lumen defined therethrough.

In at least one exemplary embodiment of a device of the present disclosure, the device further comprises a hub positioned at or near a proximal end of the elongated body, and one or more access ports coupled to the hub, the one or more access ports each having at least one access port lumen defined therethrough. In another embodiment, the device further comprises one or more clamps positioned relative to or coupled to the one or more access ports, the one or more clamps configured to control a flow of fluid through the one or more access ports. In yet another embodiment, the elongated body has indicia thereon. In an additional embodiment, the device further comprises one or more distal ports present at the distal end of the elongated body, wherein one or more lumens defined within the elongated body terminate at the one or more distal ports. In yet an additional embodiment, the device further comprises one or more body ports positioned along of the elongated body, the one or more body ports in communication with one or more lumens defined within the elongated body.

In at least one exemplary embodiment of a system of the present disclosure, the system comprises an exemplary device of the present disclosure, wherein the device is configured as a central venous catheter or a stylet, and a data acquisition and processing system coupled to the device.

In at least one exemplary embodiment of a system of the present disclosure, the system comprises an exemplary device of the present disclosure, wherein the device is configured as a stylet, a guidewire, or a guide catheter, a data acquisition and processing system coupled to the device, and a central venous catheter. In general, at least one exemplary embodiment of a system of the present disclosure comprises a CVC, a console, and an arrangement/variation of electrodes.

In at least one exemplary embodiment of a method of the present disclosure, the method comprises the steps of puncturing a patient's skin to access a blood vessel of the patient, delivering a guidewire through the puncture, advancing at least part of an exemplary device of the present disclosure having a detector positioned thereon over the guidewire and into the blood vessel, wherein the step of advancing is performed while obtaining one or more conductance measurements using the detector. In an additional embodiment, the step of advancing is continued as one or more values of the one or more conductance measurements increases. In yet an additional embodiment, the method further comprises the steps of retracting the at least part of the exemplary device in response to or in connection with a decrease in the one or more values of the one or more conductance measurements is identified, and re-advancing the at least part of the exemplary device in response to or in connection with an increase in the one or more values of the one or more conductance measurements. In another embodiment, the method further comprises the step of stopping advancement of at least part of the exemplary device when or after a dramatic increase in conductance is identified, and optionally retracting at least part of the exemplary device (if needed) to ultimately position the at least part of the exemplary device within the blood vessel.

In at least one exemplary embodiment of a method of the present disclosure, the method is performed to place the device configured as a peripherally inserted central catheter within the patient. In an additional embodiment, certain steps are performed to position a distal end of the device at or near a junction of a vena cava and an atrium of a patient. In yet an additional embodiment, the increase in conductance is indicative of the detector of the device being at or near a junction of a vena cava and an atrium of a patient.

In at least one exemplary embodiment of a method of the present disclosure, the method comprising the steps of puncturing a patient's skin to access a blood vessel of the patient, delivering at least part of an exemplary device of the present disclosure through the puncture, the device having a detector positioned thereon at or near the distal end of the device, advancing at least part of the device through the blood vessel, wherein the step of advancing is performed while obtaining one or more conductance measurements using the detector. In another embodiment, the step of advancing is continued as one or more values of the one or more conductance measurements increases. In yet another embodiment, the method further comprises the steps of retracting the at least part of the exemplary device in response to or in connection with a decrease in the one or more values of the one or more conductance measurements is identified, and re-advancing the at least part of the exemplary device in response to or in connection with an increase in the one or more values of the one or more conductance measurements. In an additional embodiment, the method further comprises the steps of stopping advancement of at least part of the exemplary device when or after a dramatic increase in conductance is identified, and retracting at least part of the exemplary device to ultimately position the at least part of the exemplary device within the blood vessel.

In at least one exemplary embodiment of a method of the present disclosure, certain steps are performed to position a distal end of the device at or near a junction of a vena cava and an atrium of a patient. In another embodiment, the device comprises a stylet or a peripherally inserted central catheter or another type of central venous catheter, and wherein the method is performed to place the same within the patient. In yet another embodiment, wherein the device is configured as a guidewire or guide catheter, and the method further comprises the step of advancing at least part of a central venous catheter (such as peripherally inserted central catheter) over the device while obtaining one or more conductance measurements using the detector.

In at least one exemplary method of the present disclosure, a stylet, wire, or a catheter is introduced into the patient's vasculature using venous puncture, with advancement of the same occurring simultaneously with advancement of the CVC or in advance of placing the CVC over the same if a wire is used, for example. The stylet, wire, or catheter would contain the arrangement of one or more electrodes (to perform the unipolar, bipolar, tripolar, or tetrapolar methods as referenced herein, for example), and to communicate conductance and/or voltage measurements to the console (data acquisition and processing system) to guide the user through the vasculature.

In at least one exemplary embodiment of a method of the present disclosure, the method further comprises the steps of stopping advancement of at least part of the central venous catheter (or other device of the present disclosure) when or after a dramatic decrease in conductance is identified, and retracting at least part of the central venous catheter to ultimately position the at least part of the peripherally inserted central catheter within the blood vessel. In an additional embodiment, the dramatic decrease in conductance is indicative of the central venous catheter being positioned around the detector. In yet an additional embodiment, the method further comprises the step of removing the device from the patient. In another embodiment, one or both of the device and/or the central venous catheter has/have indicia thereon, the indicia indicative of a location along the device and/or the central venous catheter.

In at least one exemplary embodiment of a system of the present disclosure, the system comprises an elongated body having a detector positioned thereon, the detector comprising a first pole, and a component comprising a second pole, wherein the component is not part of the elongated body, wherein when the elongated body is advanced through a patient's vasculature, voltage data indicative of the electric field generated by the first pole and the second pole can be obtained at different locations within the patient's vasculature, wherein the voltage data indicates a physical location of the first excitation electrode within the patient's vasculature or a relative size or size changes (cross-sectional area or diameter) of the patient's vasculature.

In at least one exemplary embodiment of a system of the present disclosure, the system comprises an elongated body having a detector positioned thereon or therein and/or otherwise coupled thereto, the detector comprising a first pole, a component comprising a second pole, wherein the component is not part of the elongated body, wherein the first pole is configured to generate an electric field with the second pole, and wherein the device is further configured to obtain multiple conductance measurements within the electric field as the first pole is advanced through a patient's vasculature, wherein each of the multiple conductance measurements is indicative of a location of the first pole within the patient's vasculature when the first pole is positioned therein. In another embodiment, the first pole comprises a first excitation electrode. In yet another embodiment, the second pole comprises a second excitation electrode positioned upon the component. In an additional embodiment, the component itself is the second pole. In yet an additional embodiment, the component comprises a sheath configured for insertion into a puncture aperture within the patient. In another embodiment, the sheath is further configured for insertion into the patient's vasculature. In an additional embodiment, the sheath is configured to receive at least a portion of the device therein. In yet an additional embodiment, when the elongated body is initially advanced through a patient's vasculature, the voltage changes with change in caliber of organ lumen. In yet another embodiment, when the elongated body is advanced from a basilic vein to an axillary vein within the patient's vasculature, the voltage data decreases, and an increase in electrical conductance (ratio of current over voltage drop) can be detected.

In at least one exemplary embodiment of a system of the present disclosure, when the elongated body is advanced from an axillary vein to a subclavian vein within the patient's vasculature, the voltage data decreases, and an increase in conductance can be detected. In another embodiment, when the elongated body is advanced from a subclavian vein to a brachiocephalic vein within the patient's vasculature, the voltage data decreases, and an increase in conductance can be detected. In yet another embodiment, when the elongated body is advanced from a brachiocephalic vein to a superior vena cava within the patient's vasculature, the voltage data decreases, and an increase in conductance can be detected. In an additional embodiment, when the elongated body is advanced from a superior vena cava within the patient's vasculature to a right atrium of a heart, the voltage data decreases (and an increase in conductance can be detected), and voltage change pulsatility is identified due to heart function.

In at least one exemplary embodiment of a system of the present disclosure, the component comprises a pad configured for external placement upon the patient. In an additional embodiment, the pad comprises an electrode patch. In yet an additional embodiment, the second pole comprises a second excitation electrode positioned upon the pad. In another embodiment, the pad itself is the second pole. In yet another embodiment, when the elongated body is initially advanced through a patient's vasculature toward a desired location and wherein when the pad is positioned at or near the desired location, the voltage data decreases as the first pole moves toward the second pole.

In at least one exemplary embodiment of a system of the present disclosure, when the elongated body is advanced through a patient's vasculature, the voltage data changes, indicating profile of the vasculature. In another embodiment, when the elongated body is advanced from a basilic vein to an axillary vein within the patient's vasculature and wherein when the pad is positioned adjacent to the patient's heart, the voltage data decreases. In yet another embodiment, when the elongated body is advanced from an axillary vein to a subclavian vein within the patient's vasculature and wherein when the pad is positioned adjacent to the patient's heart, the voltage data decreases. In an additional embodiment, when the elongated body is advanced from a subclavian vein to a brachiocephalic vein within the patient's vasculature and wherein when the pad is positioned adjacent to the patient's heart, the voltage data decreases. In yet an additional embodiment, when the elongated body is advanced from a brachiocephalic vein to a superior vena cava within the patient's vasculature and wherein when the pad is positioned adjacent to the patient's heart, the voltage data decreases.

In at least one exemplary embodiment of a system of the present disclosure, when the elongated body is advanced from a superior vena cava within the patient's vasculature to a right atrium of a heart and wherein when the pad is positioned adjacent to the patient's heart, the voltage data decreases and voltage change pulsatility is identified due to heart function. In an additional embodiment, the system further comprises a tubular body configured for advancement over the device. In yet an additional embodiment, the tubular body is selected from the group consisting of a stylet or a peripherally inserted central catheter or another type of central venous catheter. In another embodiment, when the tubular body is advanced over the device and wherein when a distal portion of the tubular body covers the first pole or one or more electrodes of a detector, the voltage data increases (due to a decrease in conductance), indicating the location of the distal portion of the tubular body within the patient.

In at least one exemplary embodiment of a device of the present disclosure, the device comprises an elongated body having a detector positioned thereon, the detector comprising a first pole positioned at or near a distal end of the elongated body and a second pole positioned away from the distal end of the elongated body, wherein when the elongated body is advanced through a patient's vasculature, voltage data indicative of the electric field generated by the first pole and the second pole can be obtained at different locations within the patient's vasculature, indicative of changes in vascular/cardiac dimensions. In at least one exemplary embodiment of a device of the present disclosure, the device comprises an elongated body having a detector positioned thereon or therein and/or otherwise coupled thereto, the detector comprising a first pole and a second pole, the detector configured to generate an electric field and also to obtain multiple conductance measurements within the electric field as the detector is advanced through a patient's vasculature, wherein each of the multiple conductance measurements is indicative of a location of the detector within the patient's vasculature when the detector is positioned therein. In an additional embodiment, when the elongated body is advanced within the patient's vasculature to a right atrium of a heart, an additional drop in voltage data is identified, indicating the presence of the first pole within the right atrium. In yet an additional embodiment, the device further comprises a tubular body configured for advancement over the device. In another embodiment, the tubular body is selected from the group consisting of a stylet, a peripherally inserted central catheter, and a central venous catheter.

In at least one exemplary embodiment of a device of the present disclosure, when the tubular body is advanced over the device and wherein when a distal portion of the tubular body covers the first pole or one or more electrodes of a detector, the voltage data increases (consistent with a sharp decrease in conductance), indicating the location of the distal portion of the tubular body within the patient.

In at least one exemplary embodiment of a system of the present disclosure, the system comprises a device comprising an elongated body having a detector positioned thereon, a first component comprising a first pole, wherein the first component does not comprise the elongated body, and a second component comprising a second pole, wherein the second component does not comprise the elongated body, wherein when the elongated body is advanced through a patient's vasculature and wherein when the first component and the second component are operably positioned upon the patient, voltage data indicative of the electric field generated by the first pole and the second pole can be obtained at different locations within the patient's vasculature by the detector, wherein the voltage data indicates a physical location of the detector within the patient's vasculature or a relative size or size changes (cross-sectional area or diameter) of the patient's vasculature.

In at least one exemplary embodiment of a system of the present disclosure, the system comprises a device comprising an elongated body having a detector positioned thereon or therein and/or otherwise coupled thereto, a first component comprising a first pole, wherein the first component does not comprise the elongated body, and a second component comprising a second pole, wherein the second component does not comprise the elongated body, wherein the detector comprises a pair of detection electrodes and is configured to detect an electric field generated by the first pole and the second pole, the device further configured to obtain multiple conductance measurements within the electric field as the detector is advanced through a patient's vasculature, wherein each of the multiple conductance measurements is indicative of a location of the detector within the patient's vasculature when the detector is positioned therein.

In at least one exemplary embodiment of a system of the present disclosure, the system comprises an elongated body having a detector positioned thereon, and a first component comprising a first pole and a second pole, wherein the first component does not comprise the elongated body, wherein when the elongated body is advanced through a patient's vasculature and wherein when the first component and the second component are operably positioned upon the patient, voltage data indicative of the electric field generated by the first pole and the second pole can be obtained at different locations within the patient's vasculature by the detector, wherein the voltage data indicates a physical location of the detector within the patient's vasculature or a relative size or size changes (cross-sectional area or diameter) of the patient's vasculature. In another embodiment, the first pole is positioned upon or within a sheath. In yet another embodiment, wherein the sheath is configured for placement within a blood vessel underneath the patient's skin, and wherein the device is configured for insertion into a patient through the sheath. In an additional embodiment, the second pole comprises a portion of an electrode pad configured for placement upon a patient, such as upon the patient's skin. In yet an additional embodiment, the first pole and the second pole each comprise a portion of an electrode pad configured for placement upon a patient, such as upon the patient's skin.

In at least one exemplary embodiment of a system of the present disclosure, the detector comprises a portion of an atraumatic tip coupled to the device, or wherein the detector is positioned near and proximal to the atraumatic tip. In an additional embodiment, the first pole comprises a first excitation electrode. In yet an additional embodiment, the second pole comprises a second excitation electrode. In another embodiment, the first component itself is the first pole. In yet another embodiment, the second component itself is the second pole.

In at least one exemplary embodiment of a system of the present disclosure, when the elongated body is initially advanced through a patient's vasculature, the voltage data decreases, and an increase in conductance can be detected, as the detector moves closer to the first pole and the second pole. In another embodiment, when the elongated body is advanced from a basilic vein to an axillary vein within the patient's vasculature, the voltage data decreases. In yet another embodiment, when the elongated body is advanced from an axillary vein to a subclavian vein within the patient's vasculature, the voltage data decreases, and an increase in conductance can be detected. In an additional embodiment, when the elongated body is advanced from a subclavian vein to a brachiocephalic vein within the patient's vasculature, the voltage data decreases. In yet an additional embodiment, when the elongated body is advanced from a brachiocephalic vein to a superior vena cava within the patient's vasculature, the voltage data decreases. Similarly, and while such a device embodiment is advanced from the jugular vein to the brachiocephalic vein to the superior vena cava and ultimately to the right atrium, for example, the voltage data decreases, and conductance data increases.

In at least one exemplary embodiment of a system of the present disclosure, when the elongated body is advanced from a superior vena cava within the patient's vasculature to a right atrium of a heart, the voltage data decreases and voltage change pulsatility is identified due to heart function. In an additional embodiment, the first component and the second component each comprise one or more pads configured for external placement upon the patient. In yet an additional embodiment, the pad comprises an electrode patch. In an additional embodiment, the system further comprises a tubular body configured for advancement over the device. In yet an additional embodiment, the tubular body is selected from the group consisting of a stylet, a peripherally inserted central catheter, and another type central venous catheter.

In at least one exemplary embodiment of a system of the present disclosure, when the tubular body is advanced over the device and wherein when a distal portion of the tubular body covers the detector, the voltage data increases (consistent with a sharp decrease in conductance), indicating the location of the distal portion of the tubular body within the patient.

In at least one exemplary embodiment of a system of the present disclosure, the system comprises an exemplary device of the present disclosure, a connector handle configured to operably connect to the exemplary device, and a console configured to operably connect to the connector handle and further configured to display voltage data obtained using the exemplary device.

In at least one exemplary embodiment of a system of the present disclosure, the system comprises an exemplary device of the present disclosure, a console configured to display voltage data obtained using the exemplary device, a first connector coupled to the console, and a second connector coupled to the first connector and the exemplary device, wherein conductance data obtained using the exemplary device can be transmitted through the second connector and the through the first connector to the console.

In at least one exemplary embodiment of a method of the present disclosure, the method comprises the steps of introducing a portion of an exemplary device of the present disclosure via percutaneous intravascular introduction, advancing the portion of the exemplary device through a patient's vasculature toward a heart so long as conductance measurements obtained by the exemplary device are generally constant and/or generally increasing, and ceasing advancement of the portion of the exemplary device when the conductance measurements indicate pulsatility due to heart function. In another embodiment, the step of ceasing advancement is further performed based upon an identified stepwise change in conductance at or near a time when the conductance measurements indicate pulsatility. In yet another embodiment, the step of ceasing advancement is further performed based upon an identified stepwise change in conductance when the conductance measurements indicate pulsatility. In an additional embodiment, the stepwise change in conductance in response to or in connection with pulsatility is indicative of advancement of the portion of the exemplary device to a superior vena cava or cavoatrial junction at the heart. In yet an additional embodiment, the method further comprises the step of stopping advancement of the portion of the exemplary device and retracting the same when the conductance measurements spike upward or downward or generally decrease.

In at least one exemplary embodiment of a method of the present disclosure, the spike upward or downward or general decrease in conductance is/are indicative of advancement of the portion of the exemplary device through the patient's vasculature in a direction other than directly to the heart.

In at least one exemplary embodiment of a method of the present disclosure, the method comprises the steps of introducing a portion of an exemplary device of the present disclosure via percutaneous intravascular introduction, advancing the portion of the exemplary device through a patient's vasculature toward a heart so long as conductance measurements obtained by the exemplary device are generally constant and/or generally increasing, and ceasing advancement of the portion of the exemplary device when the conductance measurements indicate pulsatility due to heart function. In an additional embodiment, the step of ceasing advancement is further performed based upon an identified stepwise change in conductance at or near a time when the conductance measurements indicate pulsatility. In yet an additional embodiment, the step of ceasing advancement is further performed based upon an identified stepwise change in conductance when the conductance measurements indicate pulsatility. In another embodiment, the stepwise change in conductance in response to or in connection with pulsatility is indicative of advancement of the portion of the exemplary device to a cavoatrial junction at the heart.

In at least one exemplary embodiment of a method of the present disclosure, the method further comprises the step of stopping advancement of the portion of the exemplary device and retracting the same when the conductance measurements spike upward or downward or generally decrease. In another embodiment, the spike upward or downward or general decrease in conductance is/are indicative of advancement of the portion of the exemplary device through the patient's vasculature in a direction other than directly to the heart.

In at least one exemplary embodiment of a method of the present disclosure, the method comprises the steps of advancing the portion of an exemplary device of the present disclosure through a patient's vasculature toward a heart so long as conductance measurements obtained by the exemplary device are generally constant and/or generally changing in an increasing or a decreasing fashion; and ceasing advancement of the portion of the exemplary device when the conductance measurements indicate pulsatility due to heart function.

In at least one exemplary embodiment of a system useful to perform a method of detection, the system comprises an exemplary device of the present disclosure having a first electrode thereon or therein, and a second item having a second electrode thereon or therein, the second item being separate from the device and positioned either within or upon a patient, wherein the system is configured so that a method of detection can be performed using the exemplary device and the second item. In another embodiment, the method of detection is a unipolar method of detection, wherein the first electrode comprises an electrode capable of exciting a field and detecting (obtaining data) within the field. In yet another embodiment, the system further comprises a third item having a third electrode thereon or therein, the third item being separate from the device and positioned either within or upon the patient; and wherein one of the second electrode or the third electrode comprises an excitation electrode, and wherein another of the second electrode or the third electrode comprises a detection electrode. In an additional embodiment, the method of detection is a bipolar method of detection, wherein the first electrode comprises an electrode capable of exciting a field, and wherein the device further comprises a third electrode capable of detecting (obtaining data) within the field. In yet an additional embodiment, the system further comprises a third item having a fourth electrode thereon or therein, the third item being separate from the device and positioned either within or upon the patient; and wherein one of the second electrode or the fourth electrode comprises an excitation electrode, and wherein another of the second electrode or the fourth electrode comprises a detection electrode. In various embodiments, the second item and optionally the third item, if listed, are each selected from the group consisting of a pad and a sheath.

In various embodiments of methods of the present disclosure, as referenced and/or otherwise listed herein, whereby one or more devices, sheaths, and/or pads may be used to obtain voltage data useful to identify caliber changes of vascular/cardiac portions and ultimately identify when a distal end of the one or more devices are positioned within a targeted location within a patient, such as a right atrium of a heart. In other embodiments, the methods further comprise the step of advancing a tubular body, such as a peripherally inserted central catheter or a central venous catheter, over the device to the targeted location.

The present disclosure includes disclosure of devices without insulation or with insulation removed in certain areas. The present disclosure also includes disclosure of systems having a guidewire positioned within a portion of a central venous catheter, whereby a distal portion of the guidewire extends from a distal end of the central venous catheter and is locked in place. The present disclosure further includes disclosure of systems using a balloon catheter and a central venous catheter, whereby inflation of a balloon catheter can indicate a position of the balloon catheter within a patient's vasculature.

The present disclosure includes disclosure of devices and systems whereby an impedance measuring circuit is included to provide one or more of audible, tactile, and/or visual feedback to an operator of said devices and systems. The present disclosure also includes disclosure of devices and systems for use with patients experiencing atrial fibrillation or other arrhythmia or irregular heartbeat. The present disclosure further includes disclosure of devices and systems useful within non-native patient vasculatures, said non-native patient vasculatures resulting from at least one surgical procedure.

The present disclosure includes disclosure of methods for repositioning a central venous catheter after initial placement of the central venous catheter within a patient's vasculature. The present disclosure also includes disclosure of methods of determining vessel perforation using an exemplary device or system of the present disclosure. The present disclosure further includes disclosure of systems using power line radiation to generate an electric field so that one or more conductance measurements within said field can be obtained using exemplary devices of the present disclosure. The present disclosure also includes disclosure of devices and systems providing audible feedback to an operator of the same. The present disclosure further includes disclosure of devices having at least one platinized tip operable as one pole in connection with a second pole, wherein the first pole and the second pole can generate an electric field so that one or more conductance measurements within said field can be obtained using exemplary devices of the present disclosure.

The present disclosure includes disclosure of a system, comprising a first pole and a second pole, the first pole and the second pole configured to generate an electric field within a mammalian body sufficient to obtain a plurality of field measurements therein, and an elongated body configured for at least partial insertion into a blood vessel of the mammalian body and advancement through a vasculature, said advancement dependent upon the plurality of field measurements indicative of one or more locations of a portion of the elongated body within the vasculature. The present disclosure includes disclosure of a method, comprising the steps of puncturing a patient's skin to access a blood vessel of the patient, advancing at least part of a system into the blood vessel, the system comprising a first pole and a second pole, the first pole and the second pole configured to generate an electric field within a mammalian body sufficient to obtain a plurality of field measurements therein, and an elongated body configured for at least partial insertion into a blood vessel of the mammalian body and advancement through a vasculature, said advancement dependent upon the plurality of field measurements indicative of one or more locations of a portion of the elongated body within the vasculature, wherein the step of advancing is performed while obtaining the plurality of field measurements.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 17A and 17B show additional conductance traces of a device to the right atrium from the jugular vein, according to exemplary embodiments of the present disclosure;

FIGS. 20A-20E show block diagrams of various system componentry, according to exemplary embodiments of the present disclosure;

Figure 1:
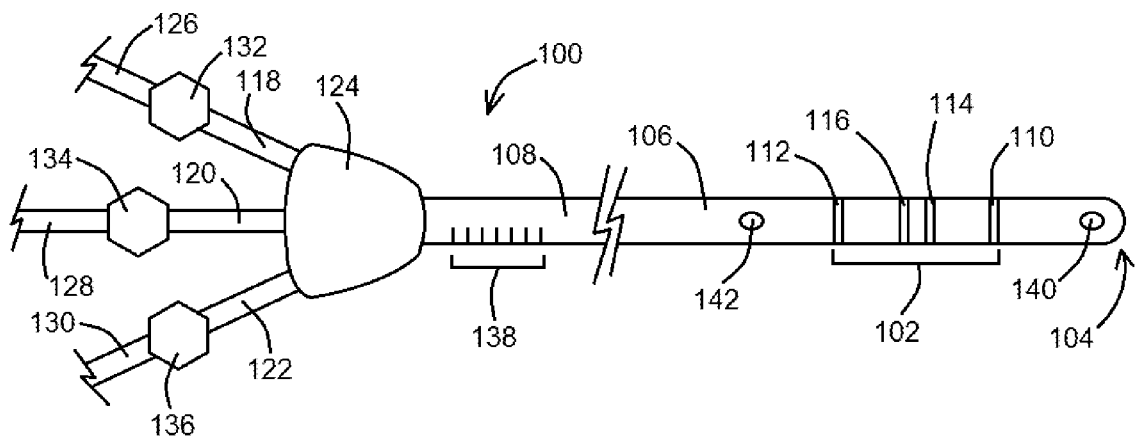
FIG. 1 shows a device configured as a peripherally inserted central catheter, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An exemplary device of the present disclosure is shown in FIG. 1. As shown in FIG. 1, and in at least one embodiment, device 100 comprises or is configured as a central venous catheter (CVC), such as, for example, a peripherally inserted central catheter (PICC or PICC line), with a detector 102 positioned at or near a distal end 104 of device 100. In such an embodiment, device 100 itself comprises an elongated body 106 that is made of a material that permits delivery of device 100 into a luminal organ (or an access route through another bodily part) of a patient and subsequent withdrawal from the patient without damaging the patient. As noted below, other device 100 embodiments may be configured as non-PICC or otherwise non-CVC line embodiments, such as guidewire or stylet embodiments, referenced in FIG. 3 and FIG. 5B for example and otherwise described herein. For example, elongated body 106 may comprise silicone or one or more other polycarbons so to prevent device 100 from "sticking" to the vasculature of the patient during or after insertion. In various device 100 embodiments of the present disclosure, configured as catheters or CVCs, for example, at least one lumen 108 would be defined within elongated body 106, and in various embodiments, elongated bodies 106 would define multiple lumens 108. In other embodiments (such as wire embodiments, for example), device 100 would not have a lumen therethrough.

Detector 102, as referenced herein, may refer to a tetrapolar arrangement of electrodes capable of generating an electric field and obtaining one or more conductance measurements in the presence of the field. For example, and as shown in FIG. 1, detector 102 may comprise a distal excitation electrode 110 and a proximal excitation electrode 112, with a distal detection electrode 114 and a proximal detection electrode 116 positioned therebetween along elongated body 106. The term "therebetween" is intended to imply that at least a portion of electrodes 114, 116 are physically distal to electrode 112 and proximal to electrode 110 along elongated body 106. The spacings between electrodes would vary depending on the size of the device 100 and the size of the luminal organ or access route where detector 102 would be delivered within the body. The conductance measurements, as referenced below, would be indicative of where some or all of detector 102 is positioned within the patient's body, and can be used to determine an appropriate delivery location of device 100. Detector 102, as referenced herein, would include at least one electrode capable of detection, such as detection electrodes 114, 116, or electrode 115, as shown in FIG. 19D, having detection functionality. Various other exemplary detectors 102 of the present disclosure may have more than one electrode, such as having two, three, four, five, or more electrodes.

As shown in FIG. 1, an exemplary device 100 of the present disclosure may have one or more access ports 118, 120, 122 connecting to a hub 124 positioned at or near a proximal end of the elongated body 106, whereby the lumens 126, 128, 130 defined within access ports 118, 120, 122, respectively, would be in communication with the one or more lumens 108 within elongated body 106. Various clamps/valves 132, 134, 136 may also be used in connection with access ports 118, 120, 122, respectively, to control the flow of fluid, for example, within said ports. In addition, indicia 138 may be positioned along elongated body 106, with indicia 138 indicating to a user of device 100 as to how much of device 100 is positioned within the patient's vasculature, for example, and potentially being indicative of a "hard stop" of advancement of device 100 based upon, for example, a general length of device 100 or a portion thereof advanced in view of indicia 138. Such indicia 138 may be distance markings and/or other indicia relating to a particular location along elongated body 106. Said indicia 138 may also allow cutting of a catheter and/or a CVC advanced over at least part of a device 100 to the defined length for implant, noting that a catheter or CVC may be cut regardless of indicia. In a device embodiment with one or more lumens 108 therethrough, one or more distal ports 140 may be present at the distal end 104 of device, and one or more body ports 142 may be positioned along elongated body 106, with one or more body ports 142 in communication with one or more lumens 108.

In general, a properly-delivered PICC line (an exemplary CVC) is delivered through a peripheral vein in a patient's arm (near the elbow joint) and advanced through the patient's vasculature until the distal end of the PICC line is positioned at or near the junction of the superior vena cava and the atrium. When positioned, various therapies (fluids, medicaments, etc.) can be delivered through the PICC line directly to the heart. Delivery of PICC lines is not limited to delivery through a patient's arm, as delivery through a patient's leg may also occur.

Traditional PICC line delivery includes an initial puncture of the patient's arm or leg, delivery of a guidewire through the puncture (or through a needle or cannula positioned at the puncture site), to provide initial access into the vasculature, and optionally for delivery of the PICC line over the guidewire. Different medical personnel may use different devices. For example, nurses may place a PICC line, using a stylet for insertion, while physicians may advance guidewires through the patient's vasculature. The person delivering the PICC line generally performs the delivery by feel, and when the person believes the PICC line is properly delivered, the patient receives an x-ray to determine the ultimate location of the PICC line in the patient's vasculature and where the PICC line terminates. If adjustment is needed (advancement, retraction, or re-delivery of the PICC line), the adjustment(s) is/are performed, and the patient receives one or more additional x-rays until the person delivering the PICC line is satisfied with its delivery. Ultrasound and/or fluoroscopy can be used during a traditional PICC line delivery as well, which, along with one or more x-rays, can contribute to the overall cost and time of the procedure and potential discomfort to the patient.

After proper PICC line delivery, and as referenced above, various therapies (fluids, medicaments, etc.) can be delivered through the PICC line directly to the heart. Improper PICC line delivery, such as when the distal end of the PICC line is positioned against a vena cava wall or too deep into the vena cava, can permit the endothelium to metabolize the injected drug. If the distal end of the PICC line is too deep into the atrium, the PICC line can scratch the wall of the atrium and potentially cause arrhythmia, or the heart itself can kink the PICC line, rendering it unsuitable for use. As such, proper PICC line delivery, and proper delivery of other types of CVCs, is critical for it to be used effectively.

The disclosure of the present application includes disclosure of a new method of delivering PICC lines and other CVCs that is not only effective, but less time consuming and does not require the use of x-ray, ultrasound, or fluoroscopy. Such a novel method is expected to be well-received in the medical profession given its benefits over traditional PICC line delivery and the costs and time to perform such traditional delivery. Furthermore, the cost advantages of various devices 100 of the present disclosure, especially those unipolar devices that use a stylet or guidewire as a pole, are significant.

Figure 2:
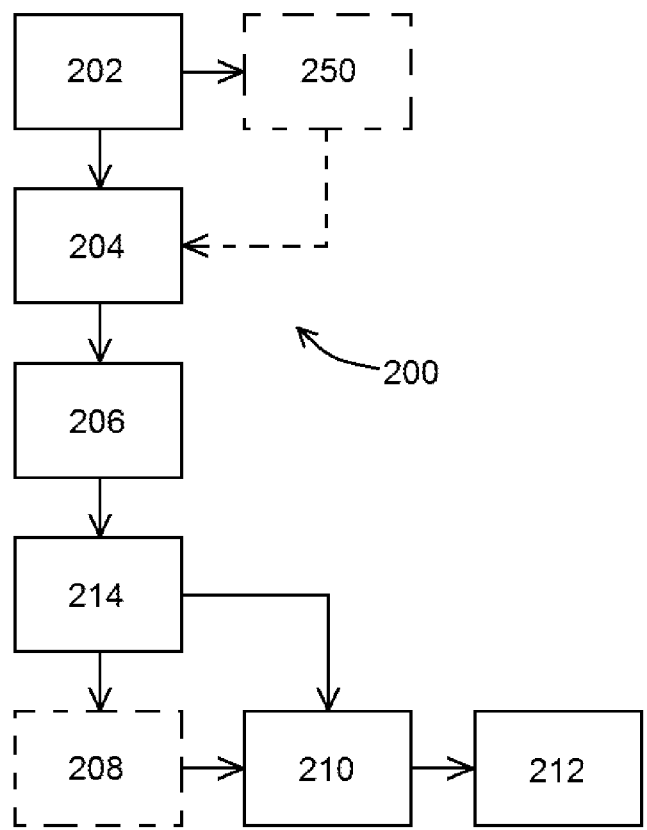
FIG. 2 shows a block diagram of steps of a method using a device of the present disclosure, according to an exemplary method embodiment of the present disclosure.

An exemplary method 200 of the present disclosure, as shown in the block diagram in FIG. 2, may be performed as follows. After initial skin puncture (an exemplary puncture step 202) to provide access to a blood vessel within a patient, a guidewire may be delivered through the puncture (an exemplary guidewire delivery step 204) to facilitate insertion of an exemplary device 100 of the present disclosure. The guidewire (which may be an 0.018" guidewire or a guidewire of different dimensions) would have a size that would not only allow a device 100 to be positioned around it, but also so that it can be effectively introduced into the patient through the puncture (or through a needle and/or cannula positioned within the puncture).

Method 200 also includes the step of advancing a device 100 of the present disclosure through the patient's vasculature (an exemplary device advancement step 206). Advancement step 206, in accordance with the present disclosure, is performed while one or more conductance measurements are obtained using the detector 102 during device 100 delivery. In general, the diameter or cross-sectional areas of the patient's vasculature from the vein in the patient's arm (starting at a vein such as the cephalic, brachial, basilica, or saphenous veins) increases as the distance from the elbow to the heart decreases. In a situation where a device 100 is advanced through a vessel having a generally uniform size (such as in vitro), a voltage change would not be so steep as one pole moves away from another, but in vivo, where vessel sizes change, a voltage change would be more steep, indicative of a vessel size change. Using detector 102 of device 100, conductance measurements within the vessel can be obtained during delivery, and a general increase in conductance during advancement is indicative that the distal end 104 of device 100 is in the appropriate vessel. Navigation of such devices 100 of the present disclosure, whether they be impedance PICC/CVC embodiments as described in connection with the present method, or impedance wire embodiments as described with the method depicted in FIG. 4, may generate various profiles and be used in connection with exemplary unipolar, bipolar, tripolar, or tetrapolar devices and methods as described in further detail herein.

Advancement can continue until one or more events occur. For example, and if conductance measurements decrease during advancement, such a decrease could be indicative of the distal end 104 of device 100 being positioned within an incorrect vessel. A side branch vessel leading away from the heart would decrease in size as the distance from the heart increases, and should the distal end 104 (near detector 102) enter such a side branch vessel, a decrease in conductance would be shown and the user could retract device 100 a desired distance and attempt to advance device 100 through the appropriate vessel. If the retraction and advancement results in a general increase in conductance, then the user can be confident that advancement of device 100 is proceeding as desired. Such a retraction and re-advancement, if performed during method 200, may be referred to herein as an exemplary retraction and re-advancement step 208. Furthermore, and should a veno stenosis or a vaso spasm exist during advancement of device 100, those items could affect the voltage or conductance readings, so those readings could be considered anomalies since they are transitions (decrease and then recover with advancement of device) as opposed to monotonic decrease (constant decrease towards a smaller branch). Conductance measurements/readings and voltage measurements/readings may be generally and collectively referred to herein as one or more "field measurements."

Another event may be a dramatic increase in conductance during advancement. Such a dramatic increase would be indicative of the juncture between the vena cava and the atrium, which would be the largest area within the vasculature during advancement up to that point. When the dramatic increase in conductance (coupled with pulsatility, for example) is shown, the user knows that the distal end 104 of device 100 is positioned at or near the desired location (such as at the right atrium, in the right atrium, at the superior vena cava-right atrium (SVC-RA) junction, or at/within the SVC), or that the distal end 104 of device 100 has passed the junction of the superior vena cava and the atrium and that advancement of device 100 needs to stop and device 100 may possibly need to be refracted so that the distal end 104 is at the SVC-RA junction, should the SVC-RA junction be the desired location. Such a retraction may be referred to as an exemplary junction retraction step 210. As conductance decreases during retraction to a level where the user identifies the distal end 104 as being at or near the junction, delivery of device 100 is completed. Final procedural steps, such as securing part of the device 100 to the patient's skin at or near the puncture (an exemplary securing step 212), for example, may also be performed. In addition, method 100 could include a guidewire withdrawal step 214, performed as desired during performance of an exemplary method 100. In at least one embodiment, and as shown in FIG. 2, guidewire withdrawal step 214 may be performed after advancement step 206.

As referenced above, a user uses changes in conductance values obtained by detector 102 to facilitate placement of device 100 within a patient's vasculature. Those conductance values may be relative conductances (with changes in conductance being relative to one another) that could be used to calculate relative changes in cross-sectional area, for example, as previously described in the art by inventor Kassab. Absolute cross-sectional areas may also be obtained using methods also previously described by Kassab.

Figure 3:
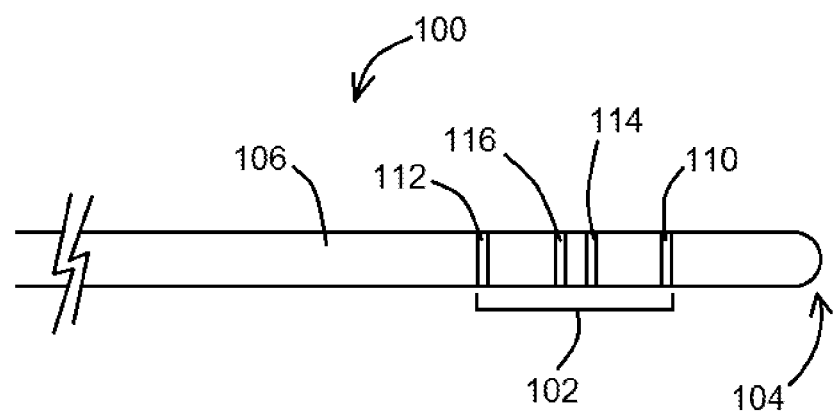
FIG. 3 shows a device configured as a stylet, a wire, or a catheter, according to an exemplary embodiment of the present disclosure.

The present disclosure also includes disclosure of various other device embodiments, such as the additional device 100 embodiment shown in FIG. 3. In such an embodiment, with a relative distal portion shown in FIG. 3, device 100 comprises an elongated body 106 configured as a guidewire (not as a CVC), whereby no lumen 108 is present therein. Elongated body 106 of device 100 would have a detector 102 present thereon, which may comprise the same tetrapolar arrangement of detection electrodes 114, 116 positioned within excitation electrodes 110, 112, or may comprise a detector having one, two, or three electrodes thereon, as described in further detail herein. An exemplary device 100 of the present disclosure may comprise a metallic guidewire without insulation, or with insulation removed in certain areas, so that device 100 would be conductive and useful as a CGW.

Figure 4:
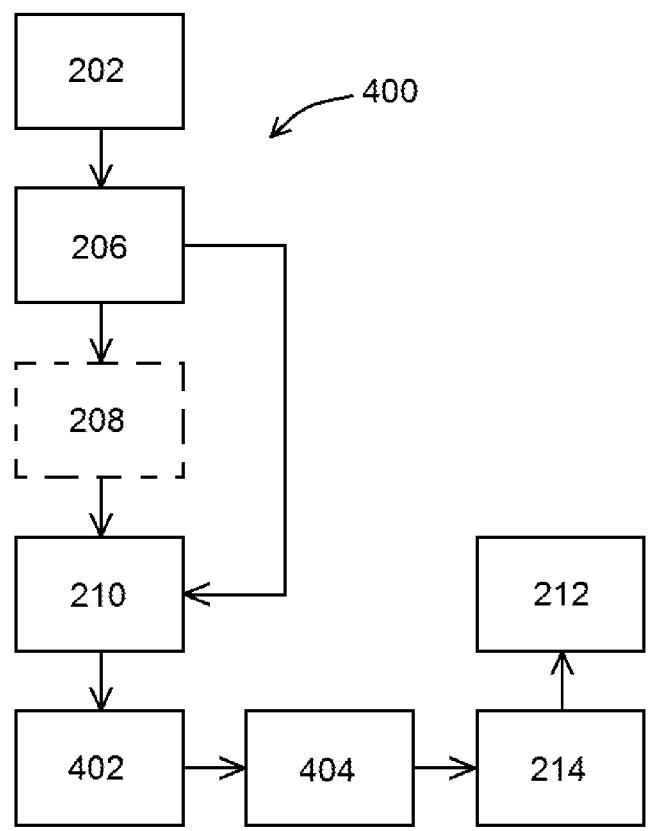
FIG. 4 shows a block diagram of steps of a method using a device of the present disclosure, according to an exemplary method embodiment of the present disclosure.

Such a device 100 embodiment, when used with a standard CVC such as a PICC line, would facilitate proper PICC line delivery as shown in the exemplary method 400 depicted in the block diagram of FIG. 4. As shown therein, method 400 comprises exemplary puncture steps 202 and an exemplary device advancement step 206, whereby the device 100 is a guidewire embodiment. Device advancement step 206 may be performed as previously described, with an optional exemplary retraction and re-advancement step 208 performed as needed. When a dramatic increase in conductance during advancement is identified (which is indicative of the juncture between the vena cava and the atrium, which would be the largest area within the vasculature during advancement up to that point), device 100 would be either remain at that location or optionally moved to a desired location distal or proximal to that location, and immobilized (performance of an exemplary securing step 212) so that the distal end 104 is at or near the SVC-RA junction.

At that point, device 100 (a guidewire embodiment) is positioned so that the detector 102 positioned thereon is positioned at or near the juncture between the vena cava and the atrium. Method 400, in at least one embodiment, would then comprise the step of advancing a PICC line or other CVC embodiment over device 100 (an exemplary PICC line advancement step 402). Step 402 would be performed while obtaining at least one conductance measurement using device 100. If a plurality of conductance measurements are obtained during performance of step 402, those conductance measurements should be relatively constant until a distal end of the PICC line is advanced to detector 102. When the distal end of the PICC line crosses detector 102 or a portion thereof, a dramatic decrease in conductance would be shown, which indicates to the person delivering the PICC line that the distal end of the PICC line is at or near the distal end of device 100 because of the decrease in conductance revealed by detector 102. PICC line 102 can then be retracted until the conductance increases, which would indicate placement of the distal end of the PICC line as being just proximal to detector 102 or a portion thereof. Such a retraction may be performed during an exemplary PICC line junction retraction step 404. At that point, the user is confident of the location of the distal end of the PICC line, and any minor adjustments may be made (as being relative to the position of device 100 in connection with steps 206 and/or 210) to the location of the PICC line. Method 400 would then include the step of withdrawing device 100 from the patient (an exemplary guidewire withdrawal step 214), and any other final procedural steps, such as securing part of the device 100 to the patient's skin at or near the puncture (an exemplary securing step 212), as desired.

As referenced above, the device embodiment 100 shown in FIG. 3 is described as being a guidewire embodiment. Such a device embodiment 100 may also be a guide catheter embodiment (having a detector 102 thereon, for example), noting that the guide catheter would need to be sufficiently small as to permit a PICC line to be advanced over the guide catheter.

With the various device 100 embodiments referenced herein, any number of wires and/or other connectors or componentry needed to connect the electrodes 110, 112, 114, and/or 116 to a console 902 or data acquisition and processing system 502 may be used.

Figure 5A:
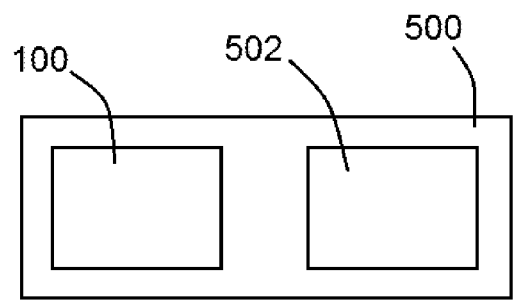
FIGS. 5A and 5B show systems, according to exemplary embodiments of the present disclosure.

An exemplary system 500 of the present disclosure is shown in block diagram form in FIG. 5A. As shown in FIG. 5A, an exemplary system 500 may comprise a device 100 and a data acquisition and processing system 502 (which may also be a console 902), whereby data obtained from the detector 102 of device 100 is transmitted to system 502 or console 902. Such a system 500 embodiment would comprise a device 100 configured as a PICC line or as another type of CVC.

Figure 5B:
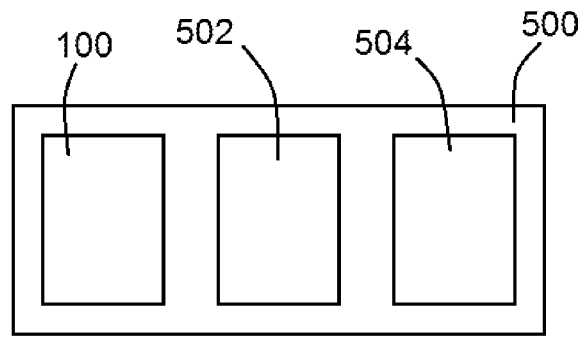

Another system embodiment 500 of the present disclosure is shown in FIG. 5B. As shown therein, an exemplary system 500 comprises a device 100, a CVC 504 (such as a PICC line, for example, or another type of CVC), and a data acquisition and processing system 502 (which may also be a console 902), whereby data obtained from the detector 102 of device 100 is transmitted to system 502 or console 902. In such an embodiment, device 100 is configured as a wire, stylet, or catheter with a detector 102 thereon, and CVC 504 does not have a detector 102 thereon.

In general, and as referenced herein, placement of a PICC line or another exemplary CVC would include an exemplary device 100 (which may also be part of an exemplary system 500), an operator of device 100, and a patient for which the device 100 would be inserted. Device 100 may be configured as the CVC 504, or may be used in connection with a CVC 504 or 2002.

As referenced herein, device 100 and/or CVC 504 insertion/advancement can be performed in connection with obtaining multiple conductance measurements. Such conductance measurements can be processed and/or displayed using data acquisition and processing system 502 or console 902 coupled to the device 100 with detector 102 thereon.

In addition to the foregoing, it may be desirable to a user of device 100 and/or system 500 to know the distance of insertion of device 100 and/or CVC 504 into a patient. This can be accomplished in several ways, including, but not limited to, (i) the use of an accelerometer (not shown), whereby two integrations of acceleration provides the distance, (ii) indicia 138 positioned on device 100 and/or CVC 504, (iii) a relatively constant push of device 100 and/or CVC 504 (such as, for example, 1 centimeter per 2 or 3 seconds), whereby tracking of time using system 502 or another device can provide the distance as a product of velocity and time, and/or (iv) a general knowledge of the length of device 100 and/or CVC 504 and how much of the same is inserted into the patient.

A user may also wish to be able to automatically detect "jumps" in geometry, such as through a gradient method (namely a calculation of slope over distance). Using the slope and the distance over which it occurs would allow for overall profiling of the vasculature during performance of one or more of methods 200 and/or 400 or other methods of the present disclosure.

Images from the profile can also be determined in accordance with the present disclosure. Unlike arteries, which are cylindrical, veins are elliptical. If conductance is used as being proportional to area ($\pi \times a \times b$, wherein a and b are the minor and major axes of an ellipse), it would result in an unconstrained problem of one equation with two unknowns (a and b). As the ratio of a to b tends to be fairly constant in the venous system, it would serve to provide an additional equation or relation to produce an ellipse from the knowledge of the area. As such, a data acquisition and processing system 502 or console 902 can produce/display ellipses as device 100 is advanced through the vasculature, as some practitioners prefer images to better conceptually "visualize" what is going on during the procedure. Since there is a physical limit on b (the major axis) of the vein (vena cava) of 2-3 cm, data acquisition and processing system 502 or console 902 can identify this when a large area (2 to 3 times the quantity of the atrium) is recorded, and therefore display the transition or junction between the vena cava and the atrium as desired.

In addition to the foregoing, alternative device 100 embodiments are also included within the present disclosure. As referenced herein, several device 100 embodiments comprise a detector 102 positioned thereon as the sole detection portion. However, additional embodiments of devices 100 and systems 500 of the present disclosure may comprise multi-part detector 102, whereby certain detector 102 components are positioned on device 100 (such as along elongated body 106), while other detector 102 components, or other componentry that can function/operate as a detector 102 component, are not positioned directly upon device 100.

Figure 6:
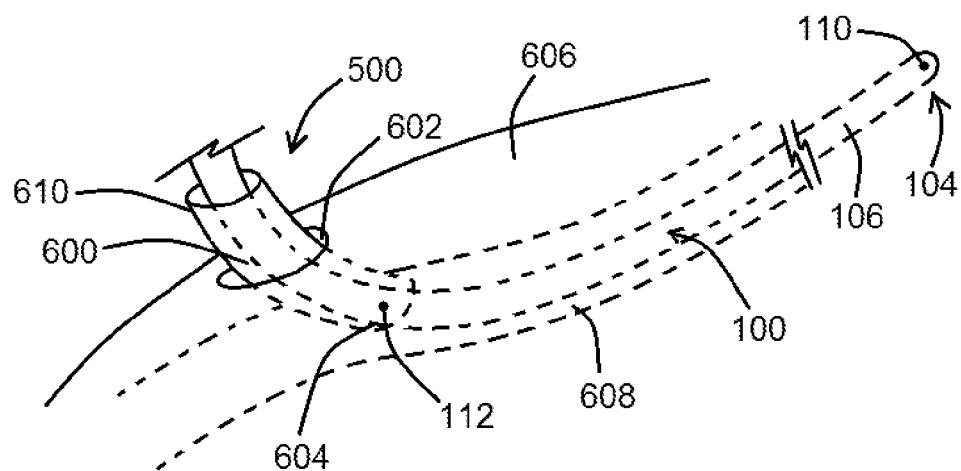
FIG. 6 shows a system comprising a device positioned within a sheath and inserted into a patient, according to an exemplary embodiment of the present disclosure; according to an exemplary embodiment of the present disclosure.

An exemplary embodiment of a system 500 of the present disclosure is shown in FIG. 6, with portions thereof positioned within a patient. As shown in FIG. 6, system 500 comprises an exemplary device 100 of the present disclosure and a sheath 600 (an exemplary device positioned within through a patient's skin and into the patient's vessel) configured to facilitate entry of a portion of another device such as device 100 into a patient. For example, an exemplary skin puncture step 202 may be followed by or include the step of inserting a sheath 600 into the puncture aperture 602 (an exemplary sheath insertion step 250, as shown in FIG. 2), whereby sheath 600 operates not only to maintain the puncture aperture 602 in an open state but also to allow a portion of device 100 to be inserted therethrough into the patient. In at least one embodiment, sheath insertion step 250 is performed so that a distal end 604 of sheath 600 is positioned through the patient's skin 606 and optionally also within a portion of the patient's vein 608, allowing a proximal end 610 of sheath 600 to remain external to the patient.

In such an embodiment, and in other embodiments of the present disclosure, one of the poles (electrodes, for example) is positioned on device 100 itself, while a second pole is positioned upon, or comprises part of, a second component of system 500. For example, and as shown in FIG. 6, one of the poles (such as a distal excitation electrode 110 or another electrode) may be positioned upon elongated body 106 of device 100, such as at or near a distal end 104 of a device 100 embodiment. A second pole (such as a proximal excitation electrode 112 or another electrode) may be positioned upon sheath 600, or sheath 600 itself may operate as the second pole, such as, for example, whereby sheath 600 at least partially comprises metal. In such a sheath 600 embodiment, and upon activation of distal excitation electrode 110 and proximal excitation electrode 112 (or sheath 600), for example, a voltage output would increase linearly (or at least partially linearly) as distal excitation electrode 110 is initially moved further away from the proximal excitation electrode 112, such as by initially advancing the distal end 104 of device 100 toward a region of interest within the patient (the right atrium, for example). Such an increase in voltage will be compounded by one or more sudden drops (decreases) in voltage as distal excitation electrode 110 passes by each vessel bifurcation, such as where the vessel becomes larger or as it transitions from the superior vena cava to the right atrium, for example. As there is a larger overall area at a bifurcation, there would be a general increase in conductance when using device 100 in this example, so voltage would decrease. However, as device 100 moves from one vessel to another larger vessel, for example, an initial drop/decrease would be detected, but an overall general and subsequent increase would be detected, consistent with an increasing sawtooth pattern.

Generally speaking, if a device 100 of the present disclosure has one pole/electrode thereon (a unipolar embodiment, as generally referenced herein), and device 100 is advanced toward the second pole (such as on a pad near the patient's heart), there will be a general decrease in voltage over time as device 100 is advanced through the vasculature toward the heart and toward the second pole near the heart. Conversely, if a device 100 of the present disclosure has one pole thereon, and device 100 is advanced away from the second pole (such as on the sheath at the point of entry of device 100 into the patient), there will be a general increase in voltage over time as device 100 is advanced through the vasculature toward the heart and away from the second pole on the sheath.

Furthermore, and in at least one embodiment of the present disclosure, two systems 500 are used, whereby two sheaths 600 are separately inserted into the body, and whereby one device 100 is advanced into each sheath. Data can then be obtained, as described above, for each system 500.

Phasic changes of voltage may also be observed when the distal excitation electrode 110 (or another pole/electrode used as a detector 102 or portion thereof) is in or near the right atrium due to the pulsatility of the heart. Pulsatility, as referenced herein, indicates changes in the size of the heart while the heart pumps. In at least one embodiment, devices 100 of the present disclosure are configured to detect pulsatility in the superior vena cava. In such an embodiment, a first pulsatility may be detected at the superior vena cava, and a second pulsatility may be detected at the right atrium, whereby the first pulsatility can indicate positioning of a distal end 104 of device 100 at or near the superior vena cava, while a second pulsatility can indicate positioning of a distal end 104 of device 100 at or near the right atrium. Accordingly, and as referenced above, the gradients of voltage and pulse changes (such as maxima to minima of phasic changes) can be used to determine the location of the distal end 104 of device 100 within the patient as generally referenced herein. As referenced herein, voltage measurements are identified as voltage differences measured using two poles (excitation electrodes). For example, advancement of the distal end 104 of device 100 within a patient's vein 608 to the right atrium, when using a distal excitation electrode 110 of device 100 as the first pole and proximal excitation electrode 112 on sheath 600 as the second pole, would cause a general increase in voltage over time during device 100 advancement, with drops in voltage at vein 608 bifurcations, and pulsatile voltage changes at or near the right atrium, indicating the location of distal end 104 of device 100 therein. In such an embodiment, an exemplary system 500 would comprise device 100 with distal excitation electrode 110, sheath 600 with proximal excitation electrode 112, and other components as needed/desired for operation. Such a system 500 embodiment would not require detection electrodes, such as distal detection electrode 114 and/or proximal detection electrode 116, as the two poles (such as distal excitation electrode 110 and proximal excitation electrode 112 referenced above) would serve an excitation and detection function, so that a field can be generated and a voltage drop/change can be detected as device 100 is advanced and/or retracted within the patient's vasculature, given that one pole is stationary or generally stationary (such as on sheath 600), while the other pole is positioned upon device 100 and therefore moves through the vasculature as device 100 moves through the vasculature.

Figure 7A:
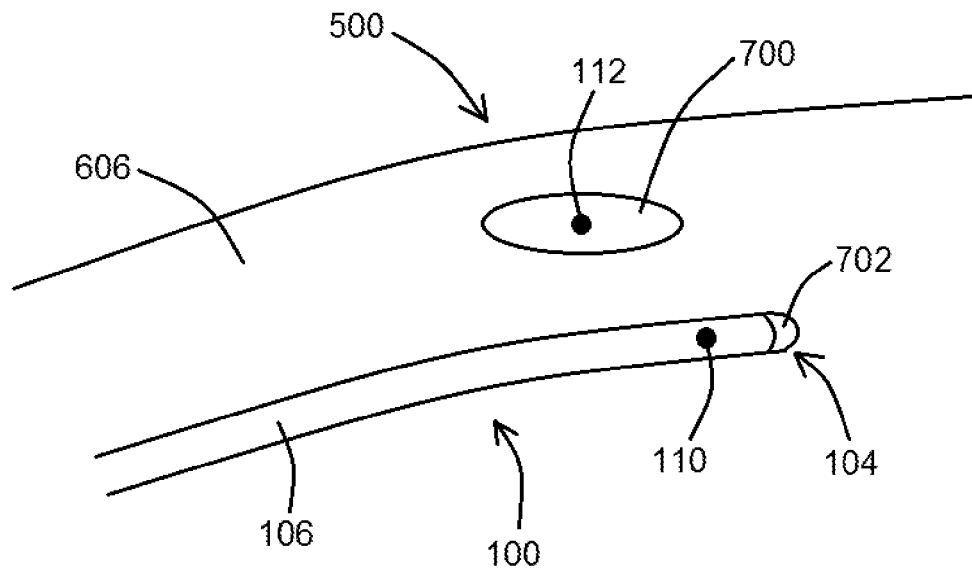
FIG. 7A shows a system comprising a device and a pad, according to an exemplary embodiment of the present disclosure.

An additional embodiment of a system 500 of the present disclosure is shown in FIG. 7A. As shown therein, one of the poles (such as a distal excitation electrode 110 or another electrode) may be positioned upon elongated body 106 of device 100, such as at or near a distal end 104 of a device 100 embodiment. Another pole (such as a proximal excitation electrode 112 or another electrode) may be positioned on an external surface of the patient, such as on the patient's chest or arm, approximately over the superior vena cava/right atrium region, or other area as desired, and may comprise part of an external pad 700, which may be, for example, an electrode patch. Alternatively, pad 700 may have componentry or features thereon so that pad 700 itself operates as the second pole without a separate proximal excitation electrode 112 positioned therein or thereon. In such a pad 700 embodiment, and upon activation of distal excitation electrode 110 of device 100 and proximal excitation electrode 112 upon pad 700, for example, a voltage output would initially decrease linearly (or at least partially linearly) as distal excitation electrode 110 is initially moved closer to proximal excitation electrode 112, such as by advancing the distal end 104 of device 100 toward a region of interest (the right atrium, for example) within the patient. Such a decrease in voltage will be compounded by one or more sudden drops in voltage as distal excitation electrode 110 passes by each vessel bifurcation, such as where the vessel becomes larger or as one transitions from the superior vena cava to the atrium, for example. Phasic changes of voltage may also be observed when the distal excitation electrode 110 is in or near the atrium due to the pulsatility of the heart (or pulsatility of the superior vena cava, for example).

Accordingly, and as referenced above, the gradients of voltage and pulse changes (such as maxima to minima of phasic changes) can be used to determine the location of the distal end 104 of device 100 within the patient using a system 500 embodiment as shown in FIG. 7A. For example, advancement of the distal end 104 of device 100 within a patient's vein 608 to the right atrium, when using a distal excitation electrode 110 of device 100 as the first pole and proximal excitation electrode 112 on pad 700, or just pad 700 itself, as the second pole, would cause a general decrease in voltage over time during device 100 advancement within the patient's vasculature, with drops in voltage at vein 608 bifurcations, and pulsatile voltage changes at or near the atrium, indicating the location of distal end 104 of device 100. In such an embodiment, an exemplary system 500 would comprise device 100 with distal excitation electrode 110, pad 700 with an optional proximal excitation electrode 112, and other components as needed/desired for operation. Such a system 500 embodiment would not require detection electrodes, such as distal detection electrode 114 and/or proximal detection electrode 116, as the two poles (such as distal excitation electrode 110 and proximal excitation electrode 112 referenced above) would serve an excitation and detection function, so that a field can be generated and a voltage drop/change can be detected as device 100 is advanced and/or retracted within the patient's vasculature, given that one pole is stationary or generally stationary (such as on pad 700), while the other pole is positioned upon device 100 and therefore moves through the vasculature as device 100 moves through the vasculature.

Figure 7B:
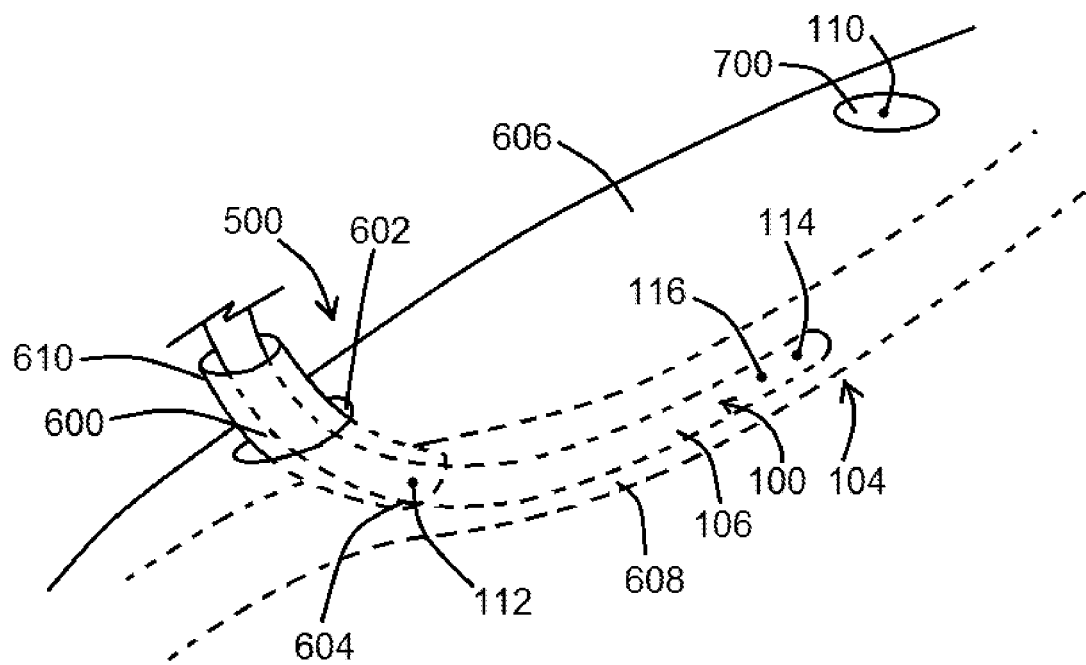
FIG. 7B shows a system comprising a device, a pad, and a sheath, according to an exemplary embodiment of the present disclosure.

Another embodiment of an exemplary system 500 of the present disclosure is shown in FIG. 7B. In such an embodiment, and in other embodiments of the present disclosure, none of the poles (electrodes, for example) are positioned on device 100 itself, but instead are positioned upon and/or comprise other portions of system 500. For example, and as shown in FIG. 7B, a first pole (such as a proximal excitation electrode 112) may be positioned upon sheath 600, or sheath 600 itself may operate as the first pole, such as, for example, whereby sheath 600 at least partially comprises metal. A second pole (such as a distal excitation electrode 110) may be positioned on an external surface of the patient, such as on the patient's chest or arm, approximately over the superior vena cava-atrium region, or other area as desired, and may comprise part of an external pad 700, which may be, for example, an electrode patch. Alternatively, pad 700 may have componentry or features thereon so that pad 700 itself operates as the second pole without a separate proximal excitation electrode 112 positioned therein or thereon.

Figure 19A:
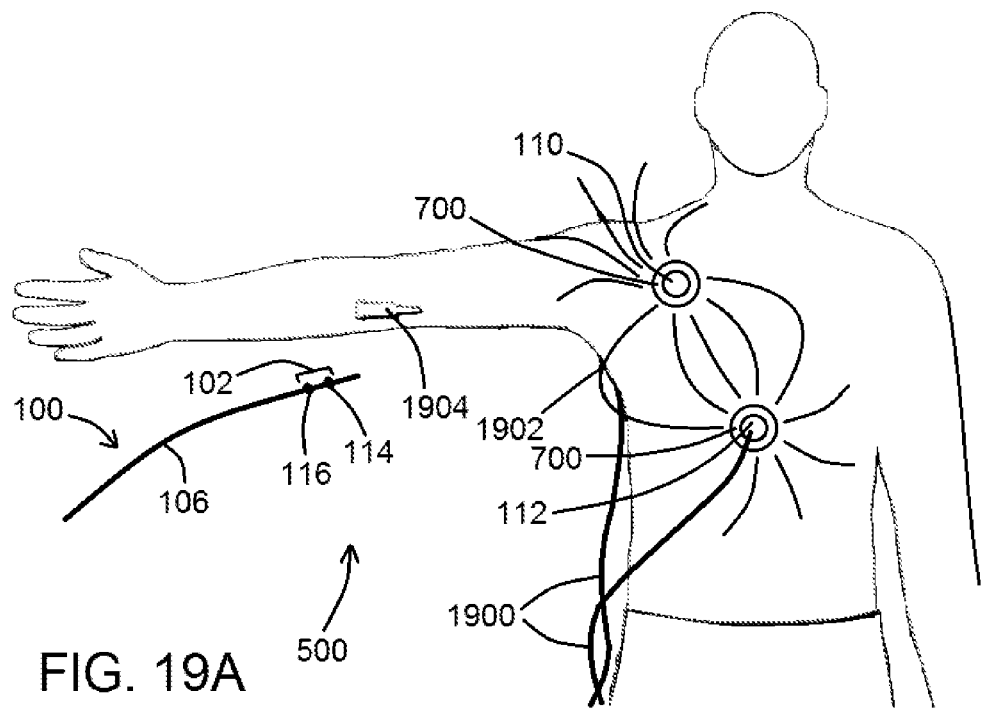
FIGS. 19A-19D show systems comprising a device and two pads, according to exemplary embodiments of the present disclosure.

In such a system 500 embodiment, and upon activation of distal excitation electrode 110 and proximal excitation electrode 112 (or sheath 600), for example, an electric field 1902 (such as shown in FIG. 19A) is generated and is detectable by a detector 102 (such as, for example, distal detection electrode 114 and proximal detection electrode 116) upon device 100. As device 100 is then advanced through the patient's vasculature, from vessels of smaller diameter/cross-sectional area to larger vessels and ultimately to the heart, stepwise changes (increases) in conductance can be identified, and the anticipated pulsatile nature of voltage change due to the pumping of the heart can also be identified, indicating delivery of the distal end 104 of device 100 to the right atrium.

Figure 8A:
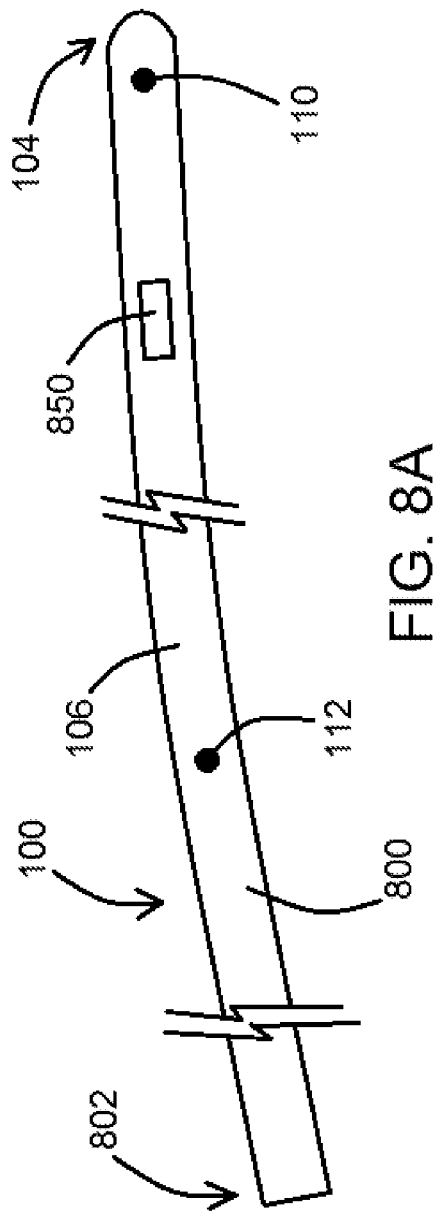
FIG. 8A shows a device with two poles separated substantially apart from one another, according to an exemplary embodiment of the present disclosure.

Yet another embodiment of a device 100 of the present disclosure is shown in FIG. 8A. As shown therein, a first pole (such as a distal excitation electrode 110) may be positioned upon elongated body 106 of device 100, such as at or near a distal end 104 of a PICC line device 100 embodiment. A second pole (such as a proximal excitation electrode 112) may also be positioned upon elongated body 106 of device 100, but closer to the middle 800 the proximal end 802 of a PICC line device 100 embodiment. In such an embodiment, proximal excitation electrode 112 is not located at or near distal end 104 of device 100.

In such a device 100 embodiment, and upon activation of distal excitation electrode 110 and proximal excitation electrode 112, a voltage output would remain constant as the distal end 104 of device 100 is initially advanced toward a region of interest (the atrium, for example) within the patient. A generally constant voltage is experienced because in such an embodiment, distal excitation electrode 110 and proximal excitation electrode 112 are positioned upon device 100 at a constant distance from one another. In this and in other device 100 embodiments of the present disclosure, a distal portion of device 100, and/or a CVC 504 or 2002 used separately or in connection therewith (as referenced in further detail herein), may be cut down (trimmed) as desired/required for a particular patient to meet his or her individual needs, such as by trimming a PICC line, but the distance between distal excitation electrode 110 and proximal excitation electrode 112 (referred to herein as an electrode distance "L") would remain constant (as distal excitation electrode 110 would remain at or near the distal end 104 of device 100). For example, and in at least one embodiment, a stylet or guidewire (exemplary devices 100 or separate devices) could be inserted into a patient's vasculature, then the CVC 504 or 2002 could be cut to length, and then delivered into the patient. Conversely, the CVC 504 or 2002 could be cut to length first, and delivered along with the stylet or guidewire into the patient. In such embodiments, a total PICC line device 100 embodiment length is inconsequential with respect to conductance, as because distance L does not change, and relative changes and/or profiles would be measured. In such embodiments, the voltage would drop as one or both of electrodes 110/112 passes by each vessel bifurcation, such as where the vessel becomes larger or as one or both of electrodes 110/112 transitions from the superior vena cava to the atrium, for example. Phasic changes of voltage may also be observed when the distal excitation electrode 110 is in or near the right atrium due to the pulsatility of the heart. Such a system 500 embodiment would not require detection electrodes, such as distal detection electrode 114 and/or proximal detection electrode 116, as the two poles (such as distal excitation electrode 110 and proximal excitation electrode 112 referenced above) would serve an excitation and detection function, so that a field can be generated and a voltage drop/change can be detected as device 100 is advanced and/or retracted within the patient's vasculature as referenced above.

In the device embodiments shown in FIGS. 1, 3, and 8A, for example, the field (generated by the excitation electrodes, such as electrodes 110, 112) is carried with device 100 as device 100 moves through the vasculature. In such an embodiment, conductance generally increases as detector 102 of device 100 enters larger vessels, and should detector 102 enter a smaller side branch, for example, conductance would generally decrease. Such a phenomenon is consistent with Ohm's Law as referenced herein.

In at least one embodiment, an exemplary device 100 of the present disclosure configured as a PICC line or another type of CVC 504 would include an impedance measuring circuit (an exemplary sensor 850, as shown in FIG. 8A) with audible, tactile, or visual feedback componentry thereon or defined therein. Using such an embodiment, and after placement of device 100 at a desired location within the patient, the portion of device 100 having measuring circuit thereon or defined therein can remain within the patient along with the CVC 504 or can be removed separately from the CVC 504.

Figure 8B:
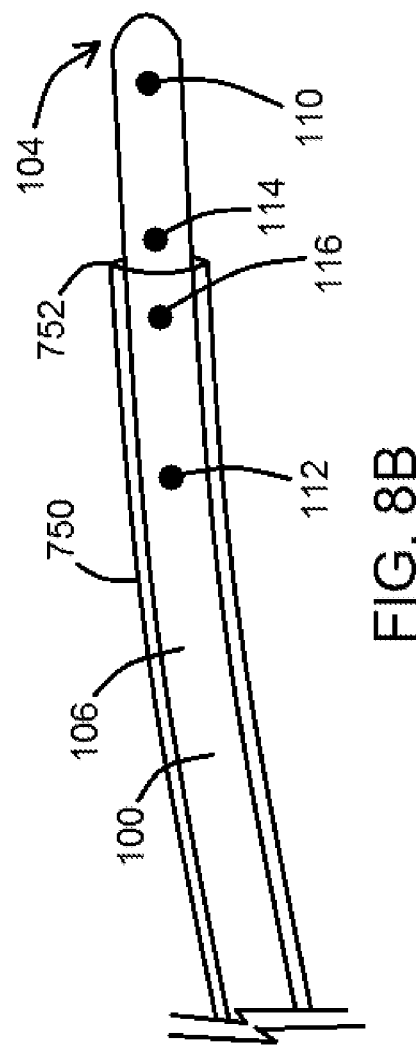
FIG. 8B shows a device with four electrodes being partially covered by an outer tubular body, according to an exemplary embodiment of the present disclosure.
Figure 8D:
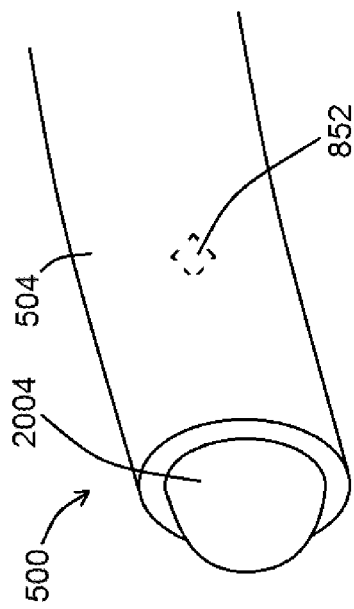
FIG. 8D shows a device configured as a stylet protruding from a distal end of a tubular body, the stylet having electrodes thereon, according to an exemplary embodiment of the present disclosure.
Figure 8C:
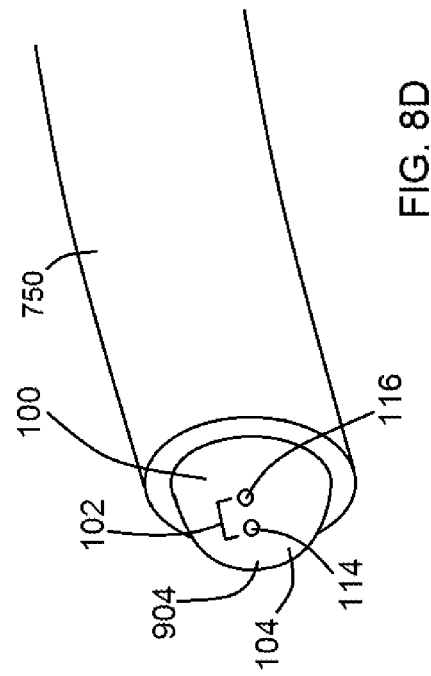
FIG. 8C shows a device configured as a central venous catheter (CVC) with two electrodes thereon, according to an exemplary embodiment of the present disclosure.

FIG. 8C shows another embodiment of a device 100 of the present disclosure. As shown in FIG. 8C, device configured as a CVC (such as a PICC line, for example) with a detector 102 thereon. Detector 102, which may comprise a pair of detection electrodes (such as distal detection electrode 114 and proximal detection electrode 116) may be coupled directly to the elongated body 106 of device 102 (such as shown in FIG. 1, for example), or may be part of a component coupled to elongated body 106, such as within and/or upon an atraumatic tip (such as a distal tip 904), as shown in FIG. 8C, positioned at or near a distal end 104 of device 100. In such an embodiment, device 100 can be advanced through a patient's vasculature as generally referenced herein, and upon ultimate delivery, a medicament or other therapy can be delivered through lumen 108 of device 100 directly to the heart, for example. Detector 102, as referenced herein and as generally applicable to various other device embodiments, may be coupled to one or more wires 1900 as shown in FIG. 8C, which may be embedded within body 106, positioned within lumen 108, or otherwise coupled to body 106, for example, so that data collected by detector 102 can be transmitted therethrough to console 902, for example. In at least one embodiment, electrodes 114, 116 of detector 102 are spaced anywhere from about 0.5 mm to about 2.0 mm from one another, such as, for example, 0.5 mm, 1.0 mm, 1.5 mm, and the like.

Figure 8F:
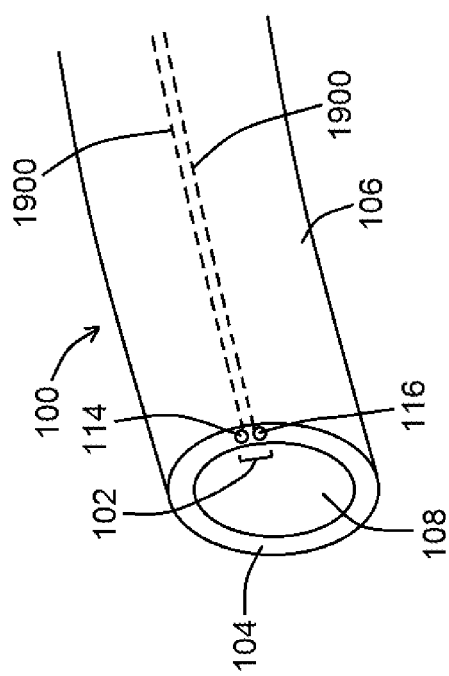
FIG. 8F shows a portion of a system having a wire positioned within a central venous catheter, according to an exemplary embodiment of the present disclosure.
Figure 8E:
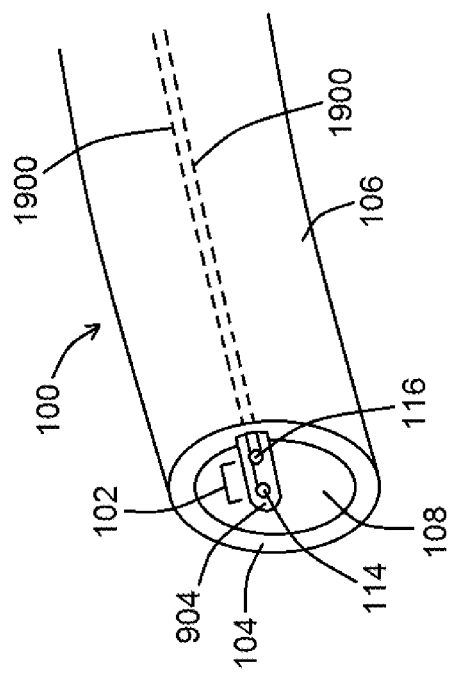
FIG. 8E shows a device configured with two electrodes thereon, according to an exemplary embodiment of the present disclosure.
Figure 19B:
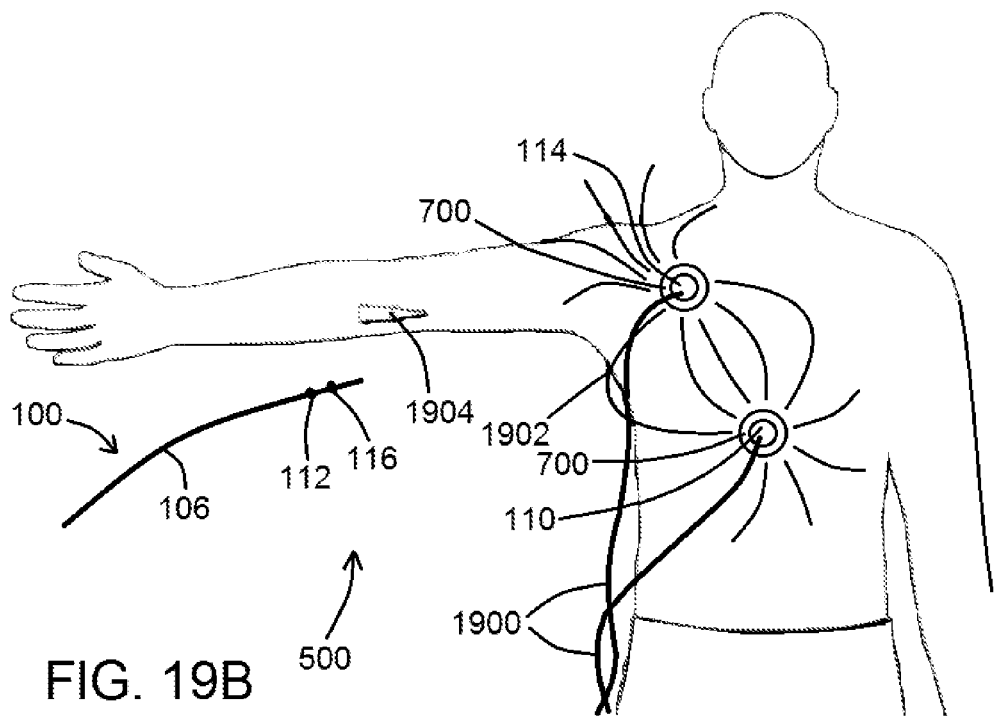
Figure 19C:
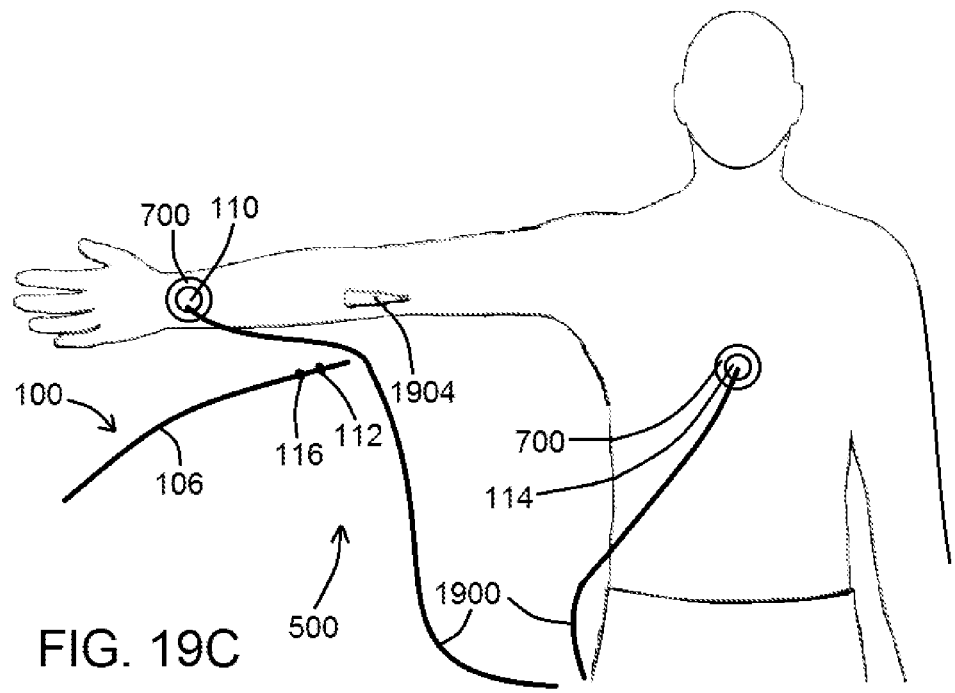
Figure 19D:
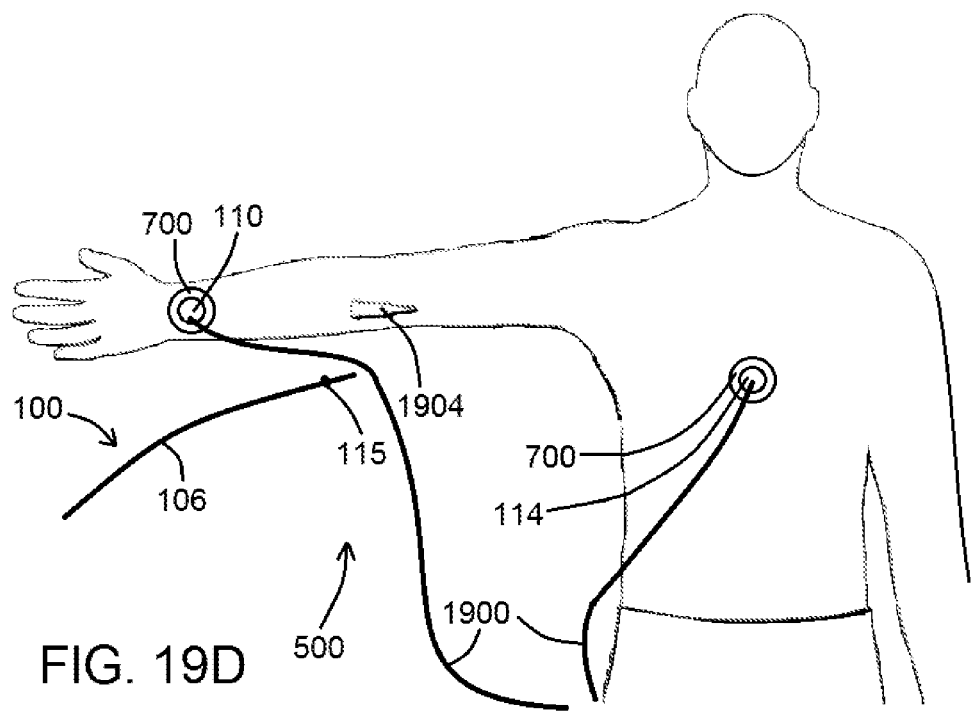

In at least another embodiment, and as shown in FIG. 8E, device 100 has two electrodes (such as electrodes 114, 116, forming a detector 102, for example) positioned at or near the distal end 104 of device 100. However, and in various embodiments, such as those shown in FIGS. 8C-8E, alternative electrode placement, such as the use of at least one electrode (such as electrode 115, discussed in further detail herein and in connection with FIG. 19D, with the unipolar method of use), two electrodes (which could be detection electrodes 114, 116, as shown in FIG. 8E or 19A, in connection with the tetrapolar method of use referenced herein, or one detection electrode and one excitation electrode, such as shown in FIGS. 19B and 19C, as discussed in connection with the bipolar method of use referenced herein), or four electrodes, such as shown in FIGS. 1, 3, and 8B, for example, could be used consistent with the present disclosure, instead of, or in addition to, electrodes 114, 116 (comprising detector 102) as shown therein.

In various embodiments systems 500 of the present disclosure, a guidewire 2004 could be positioned within a CVC 504 lumen prior to insertion in the patient and adjusted so that a small portion, such as 5 to 10 mm or a smaller or larger portion thereof, extends beyond the distal end of CVC 504, as shown in FIG. 8F. Guidewire 2004 can then be locked mechanically (using, for an example, a lock mechanism 852 coupled to guidewire 2004 and/or CVC 504, as shown in FIG. 8F) to that relative position in CVC 504, and the already supplied guidewire 2004 could be used as a CGW of the present disclosure.

Figure 9A:
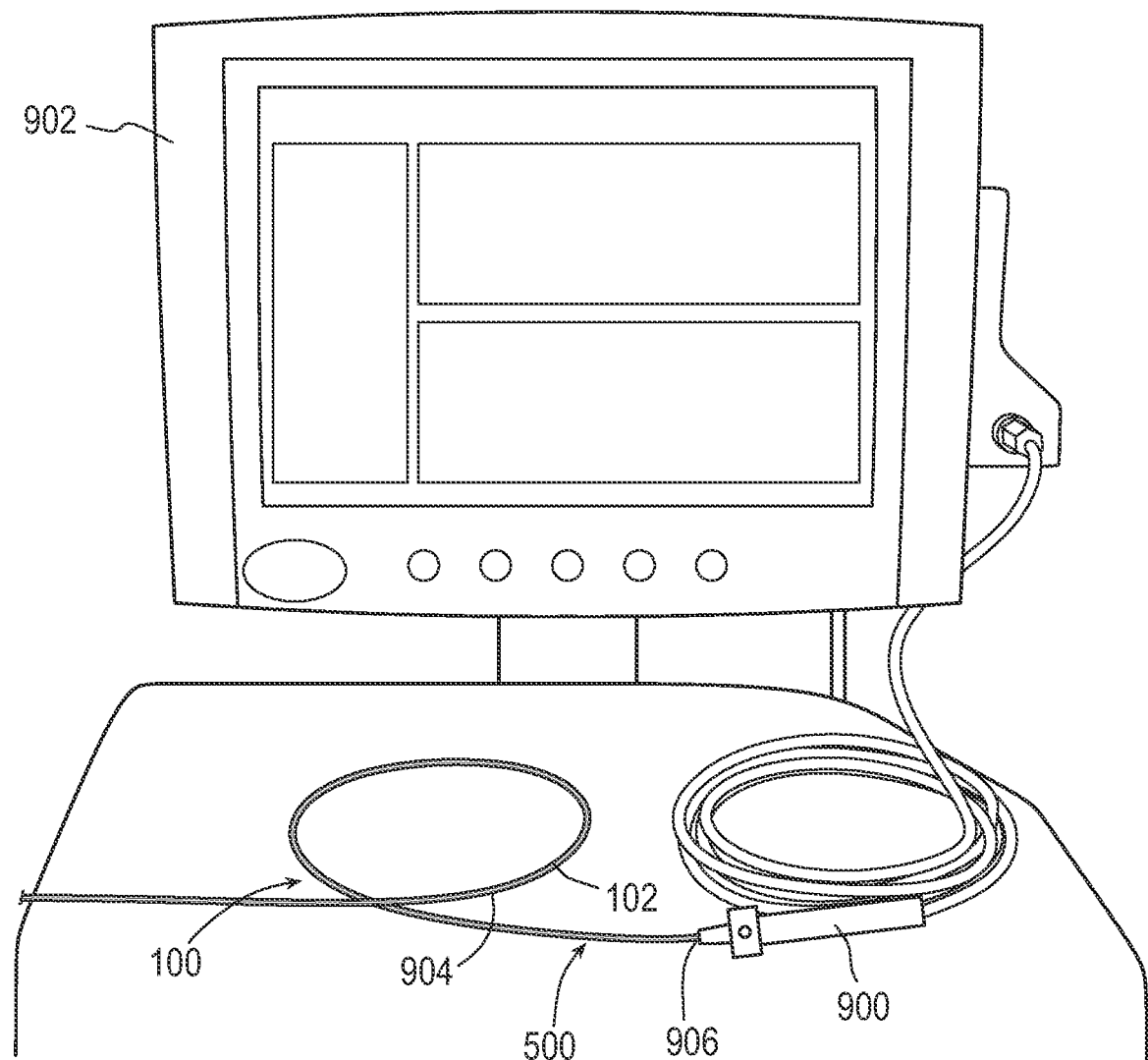
FIGS. 9A and 9B show components of systems, according to exemplary embodiments of the present disclosure.

An additional exemplary system 500 of the present disclosure is shown in FIG. 9A. For a PICC line delivery application, for example, system 500 (which may also be referred to conductance guidewire ("CGW") systems 500 in various embodiments), consists of at least three components: the CGW (an exemplary device 100), a connector handle 900 (also generally referred to herein as a "connector"), and a console 902 (an exemplary data acquisition and processing system), used to deliver a CVC 504, which may also comprise a portion of system 500. In at least one exemplary device 100 embodiment, the device 100 (CGW) is a 0.035" 180 cm long guidewire consisting of a floppy/atraumatic distal tip 904, a tetrapolar measurement electrode section (an exemplary detector 102, comprising two inner electrodes 114, 116 positioned in between two outer electrodes 110, 112), a long coiled body (an exemplary elongated body 106) around a solid core, and a stiff proximal end 906 for easy manipulation and attachment to connector handle 900. The distal tetrapolar electrode section (an exemplary detector 102) is used to determine the proper location for the PICC line placement using electrical conductance measurements.

Figure 9B:
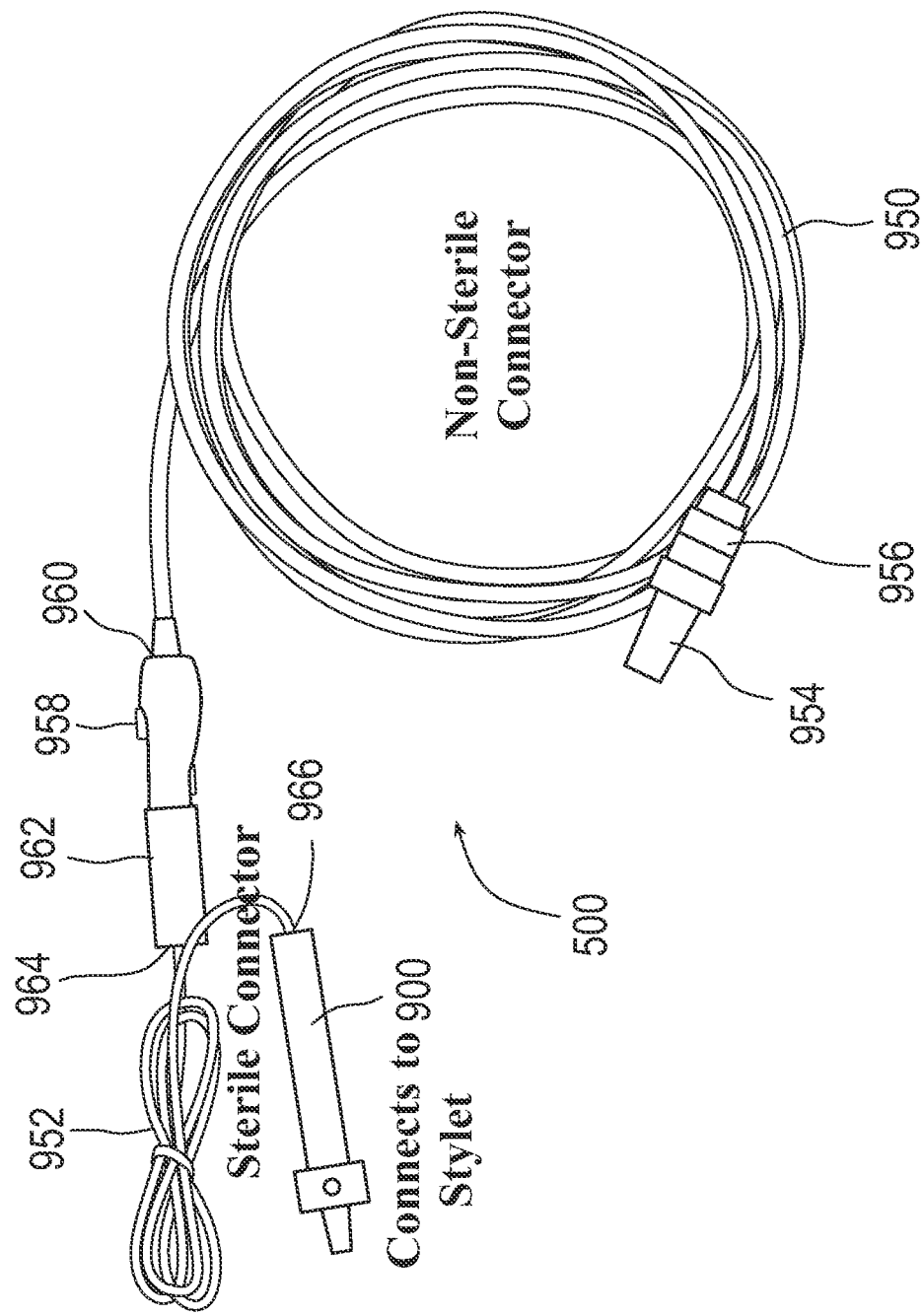

Selected components of another exemplary system 500 embodiment of the present disclosure are shown in FIG. 9B. As shown in FIG. 9B, system 500 components include a first connector 950 and a second connector 952. First connector 950 may, in at least some embodiments, be reusable from patient to patient, and as such would not need to be sterile at the time of use. First connector 950, as shown in FIG. 9B, may comprise a plug 954 at its proximal end 956, whereby plug 954 is configured for coupling to a console 902, such as a touch screen personal computer (PC) as shown in FIG. 9A. First connector 950 may further comprise a distal plug 958 at its distal end 960, configured to connect to a proximal plug 962 at the proximal end 964 of second connector 952. In embodiments without distal plug 958 or proximal plug 962, distal end 960 of first connector 950 would otherwise couple to proximal end 964 of second connector 952. Second connector 952, as shown in the system embodiment shown in FIG. 9B and which may be sterile (intended for single-use) in various embodiments, may terminate at its distal end 966 with a connector handle 900 (also as shown in FIG. 9A), that itself would connect to device 100, which may also be referred to as a stylet.

Although not shown in FIG. 9B, various components of systems 500 of the present disclosure, such as first connector 950 and second connector 952, may have one or more wires 1900 therein or therethrough to, for example, facilitate current and/or data transmission therethrough to various components of systems 500.

During delivery of device 100 and/or a CVC 504 in connection therewith, can be facilitated using a number of guidance means other than visual means displayed by console 902 as referenced herein, For example, tactile or haptic feedback could be generated in the handle 900 or other componentry of the device 100 and/or system 500. Audible guidance could also be useful, such as by providing one or more tones to the operator, with exemplary tones, in at least one embodiment, varying in amplitude or frequency or both based on measured conductance. In addition, and for example, a Bluetooth and/or other wireless audio connection to an earpiece could easily guide an operator. In various embodiments, a combination of feedback could be used (referenced herein as "two-dimensional guidance), such as where one dimension is represented by sound frequency and the other represented by volume. Recognition of the RA-SVC junction may be signaled by interrupting the audio, for example, so as to present bursts or beeps to the operator. If an exemplary system 500 were to contain a wireless connection, for example, a smartphone or another type of portable device 2006, as shown in FIG. 20D, could interface with the system 500 providing visible and/or audible guidance to operator. As smartphones (exemplary portable devices 2006) contain powerful computational capability, trending algorithms could be employed to process raw conductance data and provide guidance to an operator.

In at least one embodiment, electrodes 110, 112, 114, 116 have a 5-2-10 spacing, whereby 5, 2, and 10 refer to the spacing in mm between each consecutive electrode, from distal to proximal, such as in order from distal excitation electrode 110 to distal detection electrode 114 (5 mm), distal detection electrode 114 to proximal detection electrode 116 (2 mm), and proximal detection electrode 116 to proximal excitation electrode 112 (10 mm). The electrodes of detector 102 may be referred to herein numerically as consecutively 1 through 4, with 1 (distal excitation electrode 110) starting at or near distal end 104 of device 100.

Connector handle 900 allows for connection of the conductance guidewire (CGW) (device 100) for measurements and disconnection of the CGW for over-the-wire device delivery. The CGW, in various embodiments, does not require conductance calibration for this application and can be disconnected and reconnected to connector handle 900 at any time during procedures using device 100. Console 902 (an exemplary data acquisition and processing system) may be a personal computer (PC) touch screen that continually displays the conductance results and thus constantly provides feedback to the user about the CGW/PICC line position. Console 902, in at least one embodiment, provides this feedback by injecting a small and safe amount of alternating electric (ac) current through electrodes 1 and 4 (distal excitation electrode 110 and proximal excitation electrode 112, respectively) of the CGW and acquiring, filtering, and displaying the measured conductance across the middle electrodes 2 and 3 (distal detection electrode 114 and proximal detection electrode 116, respectively).

Physical laws of electricity and physiology provide the basis for understanding how the conductance technology on the CGW system 500 (namely device 100 plus other componentry as referenced herein) can deliver the PICC line to the proper recommended location (i.e. in the distal superior vena cava (SVC) proximal to the junction between the SVC and the right atrium (RA), referred to as the "cavoatrial junction"). The CGW (device 100), in at least one embodiment of the present disclosure, contains four electrodes, in which the distal and proximal electrodes (distal excitation electrode 110 and proximal excitation electrode 112) inject a constant mean current (alternating current (AC), for example) and the inner two electrodes (distal detection electrode 114 and proximal detection electrode 116) measure total conductance ($G_T$). When placed inside a blood vessel, Ohm's Law (Equation 1, referenced below) states that the total measured conductance ($G_T$) is related to the cross-sectional area (CSA) of the blood vessel, the blood conductivity ($\sigma$), the spacing between the measurement electrodes (L), and any parallel conductance loss ($G_p$) as follows:

$$G_T = CSA * \sigma/L + G_p \quad \text{(Equation 1)}$$

The value for $G_T$ is known (measured across electrodes 2-3 (distal detection electrode 114 and proximal detection electrode 116) and displayed by console 902), $\sigma$ is constant for blood (since hematocrit and temperature will not change during the procedure), L is a known constant (which is the spacing between electrodes 2 and 3, such as, for example, L=2 mm), and Gp is inversely proportional to CSA as noted in the results provided below. Therefore, since the variables are measured, known, or inversely related to CSA, relative changes in CSA during guidewire (device 100) advancement can be observed simply by monitoring changes in $G_T$ (Equation 2); namely:

$$G_T \propto CSA \quad \text{(Equation 2)}$$

Venous access for CVCs 504 occurs in the cephalic/brachial/basilic/saphenous vein (for example) with a desired location of the catheter tip (distal end 104 of device 100) at the distal SVC. During advancement of the CGW (device 100) from sheath 600 to, for example, the basilic vein, the axillary vein, the subclavian vein, the brachiocephalic vein, the SVC, and the RA, the measured conductance will show step increases as detector 102 of the guidewire (device 100) reaches a new and larger vessel. The location at the step change resulting in the largest absolute conductance coupled with the large pulsatile changes in conductance denotes the location of the cavoatrial junction, as identified in FIGS. 10A and 10B, for example.

The accurate delivery of the catheter to the desired location within the patient occurs by placing the PICC line over-the-CGW. If the PICC line is advanced along the CGW after conductance monitoring, the guidewire is simply disconnected from the handle temporarily while the catheter is fed over-the-wire and then reconnected to the handle. The PICC line can also be advanced along with the CGW during conductance monitoring as long as the catheter does not cover the electrodes. For the former, when the CGW has located the region of interest for catheter placement, the CGW is held in place and the PICC line is advanced over-the-wire until the measured conductance drops very abruptly to nearly zero. When this occurs, the tip of the PICC line will have arrived at the desired location because the catheter will have covered up the second and third electrodes (the measurement site for the device) and caused the CGW to now sense the CSA of the catheter (i.e., almost zero conductance) compared to what it sensed previously in the SVC space (i.e., larger conductance). For example, if a device 100 having a tetrapolar arrangement of electrodes, namely a distal excitation electrode 110 and a proximal excitation electrode 112, with a distal detection electrode 114 and a proximal detection electrode 116 positioned therebetween, and a tubular body (such as a peripherally inserted central catheter or another type of central venous catheter, for example) is advanced along device 100, proximal excitation electrode 112 would be covered by the tubular body first, and when proximal detection electrode 116 is covered by the tubular body, or when the tubular body covers device 100 between proximal detection electrode 116 and distal detection electrode 114, for example, conductance will drop down to almost zero, causing a large spike in voltage, indicating the location of the distal end of the tubular body relative to device 100. This is demonstrated in FIG. 8B, for example, whereby a device 100 having a tetrapolar arrangement of electrodes 110, 112, 114, 116, is at least partially covered by a tubular body (referenced as tubular body 750 in the figure, noting that tubular body may also be a tubular embodiment of a device 100 of the present disclosure), and whereby the distal end 752 of tubular body 750 is shown as covering at least proximal excitation electrode 112. Furthermore, and in at least one embodiment, device 100 is configured as a dialysis/hemodialysis catheter, or is configured to fit within a dialysis/hemodialysis catheter.

In addition to the foregoing, generation of the electric field (using the various poles/excitation electrodes of the present disclosure) can be had using constant current delivery and voltage recording, and constant voltage delivery and measurement of current, for example. In at least certain applications, the use of constant current may be beneficial as it can auto adjust in response to the load. Similarly, and in various applications, constant voltage delivery has the advantage of being output energy-bounded and thus less like to heat or stimulate in certain situations. In view of the same, references herein to "voltage data" may also be viewed as references to "conductance data" depending on the application.

Furthermore, various embodiments of the present disclosure relate to the general concept of being able to determine where a portion of a device 100 of the present disclosure is positioned/located within a body, such as within a patient's vasculature (blood vessels and heart). In various embodiments of the present disclosure, an exemplary device 100 may further comprise one or more additional sensors 850 (such as shown in FIG. 8A), which can also be used to provide general position/location as well, such as an electrogram sensor or a pressure sensor, for example. Device 100 embodiments using one or more sensors 850 in connection with one or more other electrodes/poles could provide additional data, such as potential data analogous to pulsatile data recorded by the conductance, and may also improve overall specificity with respect to the data collected. In view of the same, and in at least a few embodiments, data selected from conductance data, conductance pulsatility data, electrogram data, and/or pressure data can be used to provide feedback to a user with respect to the location of a portion of device 100 within a patient's body, and which can provide the user with instructions, such as instructions to advance, continue advancement, stop advancement, stop, retract, continue retraction, or stop refraction, for example.

In cases where a CVC 504 (or a device 100 configured as a CVC) dislodges after placement of the same and during use, attention can be paid as to how to use various devices 100 and/or systems 500 of the present disclosure to reposition the CVC. For example, if the CVC 504 is known or thought to have migrated, for example to the right ventricle, inferior vena cava, or other vessel, an exemplary method of the present disclosure may comprise the step (and perhaps an initial step) of retracting the CVC 504, rather than advancing the CVC 504, as would be the case during initial delivery and implantation of the same. Guidance can also be provided to the operator, by way of conductance information referenced herein obtained using device 100, so to guide the operator to properly reposition the CVC 504. For example, a device 100 of the present disclosure configured as a wire can be passed through the CVC 504 itself and electrically activated, with little to no calibration concerns, and used to reposition the CVC 504.

In view of the foregoing, various types of phasic measurements can be obtained, such as using data comparing a peak to a minimum of conductance or voltage to distinguish one portion of the vasculature from another (such as to distinguish between the subclavian vein and the heart), where the latter has much greater pulsatility or phasic changes. Furthermore, a gradient method can be used to detect stepwise changes as portions of the device 100 move from a relatively small to a relatively large structure, such as from a vein to the heart. This latter method can also be used to detect navigation, as movement in the wrong direction within the vasculature would give a smaller gradient corresponding to a smaller vessel, as opposed to a positive gradient corresponding to movement from a small to a larger vessel.

Vessel perforation can also be identified using various devices 100 of the present disclosure. Tissue wall conductivity is approximately ⅓ that of blood. As such, and should a device 100 and/or CVC 504 used in connection therewith perforate a vessel, a significant drop in conductivity would be identified. Exemplary algorithms used in connection with this process, that generally detect a constant increase and/or a constant decrease in conductivity, would be used to signal that the device 100 and/or CVC 504 is moving generally in the wrong direction, and the device 100 and/or CVC 504 could be retracted accordingly.

Thus, the CGW has the ability to function as a standard platform for over-the-wire delivery and is a novel system for device navigation without the need for fluoroscopy or x-ray. Below is a description of methods used for the bench and in vivo validation of the CGW system for delivery of the PICC line.

Bench Validation

A series of rigid phantoms were used to create a simulated anatomy made of plastic tubing filled with physiological 0.9% NaCl solution (Baxter Healthcare Corporation, Deerfield, Ill.). The bench anatomy consisted of four (4) consecutive segments with diameters of 6.4 mm, 9.5 mm, 13 mm, and 15 mm. A side branch (starting diameter=6.4 mm) with decreasing diameter was attached to the 9.5 mm tubing.

Validation of the CGW system 500 to properly deliver the CVC 504 to various locations within the simulated anatomy was performed using three (3) CGWs (devices 100) by a single user who had received training with CGW system 500. The user was instructed to place the CGW (device 100) and CVC 504 at three distinct locations proximal to the simulated cavoatrial junction (i.e. 1.3 cm, 1.6 cm, and 2 cm proximal from the junction between the 13 mm and 15 mm tubing) using only conductance feedback from the console 902 screen. This proximal 1.3 cm to 2 cm range is within the recommended location for CVCs 504 in the distal one third of the SVC. The CGWs were placed in random order with a repeat placement for each CGW/PICC line. To assess the accuracy and repeatability of data using system 500, the difference was calculated for each run versus the desired location in the phantom (accuracy) and for each first run versus the second repeat run (repeatability). To visualize the deviation of the CGW system 500 results from perfection, identity plots were made for the accuracy (each run vs. desired location) and repeatability (first run vs. second run). A Bland Altman (difference in the measurements versus their means) analysis was performed for both accuracy and repeatability, along with calculations of the mean and standard deviation of the differences and the root mean square error (RMS).

To establish the relationship between conductance and CSA, a series of rigid phantoms from 4-16 mm (i.e., approximate range seen in the animals) were filled with 0.9% NaCl solution, the CGW was placed in each well, and the conductance was recorded.

Animal Validation

Six (6) swine (weight=53±10 kg) were used for in vivo validation of CGW (device 100) delivery of CVC 504 without fluoroscopy. Initial sedation was accomplished via an intramural injection of TKX (0.004 mg/kg), consisting of a mixture of telaxol (500 mg), ketamine (250 mg), and xylazine (250 mg). A stable anesthetic plane was established via intubation and ventilation with 100% oxygen and 1-2% isoflurane. The cephalic vein was located and punctured using a modified Seldinger technique for placement of a short sheath 600 in the vessel. The CGW (device 100) was then placed in sheath 600, the CGW was connected to connector handle 900, connector handle 900 was connected to console 902, and the CGW (device 100) was advanced into the vasculature.

The only monitoring during CVC 504 advancement in the vasculature was accomplished through observing the resultant conductance tracing on the console 902 screen (i.e., no fluoroscopic guidance). Placement of CVC 504 occurred either simultaneous with CGW (device 100) advancement or after CGW advancement. If placement occurred simultaneously, CVC 504 was locked to the CGW (device 100) proximally such that the tip of the catheter did not cover up the measurement electrodes. If placement occurred after CGW advancement, the guidewire (device 100) was simply disconnected from the connector handle 900 and CVC 504 was advanced over the wire (device 100) while keeping the wire in place until the conductance tracing abruptly dropped close to zero (i.e., catheter covered the second through fourth electrodes (distal excitation electrode 112, distal detection electrode 114 and proximal detection electrode 116) or the location where the conductance tracings occur). The target location for the CVC 504 tip was in the lower SVC at a distance of 2 cm away from the cavoatrial junction.

In one animal, a series of angiographic images were taken with contrast of the venous pathway of the CGW (device 100) and CVC 504. For 1 cm increments, CGW conductance was recorded at each location, and the diameter of the vessel was measured. A venous blood sample was obtained, and the venous blood conductivity was determined using a Rho cuvette (Millar Instruments, Inc., Houston, Tex.). Equation 1 was then used to calculate the parallel conductance ($G_p$) at each location along the venous pathway based on the conductance and conductivity measurements. The relationship between the percentage of the total conductance attributed to $G_p$ as a function of CSA was then obtained.

After CVC 504 placement, the animal was terminated via an anesthetic overdose. The chest was opened, and the RA and SVC were located to measure the relative position of the CVC 504 tip to the cavoatrial junction.

Results

Figure 10A:
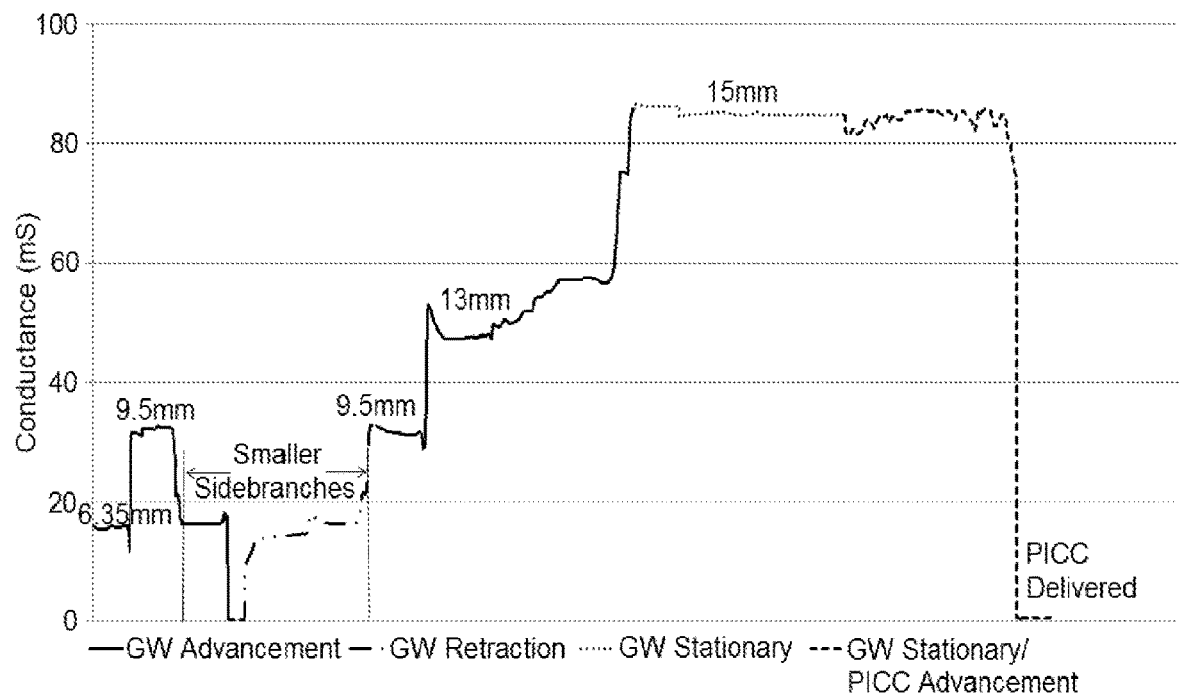
FIGS. 10A and 10B show conductance traces from bench and in vivo animal experiments, respectively, according to exemplary embodiments of the present disclosure.
Figure 10B:
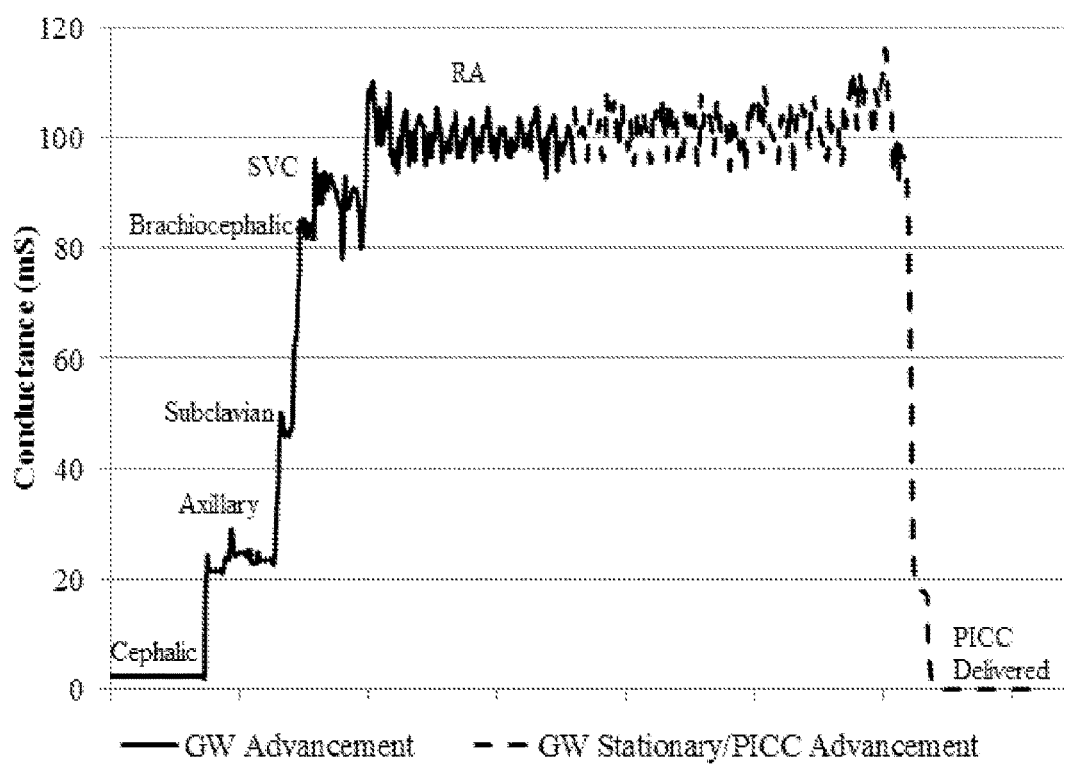

FIGS. 10A and 10B show bench and in vivo animal conductance traces, respectively. The solid, solid and dotted, dashed, and dotted lines represent forward advancement of the guidewire, retraction of the guidewire, no guidewire movement, and no guidewire movement/advancement of the CVC 504, respectively. Bench validation in the simulated anatomy (FIG. 10A) demonstrated how the CGW system 500 provided feedback: 1) when the guidewire (device 100) was being advanced in the incorrect direction (i.e., away from the increasing tubing dimensions) and 2) when the guidewire arrived at the correct location in the simulated cavoatrial junction (i.e., the junction between the 13 mm and 15 mm tubing). After initial insertion into the 6.4 mm tubing, the CGW was advanced to the 9.5 mm tubing and then into a series of smaller side branches. The conductance dropped when advancing into the side branches, demonstrating movement away from the heart. As the CGW continued to be advanced in the incorrect direction, the vessels were smaller, leading to an eventually conductance reading of close to zero. This sustained decrease in conductance provided feedback that the CGW was being advanced in the incorrect direction. The CGW was retracted (FIG. 10B—dash-dotted lines) to the last position in which the conductance reading was the highest prior to improper advancement (i.e., 9.5 mm tubing in this case). The guidewire was then advanced again and this time in the correct direction to the 13 mm and 15 mm tubing as evidenced by the increases in conductance. The junction between the 13 mm and 15 mm tubing (i.e. the simulated cavoatrial junction) was determined by slowly advancing the CGW until the conductance suddenly increased. Once the CGW was placed at the cavoatrial junction, it was held stationary while CVC 504 was advanced over the wire (FIG. 10A—dashed lines). Once CVC 504 reached the cavoatrial junction, the user received feedback that the catheter was in the correct position since the conductance reading had dropped to zero. The conductance drop to zero was due to the fact that the CGW (device 100) was no longer sensing the large CSA of the 15 mm tubing, instead the very small CSA inside CVC 504. Such a procedure is generally consistent with method 400 shown in FIG. 4 and described in detail herein, with respect to initial device 100 advancement and later CVC 504 advancement over device 100.

A conductance profile similar to the bench validation was seen in all in vivo swine experiments (FIG. 10B). A series of step increases were seen as the CGW (device 100) was advanced from the basilic, the axillary, the subclavian, the brachiocephalic vein, the SVC, and finally to the RA. Once the cavoatrial junction was identified by the absolute largest conductance, CVC 504 was advanced over the CGW until the conductance dropped to zero, as shown in FIG. 10B.

Figure 11A:
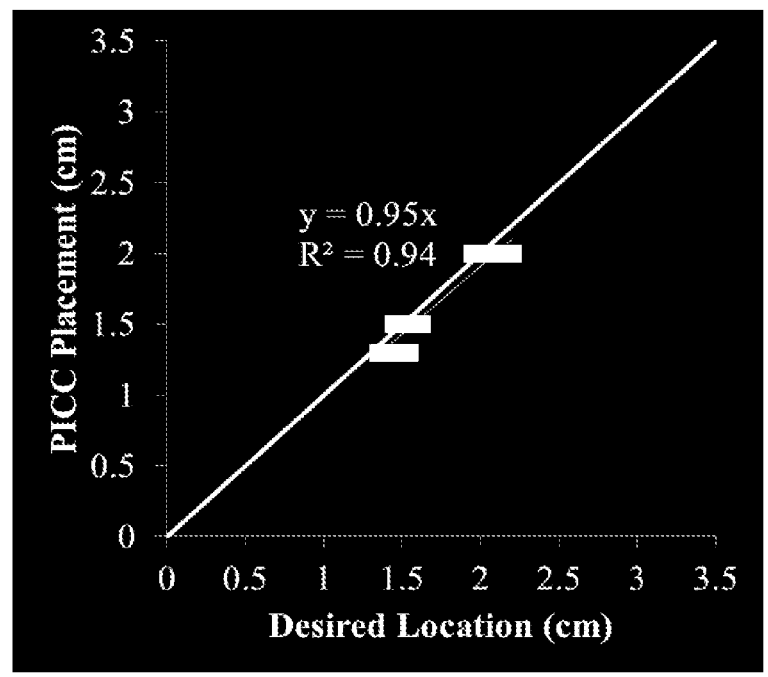
FIG. 11A shows accuracy data for bench experiments showing the measured distance for the PICC placement versus the desired, target location, according to an according to an exemplary embodiment of the present disclosure.
Figure 11B:
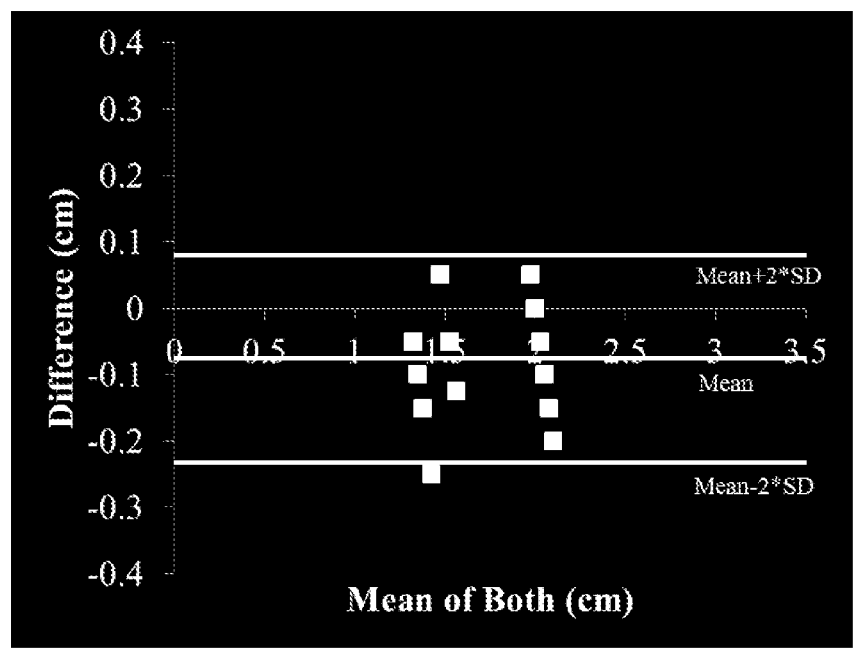
FIG. 11B shows the Bland Altman Analysis in connection with the accuracy data shown in FIG. 11A, according to an exemplary embodiment of the present disclosure.
Figure 12A:
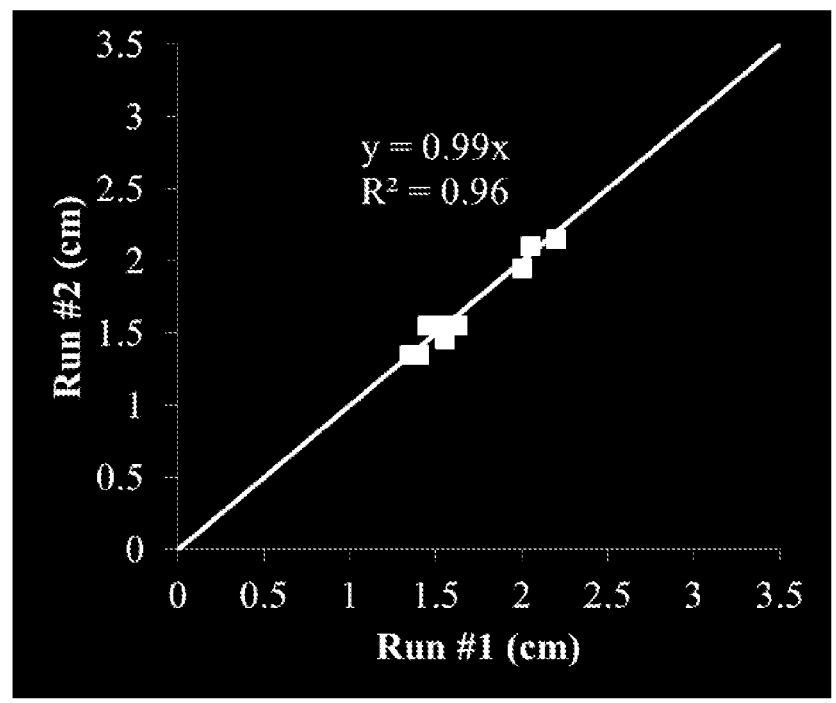
FIG. 12A shows repeatability data for bench experiments showing repeat runs for PICC line placement, according to an exemplary embodiment of the present disclosure.
Figure 12B:
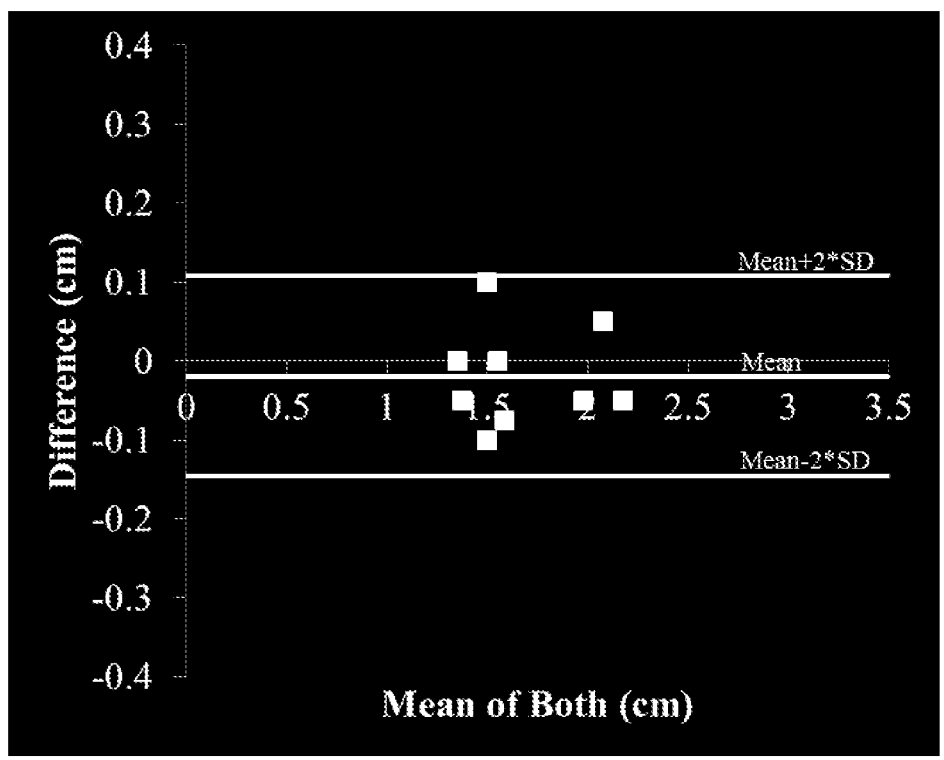
FIG. 12B shows the Bland Altman Analysis in connection with the repeatability data shown in FIG. 12A, according to an exemplary embodiment of the present disclosure.
Figure 13A:
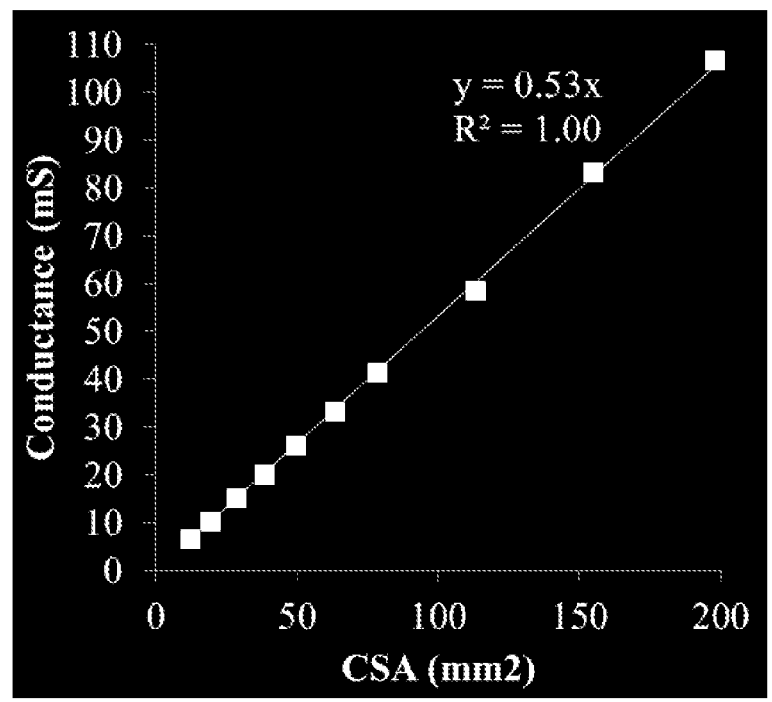
FIGS. 13A and 13B show the linear relationship between the total conductance and cross-sectional area (CSA) on the bench and the percentage of $G_T$ that is directly related to Gp as a function of CSA from in vivo data, respectively, according to exemplary embodiments of the present disclosure.
Figure 13B:
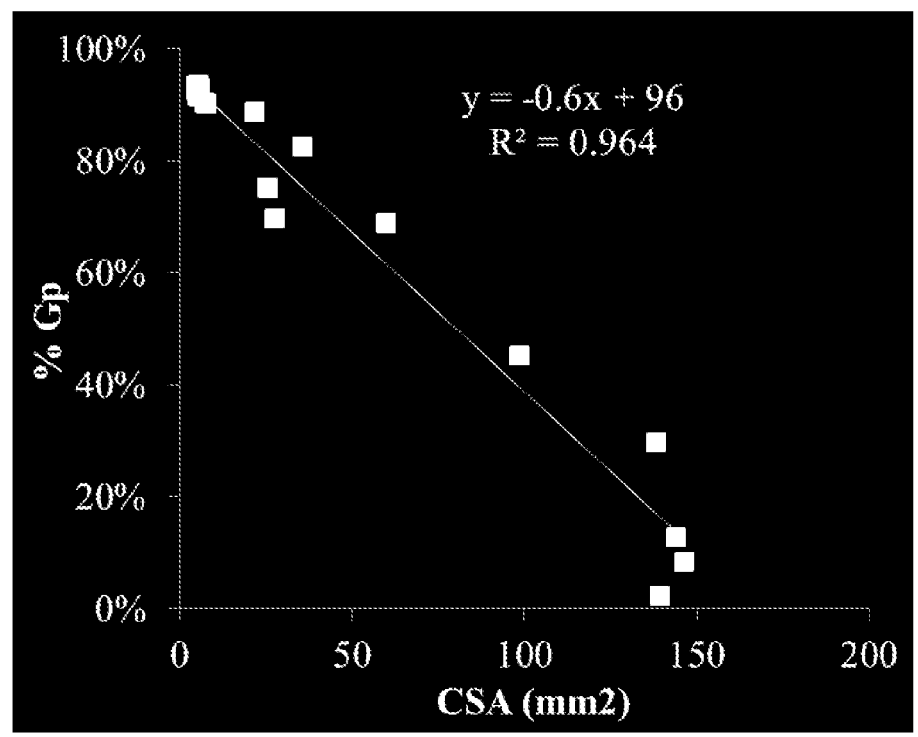

The placement of CVC 504, as noted above, was highly accurate and repeatable for the bench experiments. The RMS error for accuracy and repeatability for all runs and distances was 6.6% and 3.8%, respectively. The average difference between the measured and the desired location of the CVC 504 tip (accuracy) was −0.07±0.07 cm for the nominal distances between 1.3-2.0 cm, as noted in FIGS. 11A and 11B. FIG. 11A shows accuracy data for bench experiments showing the measured distance for CVC 504 placement versus the desired, target location which was proximal to the simulated cavoatrial junction at 1.3 cm, 1.6 cm, and 2 cm distances. The solid dark line shown in FIG. 11A is the identity line and the smaller dark line is the regression. FIG. 11B shows the accuracy Bland Altman analysis for the aforementioned data. For all distances, the average difference between repeat placements for the CGWs was −0.01±0.06 cm, as shown in FIGS. 12A and 12B. FIG. 12A shows repeatability data for bench experiments showing the repeat runs for CVC 504 placement, and FIG. 12B shows the corresponding Bland Altman analysis. The solid dark line is the identity line and the smaller dark line is the regression, which cannot be seen as it is below this line. A highly linear relationship was found for the conductance as a function of CSA on the bench (FIG. 13A; $R^2=1.00$) and for the percentage of the total conductance ($G_T$) attributed to parallel conductance (Gp) as a function of vessel CSA in vivo (FIG. 13B; $R^2$=0.96). FIGS. 13A and 13B show the linear relationship between the total conductance and CSA on the bench and the percentage of $G_T$ that is directly related to Gp as a function of CSA from in vivo data, respectively.

Figure 14A:
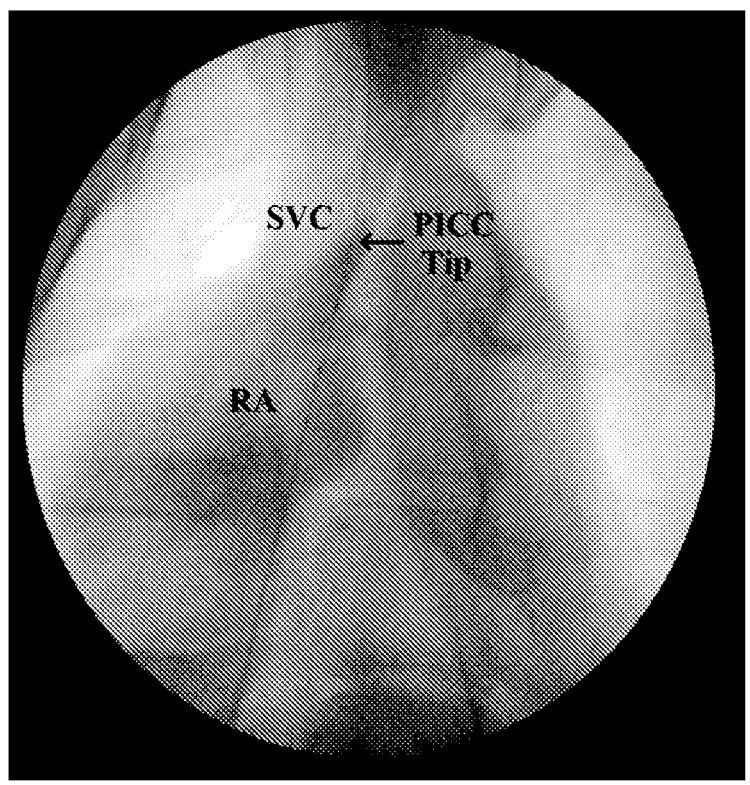
FIGS. 14A and 14B show the confirmation of CGW navigation of PICC tip delivery to the distal SVC using fluoroscopy and post-mortem direct visualization, respectively, according to exemplary embodiments of the present disclosure.
Figure 14B:
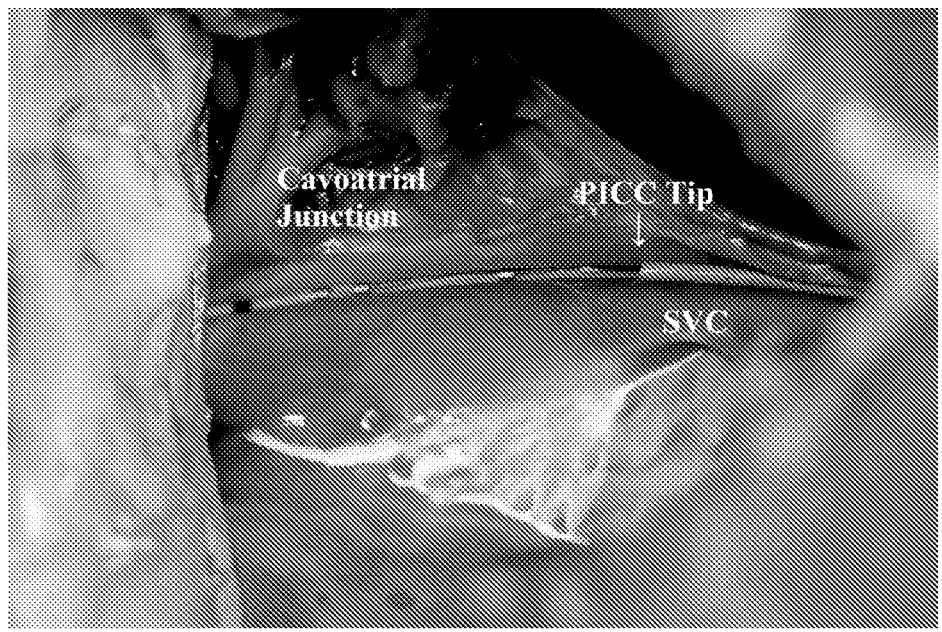

Placement of CVC 504 was highly accurate in vivo in domestic swine. Validation of the proper CVC 504 placement was achieved through direct visualization of the catheter in the vasculature prior to and upon termination as shown in FIGS. 14A and 14B. FIGS. 14A and 14B show the confirmation of CGW navigation of CVC 504 tip delivery to the distal SVC using fluoroscopy (FIG. 14A) and post-mortem direct visualization (FIG. 14B). Arrows point to the CVC 504 tip in the distal SVC. Fluoroscopy was not used to aid in the guidance, but is shown in the figures as a confirmation. CVC 504 was offset 2 cm from the middle electrodes and fixed in place during advancement. The x-ray and post-mortem image both show that the middle CGW electrodes (distal detection electrode 114 and proximal detection electrode 116) have accurately located the cavoatrial junction and the CVC 504 tip is therefore offset 2 cm distal from this location in the distal SVC. In FIG. 14B, the distal electrode (distal excitation electrode 110) is in the RA, the middle electrodes (distal detection electrode 114 and proximal detection electrode 116) are at the cavoatrial junction (see the trabeculations just above the middle electrodes), and the proximal electrode (proximal excitation electrode) is in the SVC.

The CVC 504 tip was placed with 5.1% RMS accuracy of the target location of 2 cm proximal from the cavoatrial junction in the SVC in all animals (as identified Table 1 shown below and FIGS. 14A and 14B.

TABLE 1

| Animal | Weight (kg) | Measured Position Proximal to Cavoatrial Junction (cm) | Difference from Desired Target (cm) |
| --- | --- | --- | --- |
| 1 | 63 | 1.75 | 0.25 |
| 2 | 68 | 2 | 0 |
| 3 | 47 | 2 | 0 |
| 4 | 48 | 2 | 0 |
| 5 | 46 | 2 | 0 |
| 6 | 48 | 2 | 0 |

Discussion

The use of an exemplary CGW system 500 of the present disclosure, as generally referenced above, provides an anatomically-based method for CVC 504 delivery. Both results on the bench and in vivo demonstrated that the identification of important anatomical landmarks (i.e., the cavoatrial junction) can be accurately and repeatably located solely with CGW system 500 and without the need for fluoroscopy. The accuracy with CGW system 500 is based on Ohm's Law that directly relates measured electrical conductance and vessel CSA (Equations 1-2). From Equation 1, since the blood conductivity and length are known constants, the total measured conductance ($G_T$) is related to both the vessel CSA and the parallel conductance ($G_p$). The work shown in the venous system (such as shown in FIG. 13B) shows that $G_p$ is inversely related to vessel CSA. Therefore, since $G_p$ is inversely related to vessel CSA, advancement into larger and larger venous vessels, like the SVC and RA, minimizes the role of $G_p$ and further magnifies the identification of important landmarks. Thus, the CGW technology stands out from other technologies because of the physics-based principle to identify variations in CSA.

The use of exemplary CGW systems 500 of the present disclosure for CVC 504 placement has high clinical significance. Multiple benefits are gained through use of CGW system 500, which include: 1) an anatomically-based guidance system, 2) accurate and repeatable guidance, 3) ease of use, 4) virtually no increase in time for placement (i.e. already use guidewires), 5) potential for reduced cost (i.e., better accuracy CGW can lead to less follow up x-rays for readjustment of the lines), 6) potential to reduce x-ray exposure, and 7) possibly less time from the initial CVC 504 placement to actual therapy delivery to the patient.

The highly accurate and repeatable CVC 504 placement using an exemplary CGW system 500 of the present disclosure is based on a physical law as opposed to subjective image interpretation or physiological recordings. Fluoroscopy is less reliable than conductance (subjective vs. objective) and vulnerable to intra-observer variability related to interpretation of a two-dimensional projection of three-dimensional soft tissue organs. On the other hand, conductance is an unbiased physical measurement directly related to the CSA of the vasculature and can be more accurate than standard fluoroscopic imaging. On the bench and in vivo, the CGW system 500 showed high accuracy and repeatability in locating important anatomical landmarks (FIGS. 10A-14B and Table 1). Since the CGW system 500, in at least one embodiment, monitors the size of the vasculature, with little training, the clinician has the ability to place CVC 504 in the desired location in the distal SVC, the cavoatrial junction, or the RA, depending on clinical philosophy and/or need. Since there are various opinions as to the optimal location for CVC 504 placement, exemplary CGW systems 500 of the present disclosure may provide a useful tool for the study of various CVC 504 locations and outcomes.

In various embodiments of the present disclosure, devices 100 are advanced through a patient's venous vasculature, such as through a vein in a patient's arm to the heart. Identifying the right atrium-superior vena cava (RA-SVC) junction, according to the present disclosure, involves the general identification that a distal end 104 of device 100 is proceeding through the venous vasculature to portions of said vasculature with a generally larger bore. Utilizing findings of monotonically increasing bore, advancement of the device 100 would be through vasculature having a generally steady increase in luminal cross-sectional area until an indication that the distal end of device is at the RA-SVC junction, which would be a more dramatic increase.

Guidance using an exemplary CGW system 500 of the present disclosure flows easily within standard clinician procedures and usage of system 500 requires only limited training Guidewires are already used by clinicians in CVC 504 placement procedures, and the current technology integrates within this platform. Unlike other guidance tools, exemplary CGW systems 500 of the present disclosure do not require attachment to other vitals (i.e., ECG) and can be used with any type of CVC 504 (i.e., single, double, or triple lumen of any size) from multiple catheter manufacturers. Accurate placement using CGW system 500 may necessitate only a confirmatory chest x-ray or completely eliminate the need for fluoroscopic confirmation altogether, thus saving time and reducing procedural costs. Further cost savings can be made by including the guidewire (device 100) in a standard CVC 504 kit (i.e., since the CGW (device 100) functions as a standard guidewire). The technology is not limited for use in just CVC 504 placement applications, but can be expanded for placement of any central catheter (i.e., Quinton PERMCATH™, etc.). While the console 902, in at least one embodiment, receives power from a standard 110V power line, other embodiments of system 500 operate using battery power to allow for portable usage in the operating room, clinic, or off-site location (home-care) using a small console 902, such as, for example, a hand-held device (i.e., like an iPhone). Finally, improved accuracy for placement of the CVCs 504 should decrease the amount of radiation exposure to the patient as well as clinician and provide less time between initial catheter placement and confirmation for actual device usage (i.e., quicker therapy to the patient). The proof of concept findings in the present swine model merit future clinical application of this technology.

The in vivo testing referenced herein was completed in a non-diseased animal model. This is appropriate since atherosclerosis generally occurs only in the arterial side of the vasculature. There are other conditions, such as venous congestion or thrombosis, in which the venous vasculature can be altered, and additional animal studies could examine the utility of this technology under these conditions. The swine model was appropriate for this study since both the size and structure of the venous vasculature is very similar to humans. Surprisingly, the accuracy results for the in vivo studies were slightly more accurate than the bench studies. This is due to the fact that only quarter cm resolution was used for the in vivo studies, as compared to mm resolution for the bench experiments, but this was not statistically significant (i.e., 6.6% on bench vs. 5.1% in vivo).

Implants in the venous system, like vena cava filters and/or pacemaker leads, may affect navigation using exemplary CGW systems 500 of the present disclosure. However, placement of central catheters to the SVC/RA is generally counter-indicated for patients with SVC filters or a right side pacemaker lead. We have done some preliminary experiments to show that coated devices (e.g., all pacemaker lead bodies) do not negatively impact CGW navigation due to the insulative barrier on these devices (data not shown). No arrhythmias were seen while the CGW (device 100) and a pacemaker were used simultaneously Inherent electrical signals from the heart (i.e., SA node) do not interfere with the conductance readings on the guidewire because the tetrapolar technology, namely the use of electrodes 110, 112, 114, and 116, injects a local current and measures a voltage drop with a much greater relative amplitude and much higher frequency than other surrounding physiological tissues.

The aforementioned experiments were performed using a 0.035" guidewire (device 100). Some clinical CVCs 504 are 0.035" compatible, but most are 0.018" compatible. The overall guidewire diameter should not impact the conductance results, as the conductance recordings are affected mainly by electrode spacing (i.e., the spacing will be the same) as opposed to guidewire size. Furthermore, the conductance technology can also be directly placed on the stylet of the PICC lines, as referenced herein with respect to the device 100 embodiment shown in FIG. 1, for example.

As referenced herein, exemplary devices 100 of the present disclosure can be catheters, wires, stylets, PICCs, or other CVCs. Stylets, as referenced herein and in certain embodiments, may be relatively stiff as compared to an outer sheath (such as tubular body 750 shown in FIG. 8B). In at least one embodiment of a catheter (an exemplary device 100 of the present disclosure), the catheter has a lumen 108, starting at a proximal end of device and extending toward the distal end, but not all the way through to the distal end, so that another device (a wire, for example), could be positioned within lumen 108. A valve (not shown) may be present at a proximal end of device 100 to seal the connection between device 100 and another device inserted within lumen 108. A device 100 embodiment configured as a stylet can be configured to fit within a lumen 108 of a second device 100, whereby the second device 100 is configured as a PICC or another CVC, for example. FIG. 8D shows such an embodiment, whereby device 100 (stylet) is configured with a detector 102 thereon, whereby device 100 is positioned within and protruding from a tubular body 750. As shown in the figure, an atraumatic tip (such as a distal tip 904) is positioned at or near a distal end 104 of device 100, and detector 102 is positioned thereon (at or proximal to distal tip 904). In at least one embodiment, and when distal end 104 protrudes approximately 1-2 mm out of the distal end 752 of tubular body 750, detector 102 is able to operate as intended consistent with the present disclosure.

Figure 15B:
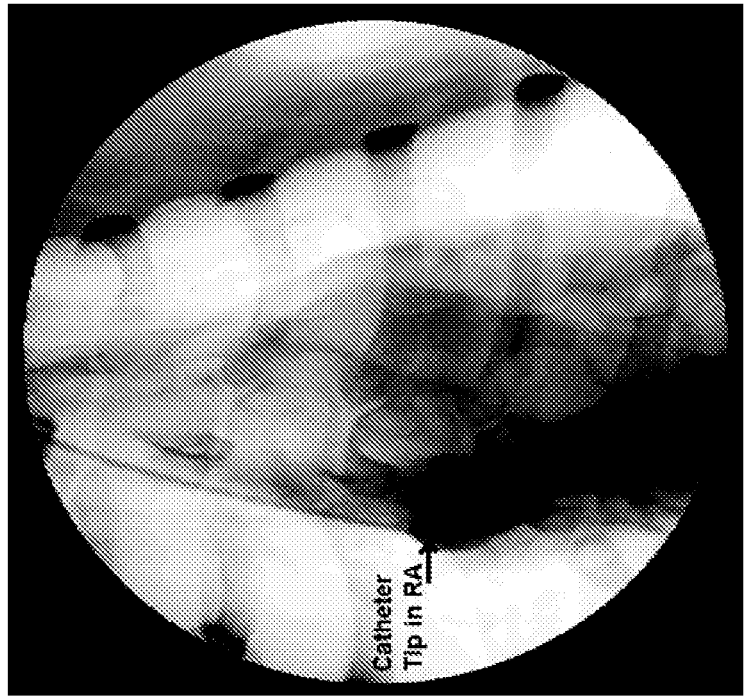
FIGS. 15A and 15B show a portion of a PICC line positioned within a patient, according to exemplary embodiments of the present disclosure.
Figure 15A:
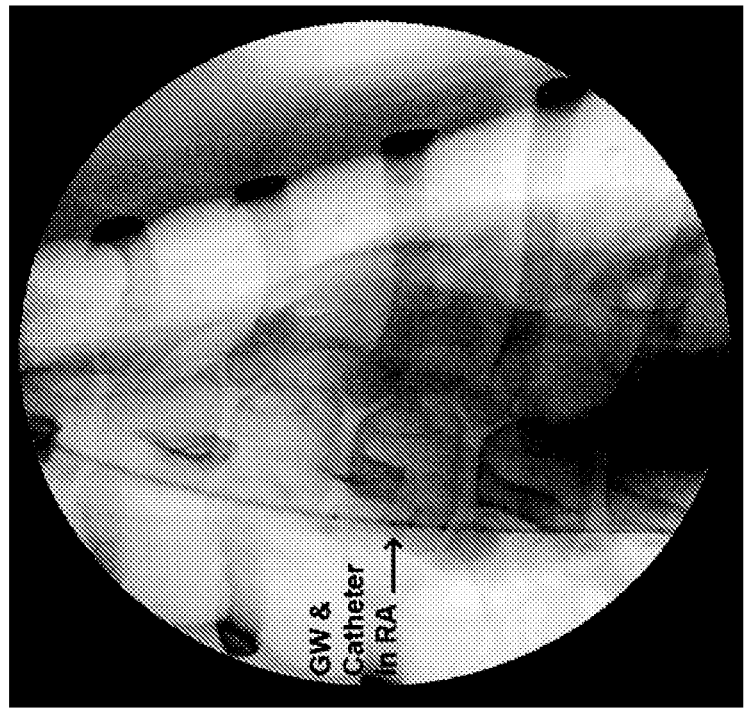

FIG. 15A shows a patient scan whereby at least a portion of device 100 (identified as "GW & Catheter" in the figure) is positioned within the right atrium, and FIG. 15B confirms the location of the same by way of injecting contrast through the catheter (which can either be a catheter device 100 embodiment or a CVC 504 of the present disclosure) so that the contrast can identify and confirm the location of the CVC 504 tip within the patient.

Figure 16A:
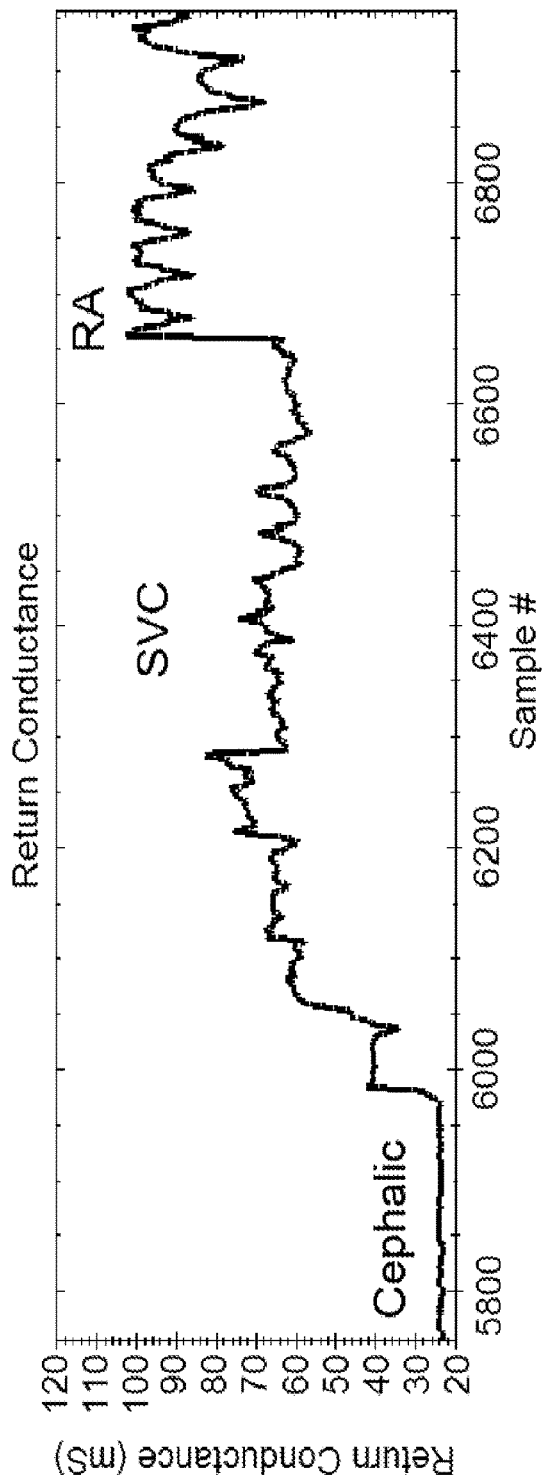
FIGS. 16A and 16B show conductance traces from advancement of a device to the right atrium and retraction away from the right atrium, respectively, according to exemplary embodiments of the present disclosure.
Figure 16B:
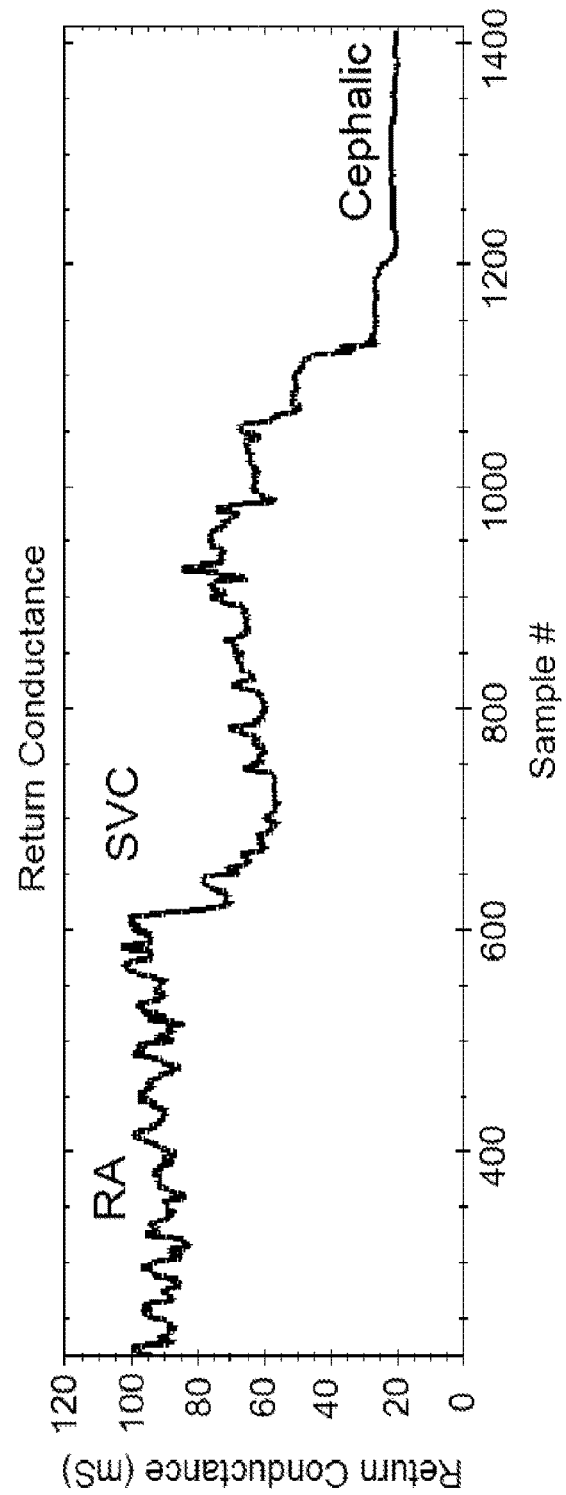

FIGS. 16A and 16B show in vivo animal conductance traces. FIG. 16A shows a conductance trace based upon advancement of an exemplary device 100 of the present disclosure into the radial vein, into the subclavian vain, into the superior vena cava, and into the right atrium, whereby increases in conductance are identified from one portion of the patient's vasculature (canine, in this example) to another to the right atrium. FIG. 16B also shows a conductance trace, but is instead based upon retraction of an exemplary device 100 of the present disclosure from the right atrium into the superior vena cava, into the subclavian vein, and into the radial vein, whereby decreases in conductance are identified from the right atrium to various portions of the patient's vasculature.

FIGS. 17A and 17B show additional in vivo animal conductance traces, whereby the device 100 was introduced into the patient's jugular vein and advanced to the superior vena cava to the right atrium. Such advancement occurs through a central line, which may described as the line from the jugular (or subclavian) vein to the brachiocephalic vein to the superior vena cava to the heart. In both examples, one excitation electrode (such as distal excitation electrode 110) was positioned on device 100, and the second excitation electrode (such as proximal excitation electrode 112) was positioned upon a pad 700 positioned on either the patient's left (FIG. 17A) or right (FIG. 17B) arm. The pulsatility (oscillation) nature of the conductance is readily apparent in FIGS. 17A and 17B when the distal excitation electrode 110 on device 100, for example, reaches the heart.

Figure 18:
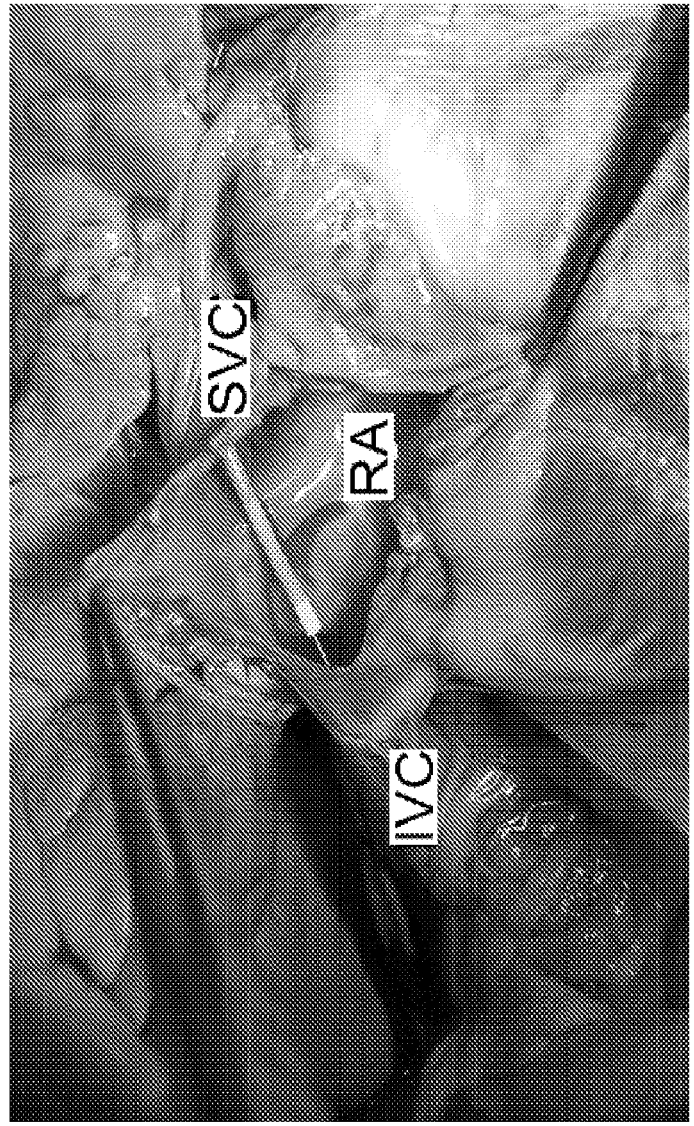
FIG. 18 shows an image of a canine patient, post-mortem, used to confirm the location of the distal end of PICC line positioned within the right atrium, according to an exemplary embodiment of the present disclosure.

FIG. 18 shows an image of a canine patient, post-mortem, used to confirm the location of the distal end of CVC 504 positioned with the right atrium, whereby the positioning of the same was performed using an exemplary method of the present disclosure.

An additional system 500 embodiment of the present disclosure is shown in FIG. 19A. As shown therein, an exemplary device 100 of the present disclosure is configured as a guidewire, a guide catheter, or a PICC line. In an embodiment where device 100 is configured as a guidewire or a guide catheter, it would be positioned within the patient prior to advancement of a CVC 504 over the same.

Regardless of device 100 embodiment, devices 100 used in connection with two externally placed excitation electrodes (such as electrode patches (pads 700)), whereby pads 700 themselves serve as the poles or whereby excitation electrodes (such as distal excitation electrode 110 and/or proximal excitation electrode) are positioned upon one or more pads 700, devices 100 do not need to have excitation electrodes 110, 112 positioned thereon as the two (or potentially more) poles are provided using pads 700 as shown in FIG. 19A. In addition, and in the system 500 embodiment shown in FIG. 19A and in other system 500 embodiments of the present disclosure, one or more wires 1900, connected to one or more pads 700, could be used to transmit a current from an ECG/EKG device 2000 (shown in FIGS. 20B and 20C, for example), so to generate an electric field 1902 detectable by a detector 102 (such as, for example, distal detection electrode 114 and proximal detection electrode 116) upon device 100.

As shown in FIG. 19A, a first pad 700 and a second pad 700 are each positioned upon the patient's torso. While other pad 700 locations may be used, the present disclosure includes disclosure of the pad placement whereby one pad 700 is positioned adjacent to the vein that the device 100 will pass through on the way to the right atrium, and the second pad is positioned adjacent to the right ventricle or the right atrium of the heart (or generally positioned away from the first pad, such as on an opposing arm of a patient, at or near the patients neck, elsewhere on the torso, etc.). Such a position, as indicated by studies performed in connection with the present disclosure, have not only created a sufficient electric field for detection using detector 102 of device 100, but also allow for optimal conductance traces to be obtained showing the desired stepwise changes as the distal end 104 of device moves from the access point of the patient (such as a sheath 600 as shown in FIG. 6 or a port 1904 as shown in FIG. 19A, while also showing the anticipated pulsatile nature of voltage change due to the pumping of the heart, indicating delivery of the distal end 104 to the right atrium. In an embodiment using two pads to generate the electric field (the pads are the poles), if a detection portion of device 100 is outside the field, conductance is generally high and voltage is very low, and when the detection portion of device 100 moves back into the field, conductance significantly drops, while voltage increases. Other pad locations, such as placing one pad 700 adjacent to the patient insertion site and placing the other pad 700 on the patient's torso or arm, could be used as well and are within the scope of the present application.

In the device embodiments shown in 7B, 8C and 19A, for example, the field (generated by the excitation electrodes, such as electrodes 110, 112) is not carried with device 100 as device 100 moves through the vasculature. Instead, the field is generated by electrodes that are generally stationary, such as those coupled to or positioned on a sheath 600 or a pad 700. In such an embodiment, changes in conductance can be obtained using detector 102 (electrodes 114, 116, for example) as detector 102 moves with device 100 through the patient's vasculature.

In at least one embodiment of using an exemplary device 100 of the present disclosure, power line radiation may be sufficient to create a detectable field within a patient such that, for example, passive detection of 50/60 Hz (or potentially different signal frequencies) from intravascular electrodes could be used to gauge vessel size (diameter or cross-sectional area). As such, a relatively "passive" system, versus use of specific external pads 700 and/or internal sheaths 600, can be used in place of an electrical field generated by said components.

As referenced above, several additional system 500 embodiments of the present disclosure are included herein, as shown in the block diagrams of FIGS. 20A-20D. FIG. 20A shows a block diagram of a system 500, comprising at least a device 100 with one pole (shown as distal excitation electrode 110 therein, but could be another excitation electrode) and a sheath 600 with another pole (shown as proximal excitation electrode 112 therein, but could be another excitation electrode). An exemplary device 100 may optionally comprise a platinized tip 702 (or other type of metallic tip (referenced herein as platinized tip), located at or near a distal end 104 of device 100, as shown in FIG. 7A. The use of platinized tip 702, for example, may increase the surface area of the distal end 104 of device 100, and an exemplary platinized tip 702 can serve as a pole for use with a second pole to generate an electric field as generally referenced herein. Furthermore, and in at least one embodiment, platinized tip 702 would not extend beyond distal end 104 or device 100, regardless of device 100 configuration (wire, CVC, or catheter). In an exemplary embodiment of a system 500 wherein device 100 is configured as an impedance wire and used in connection with a CVC 504, device 100 could still operate to obtain conductance and/or voltage measurements as referenced herein when distal end 104 of device 100 is flush with a distal end of CVC 504 or a distal end 604 of sheath 600, or if distal end 104 of device protrudes beyond a distal end of CVC 504 or a distal end 604 of sheath 600. In various embodiments of devices 100 and systems 500 of the present disclosure, a most distal pole/electrode can be positioned at distal end 104 of device 100, so that the most distal pole/electrode can be used to obtain conductance and/or voltage measurements within a vasculature even when flush or relatively flush with a distal end of a CVC 504 or sheath 600.

FIG. 20B shows a block diagram of another exemplary system 500 of the present disclosure, comprising at least a device 100 with one pole (shown as distal excitation electrode 110 therein, but could be another excitation electrode), a pad 700 with another pole (shown as proximal excitation electrode 112 therein, but could be another excitation electrode) or operating on its own as the other pole, whereby pad 700 is operatively coupled to an ECG/EKG device 2000 by way of one or more wires 1900. FIG. 20C shows yet another system 500 embodiment, comprising a device 100 with a detector 102 positioned thereon (such as, for example, distal detection electrode 114 and proximal detection electrode 116), a first pad 700 with a first pole (shown as distal excitation electrode 110 therein, but could be another excitation electrode) or operating on its own as the other pole, and a second pad 700 with a second pole (shown as proximal excitation electrode 112 therein, but could be another excitation electrode) or operating on its own as the other pole, whereby pads 700 re operatively coupled to an ECG/EKG device 2000 by way of one or more wires 1900. As shown in FIGS. 20A-20C, various system 500 embodiments may also comprise a CVC 504. FIG. 20D shows a block diagram of yet an additional system 500 of the present disclosure, comprising an exemplary device 100 of the present disclosure and a central venous catheter (CVC) 2002 (also referred to herein as CVC 504). CVC 2002 or 504, for example, may have other access points from the patient and which may be delivered to other areas within the patient's body. In such embodiments of systems 500, as shown in FIG. 20D for example, device 100 can be used to place the distal end 104 of device 100 to a desired location within the patient, and CVC 2002 or 504 can be delivered over device 100 to the desired location.

During uses of exemplary devices 100 of the present disclosure, an ECG/EKG device 2000, such as shown in FIG. 20B, can also be used to monitor a patient's heart. In situations where an exemplary device 100 is being delivered and when an ECG/EKG device 2000 is displaying patient cardiac information, device 100 and/or a CVC 504 used in connection therewith could be made to press against the vessel wall when in the RA to confirm location by precipitating a premature atrial contraction (PAC) of the heart, for example.

In at least some embodiments of the present disclosure, several main components, such as a device 100 configured as a CVC or a separate CVC 504 or 2002, a guidewire 2004 (as shown in FIG. 20D), and various electronic components disclosed herein, could be built into a catheter device 100 and/or CVC 504 or 2002, and optionally a connector handle/connector 900 of an exemplary system 500 of the present disclosure.

In at least another embodiment, and as shown in FIG. 20E, a balloon catheter 2050 may also be used in connection with various devices 100 and/or systems 500 of the present disclosure. For example, balloon catheter 2050 could be introduced into the venous system, inflated and slowly advanced therethrough. By noting the amount (length) of balloon catheter 2050 introduced into the patient, the balloon 2052 of balloon catheter 2050 could be further inflated at various stages of introduction. If in a narrow lumen, inflation resistance would be felt on an inflation source 2054 (such as a syringe) in communication with balloon 2052, for example. If in a large chamber such as the RA-SVC junction, little resistance would be evident upon incremental inflation. Confirmation of location could be obtained by attempting to withdraw or tugging on balloon catheter 2050, for example. Once the balloon catheter 2050, is located in the RA-SVC junction, a PICC (exemplary CVC 504) could be introduced over balloon catheter 2050, and advanced until reaching the inflated balloon 2052, at which time the balloon is deflated, the CVC 504 advanced by an amount equal to one-half the balloon diameter, for example, and balloon catheter 2050 could then be removed.

Furthermore, and upon initial delivery of a device 100 and/or CVC 504 into a vasculature to an initial location of interest, a user of device 100 and/or CVC 504 can ultimately position a distal end 104 of device 100 or a distal end of CVC 504 to a final location within the vasculature using pull-back or push-forward of the same. For example, and upon initial delivery of a CVC 504 into a vasculature as generally referenced herein, a clinician can either pull-back or push-forward a portion of CVC 504 after initial delivery to ultimately position the same. Should, for example, the clinician wish to have a distal end of CVC 504 positioned 1-2 cm past the RA-SVC junction, a clinician may push-forward CVC 504 past its initial position at the RA-SVC. In at least some embodiments, the pull-back or push-forward distance can be determined based upon indicia 138 positioned on one or both of device 100 and/or CVC 504, so that the clinician, for example, can visually see the pull-back or push-forward distance.

In addition to the foregoing, and in various embodiments (such as those embodiments where only two poles are used (such as distal excitation electrode 110 and proximal excitation electrode 112, for example), such as those shown in FIGS. 6-8, for example, electrodes 110, 112 operate not only as excitation electrodes, but also in their capacities as detection electrodes, so that an electric field can be generated and conductance data can be obtained using only two electrodes.

Furthermore, the present disclosure includes disclosure of simultaneous advancement of two devices, such as a device 100 and tubular body 750, a wire and a device 100 configured as a catheter, or a combination of at least two general devices of the present disclosure. Such simultaneous advancement would allow one device (a PICC line, for example) to be advanced to a desired location while a detection device (such as device 100, for example) is advanced with the PICC line.

As generally referenced herein, the disclosure of the present application uses impedance, through a device 100 configured as a PICC line or not configured as a PICC line and used in connection with a CVC 504, that is delivered using at least one excitation electrode (such as distal excitation electrode 110) on the device 100 and at least another excitation electrode (such as proximal excitation electrode). Other embodiments, such as those whereby the two poles are positioned upon the patient (as shown in FIG. 19A, for example), are also disclosed in detail herein. Use of the same, as referenced herein and demonstrated in the figures, can measure and determine near field anatomical shapes, which is novel to the present disclosure.

FIGS. 21A through 21E show additional profiles using various devices of the present disclosure, comparing a tetrapolar method of the present disclosure to a bipolar and a unipolar method of the present disclosure. In general, the "tetrapolar method" refers to using devices 100 of the present disclosure having two detection electrodes (and optional additional electrodes/features), and whereby two other electrodes (used for excitation) are also used on device 100.

The "bipolar method" refers to using devices 100 of the present disclosure whereby at least one, and in certain embodiments preferably only one, detection electrode and at least one, and in certain embodiments preferably only one, excitation electrode are used on device 100, and where two other electrodes (one excitation and one detection) are used but not on device 100, such as in connection with sheath(s) 600 and/or pad(s) 700. Such a bipolar method could be performed using a combination of devices 100, sheaths 600, and/or pads 700 (which comprise exemplary systems 500 of the present disclosure), as shown in, for example, FIG. 19B, which shows an exemplary system 500 whereby one pad 700 includes an excitation electrode 110 (or another numbered excitation electrode) and whereby the other pad 700 has a detection electrode 114 (or another numbered detection electrode), and whereby a device 100 is used comprising the other excitation electrode 112 (or another numbered excitation electrode) and the other detection electrode 116 (or another numbered detection electrode). FIG. 19C shows yet another system 500 embodiment having componentry shown therein suitable to permit the bipolar method to be performed. As shown therein, FIG. 19C shows a pad 700 with an excitation electrode 110 positioned therein and positioned at or near the patient's wrist, with the other pad 700 with a detection electrode 114 thereon positioned near the patient's heart. Other pad 700 positions are potentially used as referenced herein, such as on the patient's torso, arm, and/or leg, for example.

In brief summary, and as noted above, the tetrapolar method involves using two excitation electrodes and two detection electrodes positioned on device 100. Conversely, the bipolar method involves using one excitation electrode and one detection electrode on or in the body, but not on device 100, and using another excitation electrode and another detection electrode on device 100 itself. Advancement of device 100 through the patient's vasculature toward the heart would be performed as generally described herein.

Figure 21A:
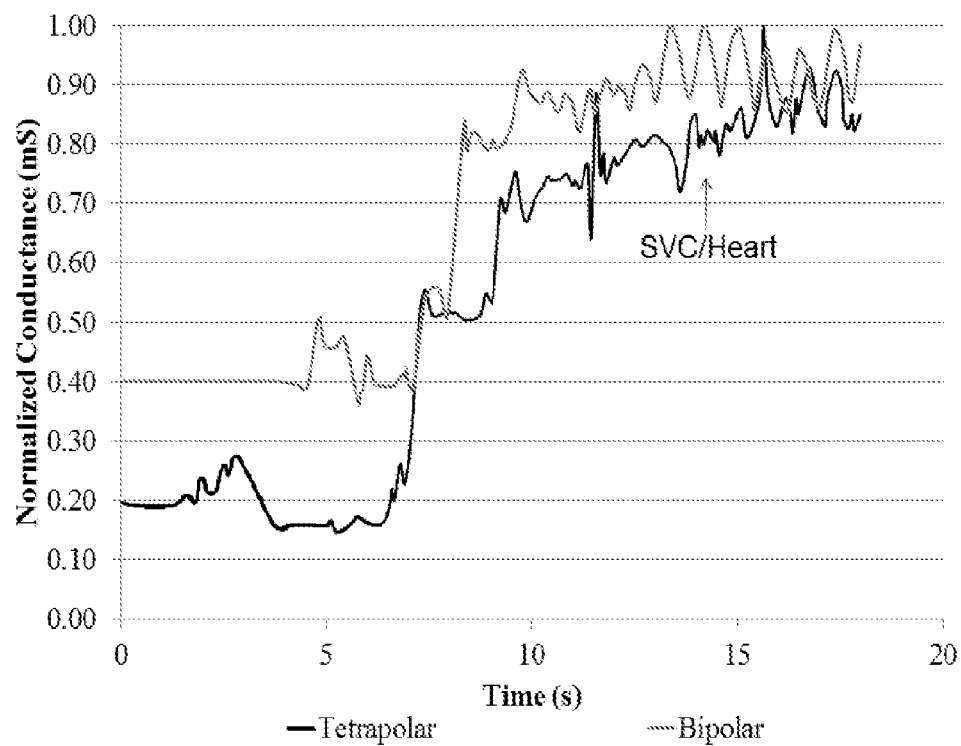
FIG. 21A shows conductance curves obtained using devices of the present disclosure while performing a bipolar method or a tetrapolar method, according to exemplary embodiments of the present disclosure.

FIG. 21A shows two conductance plots, with the bipolar method data starting at a higher initial conductance and remaining generally relatively higher, and with the tetrapolar method data starting at a lower initial conductance and remaining generally relatively lower. As shown therein, and over time (advancement of device 100 from the arm toward the heart over a period of approximately 15 seconds), generally stepwise increases in conductance are shown as the detection portion (such as detector 102) of device 100 moves from the point of entry into the patient toward the heart (to and within vessels of increasing size), and noting a very strong and readily identifiable pulsatility signal in connection with using the bipolar method. Said data demonstrates that the both methods (bipolar and tetrapolar) may be used with devices 100 of the present disclosure to obtain desired conductance data profiles.

Figure 21B:
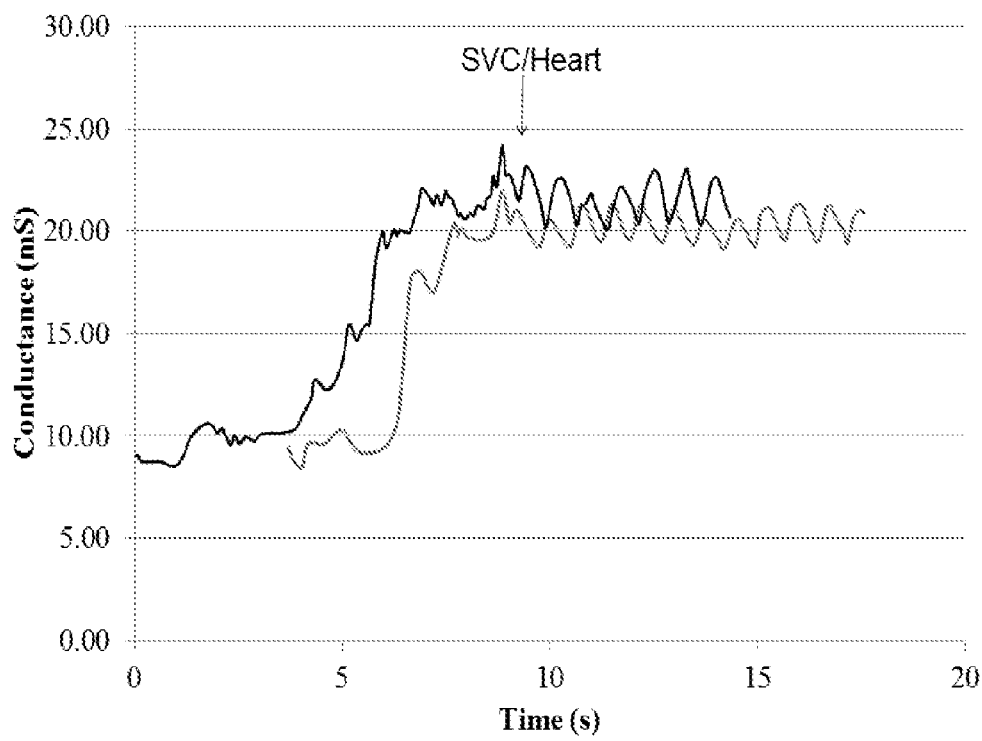
FIG. 21B shows conductance curves indicative of a bipolar method with different placement of electrode pads upon the body, according to exemplary embodiments of the present disclosure.

FIG. 21B shows that placement of electrodes/electrode pads (a second pole, for example) on the patient's body has some impact on the conductance measurements, but in general, bipolar navigation is not particularly sensitive to the position of the electrodes on the surface of the body. The generally higher line (starting at 0 seconds) indicates position of the electrode pad at the parasternal-right axillary location, while the generally lower line (starting at about 4 seconds) indicates position of the electrode pad at the subxiphoid-right axillary location.

Figure 21C:
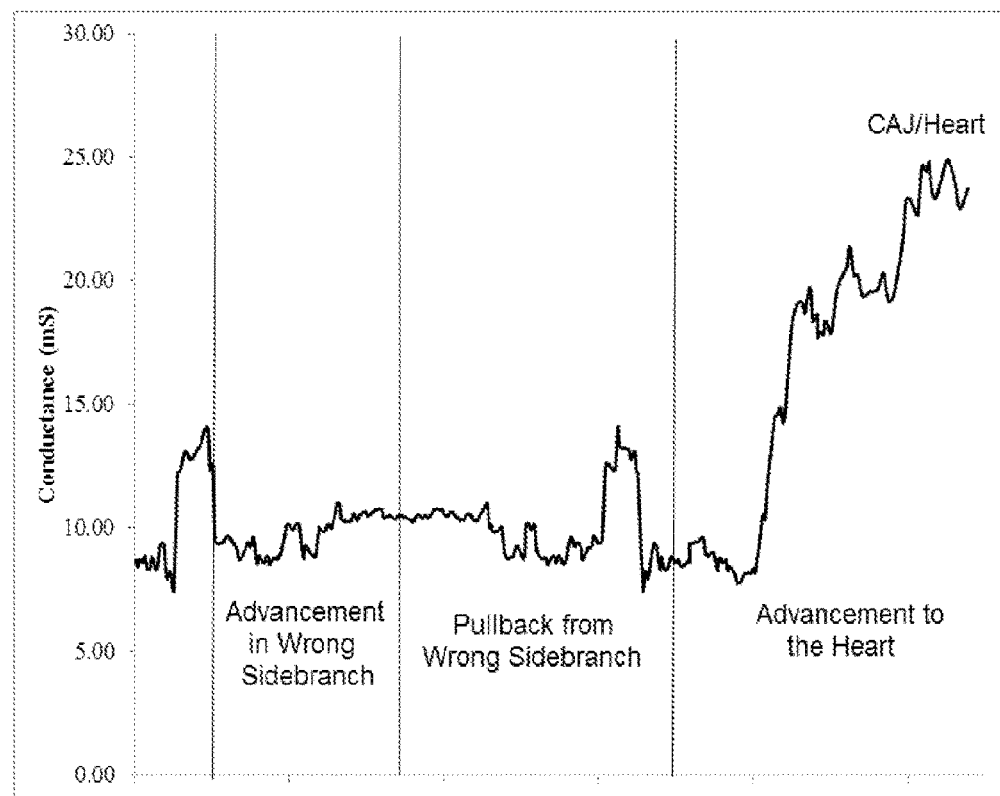
FIG. 21C shows conductance curves indicative of a bipolar method starting at either arm, according to exemplary embodiments of the present disclosure.

FIG. 21C shows a conductance curve demonstrating the ability of the bipolar method to detect sidebranches within the vasculature. As shown therein, advancement of device 100 into the wrong sidebranch shows an initial spike in conductance, but then a relatively low and constant conductance, while withdrawal shows the relatively low conductance leading to a spike in conductance and a general decrease in conductance, indicative of withdrawal through a vessel that is generally decreasing in size during withdrawal. Readvancement through the proper vasculature toward the heart shows the expected increase in conductance and the eventual pulsatility detection as desired. As generally referenced herein, pulsatility indicates that the detector 102 of device 100 is positioned at the superior vena cava or right atrium, and allows a second device, such as a PICC line, to be advanced over the device 100 to the desired location.

Figure 21D:
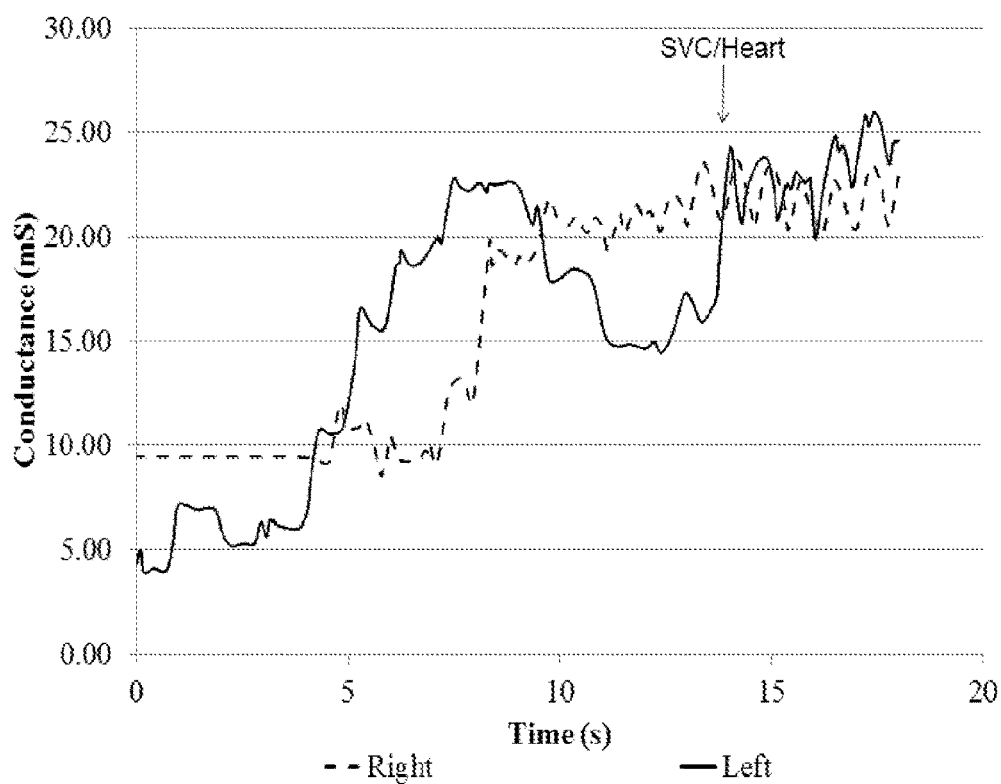
FIG. 21D shows a conductance curve indicative of a bipolar method and detecting vessel sidebranches, according to an exemplary embodiment of the present disclosure.

FIG. 21D shows two conductance curves with navigation starting at the left arm (solid line) and the right arm (dashed line), with advancement from the right arm showing more of a constant stepwise increase in conductance as the detector 102 of device approaches the heart as compared to advancement from the left arm. In both curves, pulsatility at the superior vena cava or the heart is readily identifiable.

Figure 21E:
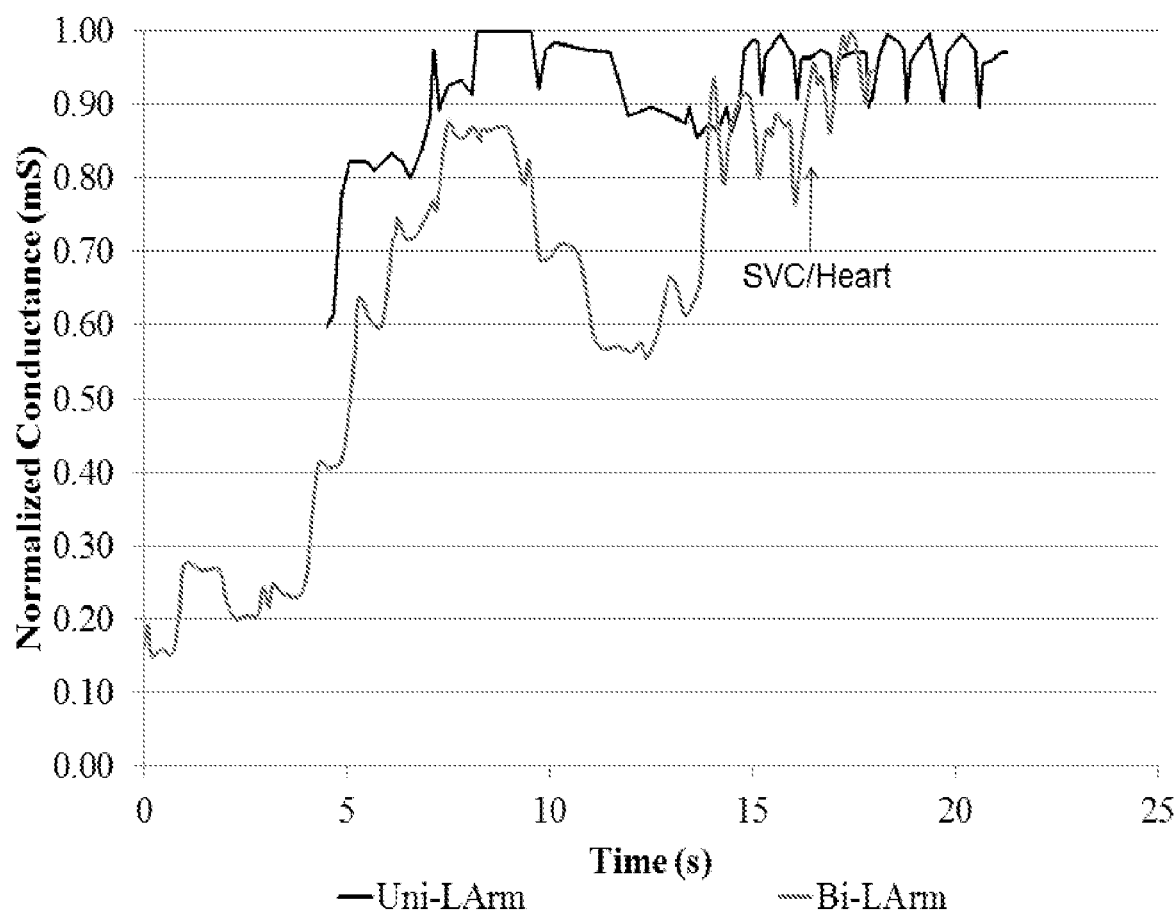
FIG. 21E shows conductance curves obtained using devices of the present disclosure while performing a bipolar method or a unipolar method, according to exemplary embodiments of the present disclosure.

FIG. 21E shows two conductance curves, one indicative of a bipolar method, and the other indicative of a unipolar approach. In general, "unipolar method" refers to using devices 100 of the present disclosure whereby one single electrode (referred to herein as electrode 115) having both excitation and detection functionality is positioned upon, or comprises part of, device 100. Electrode 115 may be one of electrodes 110, 112, 114, or 116, so long as electrode 115 can excite a field and detect within the field. Such a unipolar method could be performed using a combination of devices 100, sheaths 600, and/or pads 700 (which comprise exemplary systems 500 of the present disclosure), as shown in, for example, FIG. 19D, which shows an exemplary system 500 whereby one pad 700 includes an excitation electrode 110 (or another numbered excitation electrode) and whereby the other pad 700 has a detection electrode 114 (or another numbered detection electrode), and whereby a device 100 is used comprising electrode 115 (or another numbered electrode) having excitation and detection capabilities. In use, electrode 115 of device 100 would excite and detect, and the other excitation and detection functionality would exist from electrodes 110 and 114, for example, as shown in the figure.

As shown in FIG. 21E referenced above, the bipolar curve (starting at 0 seconds) and the unipolar curve (starting at about 5 seconds) both show changes in conductance over time as device 100 is advanced toward the heart, and both methods (bipolar and unipolar) show pulsatility at the superior vena cava or right atrium.

Figure 22A:
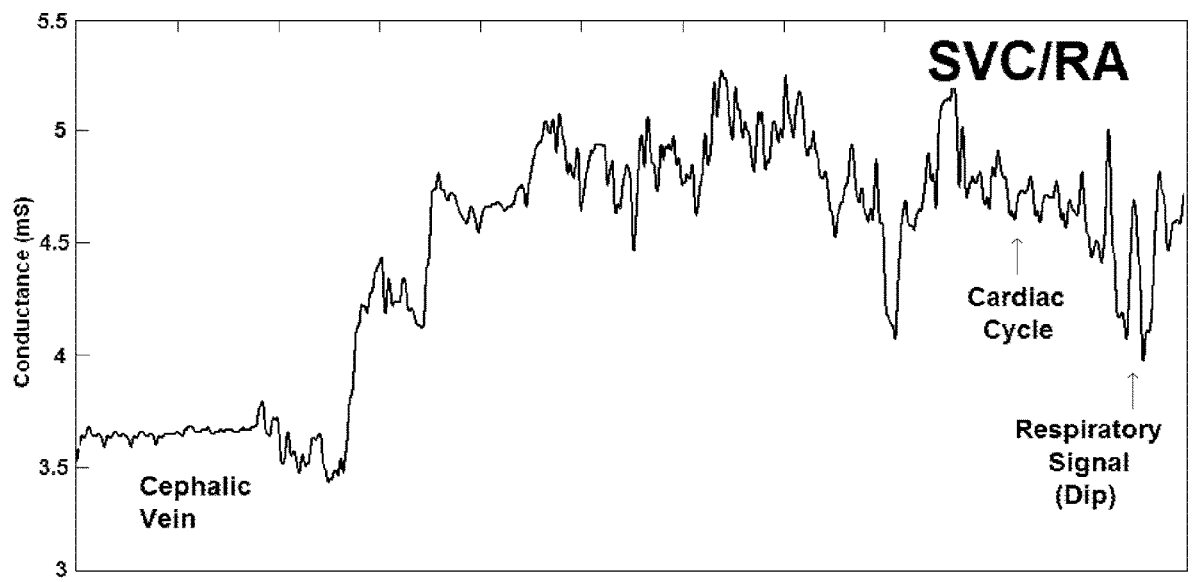
FIGS. 22A and 22B show conductance curves obtained using a unipolar stylet device and a tetrapolar guidewire device, respectively, according to exemplary embodiments of the present disclosure.
Figure 22B:
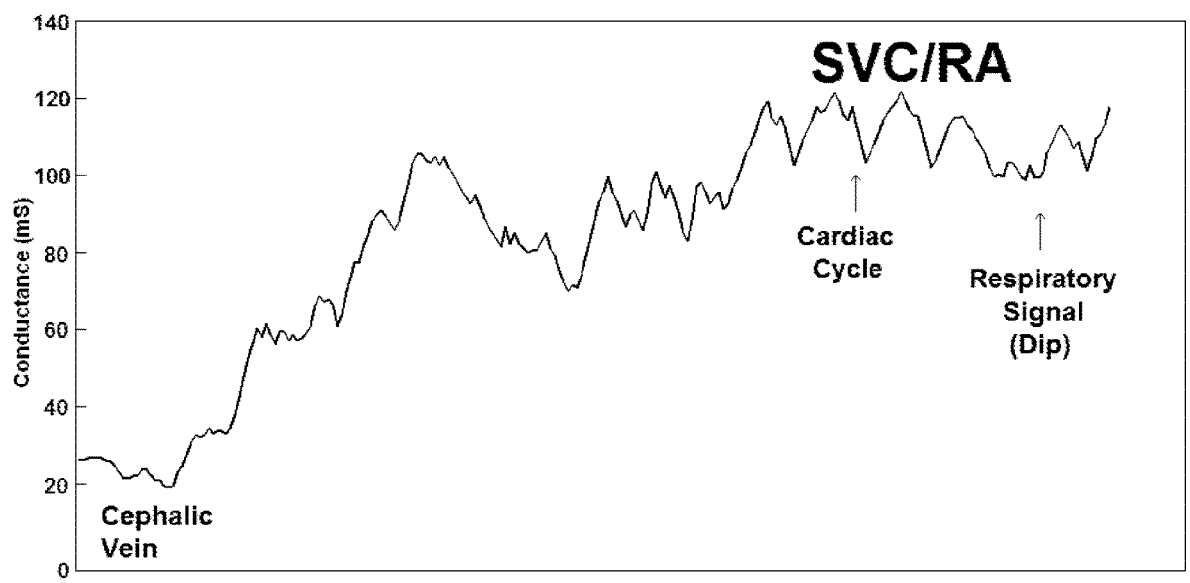

FIGS. 22A and 22B show additional curves using exemplary devices 100 of the present disclosure. FIG. 22A shows an exemplary conductance curve made using a unipolar device 100 of the present disclosure configured as a stylet, whereby advancement from the cephalic vein to the SVC/RA junction is shown, with cardiac pulsatility and a dip near the end of the curve indicative of a respiratory signal shown therein. FIG. 22B shows another exemplary conductance curve, but made using a tetrapolar device 100 of the present disclosure configured as a guidewire, whereby advancement from the cephalic vein to the SVC/RA junction is also shown, with cardiac pulsatility and a dip near the end of the curve indicative of a respiratory signal is also shown therein.

Furthermore, various devices 100 and/or systems 500 of the present disclosure may be configured as "tripolar" devices 100 and/or "tripolar" systems 500, useful to perform one or more methods of the present disclosure considered as "tripolar" methods. In general, a tripolar device 100, or a system 500 using a tripolar device 100, is configured using three poles, and a method of using the same to perform a tripolar method would be to excite a field using the tripolar device 100 or system 500 and obtain conductance measurements within the vasculature, consistent with other described methods of the present disclosure.

As noted above, exemplary CGW systems of the present disclosure provide an anatomically-based, accurate, safe, straightforward, and unbiased method for non-fluoroscopic delivery of CVCs 504 that fits well within the current clinical procedural workflow.

Various device 100 embodiments of the present disclosure can be used with patients experiencing arrhythmia, including atrial fibrillation (AF), for example. As atrial contraction can be detected using various devices 100 (such as pulsatility, referenced in additional detail herein), the presence of AF can potentially impact the phasic conductance signal. In an extreme case of AF where there is zero movement of the atrium (no phasic changes), the right atrium (RA) would be dilated and a significantly larger change from SVC to RA would be sensed using various exemplary devices 100 of the present disclosure. In such a use, the device 100 can be advanced into the right ventricle (RV) to detect the phasic changes and then retracted from there to the RA (no phasic change) and then to the SVC, which has a significantly smaller CSA than the RA. In addition, and for example, in a situation where a recognizable signature exists for a patient in AF, an exemplary device 100/system 500 of the present disclosure could detect the patient's rhythm as AF and signal the operator. This may be especially useful for post-surgical patients, and would also be valuable for any patient with unrecognized AF, for example. To capture this, console 902 could be programmed so that devices 100 would operate to identify the same.

In addition, there are an ever-increasing number of patients with abnormal cardiovascular anatomy due to surgical modifications secondary to congenital heart disease. In such patients, advancement of devices 100 through the patient's vasculature, for example, may take a different route than devices 100 would take with patients whose cardiovascular anatomy has not been surgically altered. For example, there may not always be a standard, progressive increase in vessel caliber when advancing to the heart. In some surgical corrections, insertion of a device 100 or other CVC 504 into a patient, without knowledge that the patient's anatomy is not normal and has been revised, an operator may be led to delivering the device 100 or other CVC 504, for example, to a location on the left side of the heart, which may put the patient at risk for embolism or thromboembolism. To address the same, various devices 100 and systems 500 of the present disclosure could be configured to detect such abnormalities and alert the operator prior to putting the patient at risk. For example, and in an instance of an obstruction, the conductance would decrease and then increase. In the algorithm(s) used, for example, certain rules could be provided to identify that if a decrease in conductance is monotonic (i.e., stays the same or continues to decrease over some specified period of time given the normal advance rate of the nurse or other operator, which would translate to a distance), this would signal that device 100 and/or another CVC 504 is being advanced in a wrong direction. In the case of transient passage of a local constriction or emboli, this would not be triggered.

While various embodiments of devices, systems, and methods for navigation and positioning of a central venous catheter within a patient have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method, comprising the steps of:
   puncturing a patient's skin to access a blood vessel of the patient;
   advancing at least part of a device into the blood vessel, the device comprising:
   a first pole and a second pole, each of the first pole and the second pole configured with excitation and detection functionality to generate an electric field within a mammalian body sufficient to obtain a plurality of field measurements therein; and
   an elongated body having a lumen extending distally therethrough and configured as a unipolar stylet for at least partial insertion into the blood vessel of the patient and advancement through a vasculature of the patient, the advancement dependent upon the plurality of field measurements indicating one or more locations of a portion of the elongated body within the vasculature,
   wherein the first pole is associated with the elongated body and the second pole is positioned on an external surface of the patient,
   wherein the indicating is based on a detected cross-sectional area change determined through conductance corresponding to the plurality of field measurements,
   wherein the step of advancing is performed while obtaining the plurality of field measurements, transmitting the field measurements to a console, and displaying the conductance or conductance-based images to assist a clinician in the advancement through the vasculature without X-ray, fluoroscopy, or ultrasound.

2. The method of claim 1, wherein the step of advancing is performed after introducing a guidewire into the blood vessel and advancing at least part of the elongated body over the guidewire.

3. The method of claim 1, wherein the step of advancing is continued as one or more values of the plurality of field measurements either generally increases or decreases.

4. The method of claim 1, further comprising the steps of:
   stopping advancement of the elongated body upon identification of one or more additional values of the plurality of field measurements that do not either generally increase or decrease;
   retracting the elongated body in response to or in connection with the one or more additional values; and
   re-advancing the elongated body in response to or in connection with identification of further field measurements that either generally increase or decrease.

5. The method of claim 1, further comprising the step of:
   stopping advancement of the elongated body when or after one or both of (i) a change in one or more additional values of the plurality of field measurements and/or (ii) pulsatility due to heart function is identified.

6. The method of claim 5, further comprising the step of:
   moving the elongated body to ultimately position at least part of the elongated body within the blood vessel, the step of moving performed to either pull-back or push-forward the elongated body.

7. The method of claim 6, wherein the step of moving the elongated body is performed using indicia positioned upon the elongated body as a guide.

8. The method of claim 5, wherein the method is performed to place the elongated body configured as a central venous catheter within the patient.

9. The method of claim 5, wherein the method is a unipolar method performed to place the elongated body configured as the unipolar stylet within the patient.

10. The method of claim 9, further comprising the steps of:
    positioning a central venous catheter over at least part of the elongated body; and
    advancing the central venous catheter over the elongated body to deliver a distal end of the central venous catheter to or near a distal end of the elongated body.

11. The method of claim 10, wherein the step of advancing at least part of the device into the blood vessel and the step of advancing the central venous catheter over the elongated body are performed simultaneously.

12. The method of claim 10, wherein the step of advancing at least part of the device into the blood vessel is performed prior to the step of advancing the central venous catheter over the elongated body.

13. The method of claim 10, further comprising the step of:
   removing the elongated body from the patient.

14. The method of claim 10, wherein at least one of the elongated body or the central venous catheter has indicia thereon, the indicia indicative of a location along the elongated body or the central venous catheter.

15. The method of claim 5, wherein the method is performed to position a distal end of the elongated body at a location within the patient selected from the group consisting of adjacent to a superior vena cava, at the superior vena cava, adjacent to a right atrium, at the right atrium, and at a superior vena cava/right atrium junction.

16. The method of claim 5, wherein the change is indicative of a portion of the elongated body being at or near a junction of a vena cava and an atrium of the patient.

17. A method, comprising the steps of:
   introducing a portion of a device into a blood vessel of a mammalian body via percutaneous intravascular introduction, the device comprising:
      a first pole and a second pole, each of the first pole and the second pole configured with excitation and detection functionality to generate an electric field within a vasculature of the mammalian body sufficient to obtain a plurality of field measurements therein; and
      an elongated body configured as a unipolar stylet for at least partial insertion into the blood vessel of the mammalian body and advancement through the vasculature,
         wherein the first pole is associated with the elongated body and the second pole is positioned on an external surface of a patient;
   advancing a portion of the elongated body through the vasculature toward a heart so long as the obtained field measurements are generally constant or generally changing in a consistent direction, the advancing dependent upon the plurality of field measurements indicating one or more locations of a portion of the elongated body within the vasculature,
      wherein the indicating is based on a detected cross-sectional area change determined through conductance corresponding to the plurality of field measurements, and
      wherein the field measurements are transmitted to a console for display of the conductance or conductance-based images to assist a clinician in advancement of the elongated body through the vasculature without X-ray, fluoroscopy, or ultrasound; and
   ceasing advancement of the portion of the elongated body when the field measurements indicate pulsatility due to heart function.

18. The method of claim 17, wherein the step of ceasing advancement is further performed based upon an identified stepwise change in conductance or voltage at or near a time when the field measurements indicate pulsatility.

19. The method of claim 18, wherein the stepwise change in conductance or voltage in response to or in connection with pulsatility is indicative of advancement of the portion of the elongated body to a superior vena cava or cavoatrial junction at a heart.

20. The method of claim 17, further comprising the step of:
   stopping advancement of the portion of the elongated body and retracting the same when the conductance or voltage measurements spike upward or downward or change in a direction opposite of the consistent direction.

21. The method of claim 20, wherein the spike upward or downward or change in the direction is indicative of advancement of the portion of the elongated body through the blood vessel in a direction other than directly to the heart though the blood vessel.

* * * * *